United States Patent [19]

Kölling et al.

[11] 4,088,780

[45] May 9, 1978

[54] SUBSTITUTED PHENYLGUANIDINES AND PROCESSES FOR THEIR PREPARATION AND USE

[75] Inventors: Heinrich Kölling, Haan; Herbert Thomas, Wuppertal-Elberfeld; Arno Widdig, Blecher; Hartmund Wollweber, Wuppertal-Elberfeld, all of Germany

[73] Assignee: Bayer Aktiengesellschaft, Germany

[21] Appl. No.: 690,073

[22] Filed: May 26, 1976

Related U.S. Application Data

[62] Division of Ser. No. 572,224, Apr. 28, 1975, Pat. No. 3,993,682.

[30] Foreign Application Priority Data

May 15, 1974 Germany .............................. 2423679

[51] Int. Cl.$^2$ ........................................... C07C 129/12

[52] U.S. Cl. .................................. 424/300; 260/402.5; 260/404.5; 260/465 D; 560/25; 560/27; 560/13; 560/9; 560/18

[58] Field of Search .................. 260/470, 404.5, 402.5, 260/471 C; 424/300

[56] References Cited

U.S. PATENT DOCUMENTS

| 3,812,173 | 5/1974 | Giraudon | 260/471 C |
| 3,869,503 | 3/1975 | Widdig et al. | 260/471 C |

Primary Examiner—Vivian Garner
Attorney, Agent, or Firm—Jacobs & Jacobs

[57] ABSTRACT

N-[2-(Substituted amido)phenyl]-N',N''-bis-carbonylguanidines bearing an optionally substituted phenoxy, phenylthio, phenylsulfinyl or phenylsulfonyl group in the 4- or 5-position of the 2-(substituted amido)-phenyl group are anthelmintic agents. The compounds, of which N-(2-acetamido-4-phenylthiophenyl)-N',N''-bis-carbomethoxyguanidine is a typical example, are prepared through the reaction of isothiourea-S-alkyl ether and an appropriately substituted 2-aminoanilide.

20 Claims, No Drawings

SUBSTITUTED PHENYLGUANIDINES AND PROCESSES FOR THEIR PREPARATION AND USE

CROSS-REFERENCE

This is a division of Ser. No. 572,224 filed Apr. 28, 1975, now U.S. Pat. No. 3,993,682.

DETAILED DESCRIPTION

The present invention pertains to substituted phenylguanidines, to methods for their preparation and use as anthelmintics, and to compositions thereof useful in such use.

Various N-formyl- and N-alkanamido-N',N''-bis(carbalkoxy)guanidines are described in German Offenlegungsschrift No. 2,117,293 as having anthelmintic properties. The effect of these properties however is relatively weak.

The present invention pertains to anthelmintic phenylguanidines of the formula:

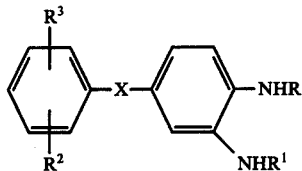

wherein X is oxygen, sulfur, sulfinyl or sulfonyl;
one of R and $R^1$ is $-COR^4$ and the other is

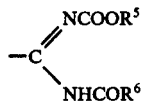

in which
$R^4$ is hydrogen or an unsubstituted or substituted alkyl, alkenyl of 2 to 4 carbon atoms, alkynyl of 2 to 4 carbon atoms, cycloalkyl, alkoxy, aryl or amino group;
$R^5$ is an unsubstituted or substituted alkyl, alkenyl or alkynyl group; and
$R^6$ is hydrogen or an unsubstituted or substituted alkyl, cycloalkyl, alkenyl, alkynyl, aryl, alkoxy, alkenyloxy or alkynyloxy group; and
each of $R^2$ and $R^3$ independent of the other is hydrogen, halogeno, cyano, or an unsubstituted or substituted alkyl, alkoxy, alkylthio, halogenoalkyl, amino or carbalkoxy group.

The foregoing guanidines can be depicted in several tautomeric forms, as shown below for the guanidine moiety only:

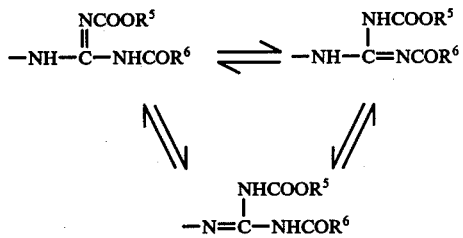

While for consistency and conciseness the structural formulas have been shown in only one of the foregoing ways, it will be appreciated that the actual compounds are inclusive of all tautomeric forms.

In the present context, the optionally-substituted alkyl groups embraced by $R^2$, $R^3$, $R^4$, $R^5$ and $R^6$ are straight- or branched hydrocarbon chains containing from 1 to 6, especially from 1 to 4, carbon atoms, as for example methyl, ethyl, n- and i-propyl, and n-, i- and t-butyl groups.

Alkenyl groups embraced by $R^5$ and $R^6$ will be straight or branched chained and contain from 2 to 6, especially 2 to 4, carbon atoms. Ethenyl, propenyl-(1), propenyl-(2) and butenyl-(3) can be mentioned as examples.

Alkynyl groups embraced by $R^5$ and $R^6$ will be straight- or branched chained and contain from 2 to 6, especially from 2 to 4, carbon atoms. Ethynyl, propynyl-(1), propynyl-(2) and butynyl-(3) are typical.

Alkoxy groups embraced by $R^2$, $R^3$, $R^4$ and $R^6$ are straight- or branched chained with from 1 to 6, especially from 1 to 4, carbon atoms. Methoxy, ethoxy, n- and i-propoxy and n-, i- and t-butoxy may be mentioned as examples.

Alkylthio groups embraced by $R^2$ and $R^3$ are straight- or branched chained with from 1 to 6, especially from 1 to 4, carbon atoms. Methylthio, ethylthio, n- and i-propylthio and n-, i- and t-butylthio may be mentioned as examples.

Alkanoyl groups embraced by $R^2$ and $R^3$ and the alkanoyl portion of alkanoylamino groups contain from 1 to 6, especially 2 to 4, carbon atoms. Formyl, acetyl, propionyl, n-butyryl and i-butyryl can be mentioned as examples of alkanoyl.

Carbalkoxy groups embraced by $R^2$ and $R^3$ can be straight or branched chained with from 2 to 7, especially 2 to 5, carbon atoms. Carbomethoxy, carbethoxy, carbo-n- and i-propoxy and carbo-n-, -i- and -t-butoxy can be mentioned as examples.

The halogenoalkyl groups embraced by $R^2$ and $R^3$ contain from 1 to 4, especially 1 or 2, carbon atoms and preferably from 1 to 5, especially 1 to 3, identical or different halogen atoms, the halogen atoms being fluorine, chlorine and bromine, especially fluorine and chlorine. Perhalogenated alkyl groups are preferred. Trifluoromethyl, chlorodifluoromethyl, bromomethyl, 2,2,2-trifluoroethyl and pentafluoroethyl can be mentioned as examples.

Halogeno embraced by $R^2$ and $R^3$ is fluoro, chloro, bromo or iodo, especially fluoro, chloro and bromo.

Aryl groups embraced by $R^4$ and $R^6$ contain from 6 to 10 carbon atoms in the aromatic ring system. Optionally-substituted phenyl and naphthyl can be mentioned as examples.

Aralkyl groups embraced by $R^4$ and $R^6$ are optionally-substituted in the aryl part or alkyl part with 6 to 10, preferably 6, carbon atoms in the aryl part and from 1 to 4, especially 1 or 2, carbon atoms in the alkyl part. The alkyl part can be straight- or branched chained. Optionally-substituted benzyl and phenylethyl are typical.

Cycloalkyl groups embraced by $R^4$ and $R^6$ are monocyclic, bicyclic or tricyclic cycloalkyl groups with from 3 to 10, especially 3 to 6, carbon atoms. Cyclopropyl, cyclobutyl, cyclopentyl, cyclohexyl, cycloheptyl, bicyclo[2.2.1]-heptyl, bicyclo[2.2.2]octyl and adamantyl are examples.

Alkenyloxy groups embraced by $R^6$ are straight- or branched chained from 2 to 6, especially 2 to 4, carbon atoms. Ethenyloxy, propenyl-(1)-oxy, propenyl-(2)-oxy and butenyl-(3)-oxy are examples.

Alkynyloxy groups embraced by $R^6$ are straight- or branched chained with from 2 to 6, especially 2 to 4, carbon atoms. Ethynyloxy, propynyl-(1)-oxy, propynyl-(2)-oxy and butynyl-(3)-oxy are examples.

The foregoing groups embraced by $R^2$, $R^3$, $R_4$, $R^5$ and $R^6$, other than hydrogen and halogeno, can in turn be optionally substituted as for example by acyl with 2 to 4 carbon atoms, carbalkoxy groups with 2 to 4 carbon atoms, alkoxyalkyl groups with 1 to 4 carbon atoms in the alkoxy part and 1 to 4 carbon atoms in the alkyl part, and aralkyl groups with 1 to 4 carbon atoms in the alkyl part and 6 carbon atoms in the aryl part.

Particularly preferred compounds are those in which
$R^2$ and $R^3$ are each independently hydrogen, methyl, ethyl, n-butyl, methoxy or ethoxy, fluoro, chloro, bromo, cyano, methylmercapto, trifluoromethyl, acetyl, propionyl, acetylamino or carbmethoxyamino;
$R^4$ is methyl, ethyl, propyl, n-butyl, i-butyl, n-pentyl, n-hexyl, cyclopentyl, cyclohexyl, phenyl, benzyl, methoxymethyl, methoxy, ethoxy, phenoxymethyl, methylamino, ethylamino, n-butylamino, n-cyanopentylamino or β-methoxyethylamino;
$R^5$ is methyl, ethyl, i-propyl, sec.-butyl, propenyl-(2) or propinyl; and
$R^6$ is methyl, ethyl, propyl, isopropyl, n-amyl, isoamyl, n-butyl, cyclohexyl, benzyl, methoxymethyl, phenoxymethyl, allyl, crotyl, methallyl, methoxy, ethoxy, i-propoxy, sec.-butoxy, propenyl-(2)-oxy, propynyl-(2)-oxy, or 2-methyl-propenyl-(2)-oxy.

The compounds are prepared by a process which comprises (a.) reacting a compound of the formula:

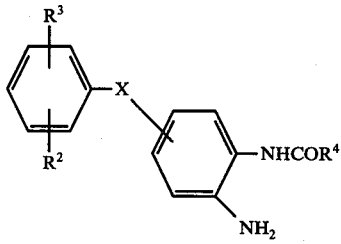

wherein $R^2$, $R^3$ and $R^4$ are as defined above, with an isothiourea-S-alkyl ether of the formula:

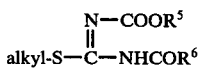

in the presence of an acid and in an inert organic solvent, or (b.) treating a compound of the formula:

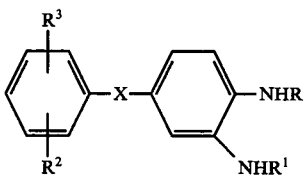

wherein R, $R^1$, $R^2$ and $R^3$ are as defined above and X is sulfur with an oxidizing agent to yield the corresponding compound wherein X is sulfinyl or sulfonyl.

The first of the foregoing two reactions is generally conducted in an inert organic solvent, generally a polar solvent such as an alcohol, as for example methanol, ethanol or isopropanol, a ketone such as acetone or methylethyl ketone, an alkanoic acid such as acetic acid, an ether such as ethyl ether and tetrahydrofuran. The medium may be aqueous, utilizing one of the foregoing water-miscible solvents in combination with water. The reaction is carried out at a temperature of from 0° to 120° C, preferably from 30° to 100° C, preferably at the boiling point of the solvent, in the presence of an organic or inorganic acid such as hydrochloric acid, sulfuric acid, nitric acid, formic acid, acetic acid, p-toluenesulfonic acid, and the like. Equimolar amounts of reactants are generally employed although this can vary by about ± 20% without significant effect on the yield. An alkylmercaptan is formed as a by-product and the desired product is obtained by cooling the reaction mixture and collecting the solid which can be purified if desired by conventional techniques such as recrystallization.

In the foregoing second reaction, a compound of the present invention wherein X is sulfur treated with one molar equivalent of an oxidizing agent to yield the corresponding compound where X is sulfinyl or with two moles to yield the corresponding compound where X is sulfonyl. The oxidizing agents include organic peroxoacids, such as peracetic acid, performic acid, perbenzoic acid, m-chlorobenzoic acid, monoperphthalic acid and the like; inorganic peroxides, such as hydrogen peroxide; organic acids dissolved in water or otherwise diluted; inorganic oxidation agents such as chromic acid, nitric acid, potassium permanganate, chlorine or bromine; halo oxy acids such as hypochlorous acid, chlorous acid, chloric acid, perchloric acid, tert.-butyl hypochlorite, methyl hypochlorite, tert.-butylchromate and the like; or N-haloimides such as N-chloro-succinimide and N-bromo-succinimide, N-halo sulphonic acid amides or N-halo carboxylic acid amides.

Reaction conditions are selected, in a manner known to the art, so that oxidation potential is adjusted for the production of either sulfoxides or sulfones.

Many of the thioureas used as starting materials in the first reaction are known (see Olin and Dains, J. Amer. Chem. Soc. 52, 3326 (1930) and U.S. Pat. No. 2,993,502) while others can easily be obtained by known processes. The thioureas are generally prepared from known N-acylthioureas [see, e.g. "Berichte der deutschen Chemischen Gesellschaft", 6, 755 (1873); Ann, Chim. (5) 11, 313 (1877); J. Amer. Chem. Soc. 62, 3274 (1940)], which are reacted with alkylating agents such as alkyl halides, alkyl sulphates or alkyl sulphonates to give the corresponding S-alkyl-N-acyl-isothioureas [see, e.g. J. Org. Chem. 30, 560, (1965); Chem. Pharm. Bull. (Tokyo), 9, 245, (1961)]. These S-alkyl-N-acyl-isothioureas are then reacted with halogenoformic acid esters or with pyrocarbonic acid dialkyl esters [see, e.g., Ber. dtsch, chem. Ges. 71, 1797 (1938)] to give the S-alkyl-N-acyl-N'-alkoxycarbonyl-isothioureas, which corresponds to the known substitution of S-alkyl-isothioureas with chloroformic acid alkyl esters [see, e.g. J. Amer. Chem. Soc. 52, 3326 (1930)].

The following are typical isothioureas which can be employed in accordance with the process of this invention: N,N'-bis-methoxycarbonyl-S-methyl-isothiourea (melting point 99° – 100° C), N,N'-bis-ethoxycarbonyl-S-methyl-isothiourea (melting point 50° – 51° C), N-ethoxycarbonyl-N'-propionyl-S-methyl-isothiourea (melting point 92° – 94° C), N-methoxycarbonyl-N'- propionyl-S-methyl-isothiourea (melting point 97° – 99° C), N-methoxycarbonyl-N'-ethoxyacetyl-S-methyl-isothiourea (melting point 69° – 70° C), N-methoxycarbonyl-N' -cyclohexylcarbonyl-S-methyl-isothiourea (m.p. 67° – 68° C), N-methoxycarbonyl-N'-phenylacetyl-S-methyl-isothiourea (m.p. 55° – 56° C), N-ethoxycarbonyl-N'-benzoyl-S-methyl-isothiourea (m.p. 79° – 80° C), N-ethoxycarbonyl-N'-methoxycarbonyl-S-methyl-isothiourea (m.p. 69° C), N-allyloxycarbonyl-N'-methoxycarbonyl-S-methyl-isothiourea, N-propinyloxycarbonyl-N'-methoxycarbonyl-S-isothiourea, N,N'-bis-allyloxycarbonyl-S-methyl-isothiourea and N,N'-bis-propinyloxycarbonyl-S-methyl-isothiourea.

Most of the 2-aminoanilide starting materials are known. Those that are not previously known can be readily prepared by methods analogous to those disclosed in the literature. For example, a 2-nitroaniline having the appropriate substituent in the 4- or 5-position, e.g., phenoxy, phenylthio, phenylsulfinyl or phenylsulfonyl, can be N-acylated with an acid chloride of the formula $R^4COCl$ to yield the corresponding 2-nitro-4- or 5-substituted anilide which is hydrogenated as with Raney nickel to yield the 2-amino-4- or 5-substituted anilide. The 2-nitroanilines having a phenylsulfinyl or phenylsulfonyl group in the 4- or 5-positions can also be obtained from the corresponding phenylthio compounds through controlled oxidation analogous to that described above, e.g. using hydrogen peroxide in acetic anhydride or perbenzoic acid in dioxane or chloroform, to yield the sulfinyl compound, or hydrogen peroxide in glacial acetic acid to yield the sulfone. The 4- and 5-phenylsulfonyl-2-nitroanilines can also be obtained by the reaction of a sodiumbenzenesulfinate with a 4- or 5-chloro-2-nitroaniline as for example dimethylformamide at about 140° C.

The following may be mentioned as examples of the 2-amino-anilides employed as starting materials: 2-amino-5-phenoxy-acetanilide, 2-amino-5-phenoxy-propionanillide, 2-amino-5-phenoxy-butyranilide, 2-amino-5-phenoxy-iso-butyranilide, 2-amino-5-phenoxy-valeranilide, 2-amino-5-phenoxy-iso-valeranilide, 2-amino-5-phenoxy-caproanilide, 2-amino-5-phenoxy-iso-caproanilide, 2-amino-5-phenoxy-cyclopentanecarboxylic acid anilide, 2-amino-5-phenoxy-cyclohexanecarboxylic acid anilide, 2-amino-5-phenoxy-phenylacetanilide, 2-amino-5-phenoxy-phenoxyacetanilde, 2-amino-5-phenoxy-benzanilide, N-(2-amino-5-phenoxy-phenyl)-N'-methyl-urea, N-(2-amino-5-phenoxy-phenyl)-N'-ethyl-urea, N-(2-amino-5-phenoxy-phenyl)-N'-butyl-urea, N-(2-amino-5-phenoxy-phenyl)-N'-ω-cyanopentyl-urea, N-(2-amino-5-phenoxy-phenyl)-N'-β-methoxyethyl-urea, N-(2-amino-5-phenoxy-phenyl)-N'-benzyl-urea, N-(2-amino-5-phenoxy-phenyl)-N'-phenyl-urea, 2-amino-5-(4-methyl-phenoxy)-propionanilide, 2-amino-5-(4-methyl-phenoxy)-butyranilide, 2-amino-5-(4-methyl-phenoxy)-acetanilide, 2-amino-5-(3-methyl-phenoxy)-propionanilide, 2-amino-5-(3-methyl-phenoxy)-butyranilide, 2-amino-5-(3-methyl-phenoxy)-acetanilide, 2-amino-5-(2-methyl-phenoxy)-propionanilide, 2-amino-5-(2-methyl-phenoxy)-butyranilide, 2-amino-5-(2-methyl-phenoxy)-acetanilide, 2-amino-5-(4-chloro-phenoxy)-propionanilide, 2-amino-5-(4-chloro-phenoxy)-butyranilide, 2-amino-5-(4-chloro-phenoxy)-acetanilide, 2-amino-5-(3-chloro-phenoxy)-propionanilide, 2-amino-5-(3-chloro-phenoxy)-butyranilide, 2-amino-5-(3-chloro-phenoxy)-acetanilide, 2-amino-5-(2-chloro-phenoxy)-propionanilide, 2-amino-5-(2-chloro-phenoxy)-butyranilide, 2-amino-5-(2-chloro-phenoxy)-acetanilide, 2-amino-5-(4-methoxy-phenoxy)-propionanilide, 2-amino-5-(4-methoxy-phenoxy)-butyranilide, 2-amino-5-(4-methoxy-phenoxy)-acetanilide, 2-amino-5-(3-methoxy-phenoxy)-propionanilide, 2-amino-5-(3-methoxy-phenoxy)-butyranilide, 2-amino-5-(3-methoxy-phenoxy)-acetanilide, 2-amino-5-(4-methylthio-phenoxy)-propionanilide, 2-amino-5-(4-methylthio-phenoxy)-butyranilide, 2-amino-5-(4-methylthiophenoxy)-acetanilide, 2-amino-5-(3-methylthio-phenoxy)-propionanilide, 2-amino-5-(3-methylthio-phenoxy)-butyranilide, 2-amino-5-(3-methylthio-phenoxy)-acetanilide, 2-amino-5-(4-cyano-phenoxy)-propionanilide, 2-amino-5-(4-cyano-phenoxy)-butyranilide, 2-amino-5-(4-cyano-phenoxy)-acetanilide, 2-amino-5-(3-cyano-phenoxy)-propionanilide, 2-amino-5-(3-cyanophenoxy)-butyranilide, 2-amino-5-(3-cyano-phenoxy)-acetanilide, 2-amino-5-(4-acetyl-phenoxy)-propionanilide, 2-amino-5-(4-acetyl-phenoxy)-butyranilide, 2-amino-5-(4-acetyl-phenoxy)-acetanilide, 2-amino-5-(4-propionyl-phenoxy)-propionanilide, 2-amino-5-(4-propionyl-phenoxy)-butyranilide, 2-amino-5-(4-propionyl-phenoxy)-acetanilide, 2-amino-5-(4-acetylaminophenoxy)-propionanilide, 2-amino-5-(4-acetylamino-phenoxy)-butyranilide, 2-amino-5-(4-acetylamino-phenoxy)-acetanilide, 2-amino-5-(4-methoxycarbonylamino-phenoxy)-propionanilide, 2-amino-5-(4-methoxycarbonylamino-phenoxy)-butyranilide, 2-amino-5-(4-methoxycarbonylamino-phenoxy)-acetanilide, 2-amino-5-(4-methoxycarbonyl-phenoxy)-propionanilide, 2-amino-5-(4-methoxycarbonyl-phenoxy)-butyranilide, 2-amino-5-(4-methoxycarbonyl-phenoxy)-acetanilide, 2-amino-5-(3,4-dimethylphenoxy)-propionanilide, 2-amino-5-(3,4-dimethyl-phenoxy)-butyranilide, 2-amino-5-(3,4-dimethyl-phenoxy)-acetanilide, 2-amino-5-(2-methyl-4-chloro-phenoxy)-propionanilide, 2-amino-5-(2-methyl-4-chloro-phenoxy)-butyranilide, 2-amino-5-(2-methyl-4-chloro-phenoxy)-acetanilide, 2-amino-5-(4-ethyl-phenoxy)-propionanilide, 2-amino-5-(4-ethyl-phenoxy)-butyranilide, 2-amino-5-(4-ethyl-phenoxy)-acetanilide, 2-amino-5-(3,4-dichloro-phenoxy)-propionanilide, 2-amino-5-(3,4-dichloro-phenoxy)-butyranilide, 2-amino-5-(3,4-dichloro-phenoxy)-acetanilide, 2-amino-5-(4-bromo-phenoxy)-propionanilide, 2-amino-5-(4-bromo-phenoxy)-butyranilide, 2-amino-5-(4-bromophenoxy)-acetanilide, 2-amino-5-(3,5-dimethyl-phenoxy)-propionanilide, 2-amino-5-(dimethyl-phenoxy)-butyranilide, 2-amino-5-(3,5-dimethyl-phenoxy)-acetanilide, 2-amino-5-(4-butyl-phenoxy)-propionanilide, 2-amino-5-(4-butyl-phenoxy)-butyranilide, 2-amino-5-(4-butyl-phenoxy)-acetanilide, 2-amino-5-(3-butyl-phenoxy)-propionanilide, 2-amino-5-(3-butylphenoxy)-butyranilide, 2-amino-5-(3-butyl-phenoxy)-acetanilide, 2-amino-4-phenoxy-acetanilide, 2-amino-4-phenoxy-propionanilide, 2-amino-4-phenoxy-butyranilide, 2-amino-4-phenoxy-iso-butyranilide, 2-amino-4-phenoxy-valeranilide, 2-amino-4-phenoxy-iso-valeranilide, 2-amino-4-phenoxy-caproanilide, 2-amino-4-phenoxy-iso-caproanilide, 2-amino-4-phenoxy-cyclopentanecarboxylic acid anilide, 2-amino-4-phenoxycyclohexanecarboxylic acid anilide, 2-amino-4-phenoxy-phenylacetanilide, 2-amino-4-phenoxy-phenoxyacetanilide, 2-amino-4-phenoxy-benzanilide, N-(2-amino-4-phenoxy-phenyl)-N'-methylurea, N-(2-amino-4-phenoxy-phenyl)-N'-ethyl-urea, N-(2-amino-4-phenoxy-phenyl)-N'-butyl-urea, N-(2-amino-4-phenoxy-phenyl)-N'-ω-cyanopentyl-urea, N-(2-amino-4-phenoxy-phenyl)-N'-β-methoxyethyl-urea, N-(2- amino-4-phenoxy-phenyl)-N'-benzylurea, N-(2-amino-4-phenoxy-phenyl)-N'-phenyl-urea, 2-amino-4-(4-methyl-phenoxy)-propionanilide, 2-amino-4-(4-methyl-phenoxy)-butyranilide, 2-amino-4-(4-methyl-phenoxy)-acetanilide, 2-amino-4-(3-methyl-phenoxy)-propionanilide, 2-amino-4-(3-methyl-phenoxy)-butyranilide. 2-amino-4-(3-methyl-phenoxy)-acetanilide, 2-amino-4-(2-methyl-phenoxy)-propionanilide, 2-amino-4-(2-methyl-phenoxy)-butyranilide, 2-amino-4-(2-methylphenoxy)-acetanilide, 2-amino-4-(4-chloro-phenoxy)-propionanilide, 2-amino-4-(4-chloro-phenoxy)-butyranilide, 2-amino-4-(4-chloro-phenoxy)-acetanilide, 2-amino-4-(3-chloro-phenoxy)-propionanilide, 2-amino-4-(3-chloro-phenoxy)-butyranilide, 2-amino-4-(3-chloro-phenoxy)-acetanilide, 2-amino-4-(2-chlorophenoxy)-propionanilide, 2-amino-4-(2-chloro-phenoxy)-butyranilide, 2-amino-4-(2-chloro-phenoxy)-acetanilide, 2-amino-4-(4-methoxy-phenoxy)-propionanilide, 2-amino-4-(4-methoxy-phenoxy)-butyranilide, 2-amino-4-(4-methoxy-phenoxy)-acetanilide, 2-amino-4-(3-methoxy-phenoxy)-propionanilide, 2-amino-4-(3-methoxy-phenoxy)-butyranilide, 2-amino-4-(3-methoxy-phenoxy)-acetanilide, 2-amino-4-(4-methylthio-phenoxy)-propionanilide, 2-amino-4-(4-methylthio-phenoxy)-butyranilide, 2-amino-4-(4-methylthio-phenoxy)-acetanilide, 2-amino-4-(3-methylthiophenoxy)-propionanilide, 2-amino-4-(3-methylthio-phenoxy)-butyranilide, 2-amino-4-(3-methylthio-phenoxy)-acetanilide, 2-amino-4-(4-cyano-phenoxy)-propionanilide, 2-amino-4-(4-cyano-phenoxy)-butyranilide, 2-amino-4-(4-cyano-phenoxy)-acetanilide, 2-amino-4-(3-cyano-phenoxy)-propionanilide, 2-amino-4-(3-cyano-phenoxy)-butyranilide, 2-amino-4-(3-cyanophenoxy)-acetanilide, 2-amino-4-(4-acetyl-phenoxy)-propionanilide, 2-amino-4-(4-acetyl-phenoxy)-butyranilide, 2-amino-4-(4-acetyl-phenoxy)-acetanilide, 2-amino-4-(4-propionyl-phenoxy)-propionanilide, 2-amino-4-(4-propionyl-phenoxy)-butyranilide, 2-amino-4-(4-propionyl-phenoxy)-acetanilide, 2-amino-4-(4-acetaylamino-phenoxy)-propionanilide, 2-amino-4-(4-acetylamino-phenoxy)-butyranilide, 2-amino-4-(4-acetylamino-phenoxy)-acetanilide, 2-amino-4-(4-methoxycarbonylaminophenoxy)-propionanilide, 2-amino-4-(4-methoxycarbonylaminophenoxy)-butyranilide, 2-amino-4-(4-methoxycarbonylaminophenoxy)-acetanilide, 2-amino-4-(4-methoxycarbonyl-phenoxy)-propionanilide, 2-amino-4-(4-methoxycarbonyl-phenoxy)-butyranilide, 2-amino-4-(4-methoxycarbonyl-phenoxy)-acetanilide, 2-amino-4-(3,4-dimethyl-phenoxy)-propionanilide, 2-amino-4-(3,4-dimethyl-phenoxy)-butyranilide, 2-amino-4-(3,4-dimethyl-phenoxy)-acetanilide, 2-amino-4-(2-methyl-4-chloro-phenoxy)-propionanilide, 2-amino-4-(2-methyl-4-chloro-phenoxy)-butyranilide, 2-amino-4-(2-methyl-4-chloro-phenoxy)-acetanilide, 2-amino-4-(4-ethyl-phenoxy)-propionanilide, 2-amino-4-(4-ethyl-phenoxy)-butyranilide, 2-amino-4-(4-ethyl-phenoxy)-acetanilide, 2-amino-4-(3,4-dichloro-phenoxy)-propionanilide, 2-amino-4-(3,4-dichloro-phenoxy)-butyranilide, 2-amino-4-(3,4-dichloro-phenoxy)-acetanilide, 2-amino-4-(4-bromo-phenoxy)-propionanilide, 2-amino-4-bromo-phenoxy)-butyranilide, 2-amino-4-(4-bromo-phenoxy)-acetanilide, 2-amino-4-(3,5-dimethyl-phenoxy)-propionanilide, 2-amino-4-(3,5-dimethyl-phenoxy)-butyranilide, 2-amino-4-(3,5-dimethyl-phenoxy)-acetanilide, 2-amino-4-(4-butyl-phenoxy)-propionanilide, 2-amino-4-(4-butyl-phenoxy)-butyranilide, 2-amino-4-(4-butyl-phenoxy)-acetanilide, 2-amino-4-(3-butyl-phenoxy)-propionanilide, 2-amino-4-(3-butyl-phenoxy)-butyranilide, 2-amino-4-(3-butyl-phenoxy)-acetanilide, 2-amino-5-phenylthio-acetanilide, 2-amino-5-phenylthio-propionanilide, 2-amino-5-phenylthio-butyranilide, 2-amino-5-phenylthio-iso-butyranilide, 2-amino-5-phenylthio-valeranilide, 2-amino-5-phenylthio-iso-valeranilide, 2-amino-5-phenylthio-caproanilide, 2-amino-5-phenylthio-iso-caproanilide, 2-amino-5-phenylthio-cyclopentanecarboxylic acid anilide, 2-amino-5-phenylthio-cyclohexanecarboxylic acid anilide, 2-amino-5-phenylthio-phenylacetanilide, 2-amino-5-phenylthio-phenoxyacetanilide 2-amino-5-phenylthio-benzanilide, N-(2-amino-5-phenylthio-phenyl)-N'-methyl-urea, 2-amino-5-phenylthio-methoxyacetanilide, N-(2-amino-5-phenyl-thio-phenyl)-N'-butyl-urea, N-(2-amino-5-phenylthio-phenyl)-N'-ω-cyanopentyl-urea, N-(2-amino-5-phenylthio-phenyl)-N'-β-methoxyethyl-urea, N-(2-amino-5-phenylthio-phenyl)-N'-benzylurea, N-(2-amino-5-phenylthio-phenyl)-N'-phenyl-urea, 2-amino-5-(4-methyl-phenylthio)-propionanilide, 2-amino-5-(4-methyl-phenylthio)-butyranilide, 2-amino-5-(4-methyl-phenylthio)-acetanilide, 2-amino-5-(3-methyl-phenylthio)-propionanilide, 2-amino-5-(3-methyl-phenylthio)-butyranilide, 2-amino-5-(3-methyl-phenylthio)-acetanilide, 2-amino-5-(2-methyl-phenylthio)-propionanilide, 2-amino-5-(2-methyl-phenylthio)-butyranilide, 2-amino-5-(2-methyl-phenylthio)-acetanilide, 2-amino-5-(4-chloro-phenylthio)-propionanilide, 2-amino-5-(4-chloro-phenylthio)-butyranilide, 2-amino-5-(4-chloro-phenylthio)-acetanilide, 2-amino-5-(3-chloro-phenylthio)-propionanilide, 2-amino-5-(3-chloro-phenylthio)-butyranilide, 2-amino-5-(3-chloro-phenylthio)-acetanilide, 2-amino-5-(2-chloro-phenylthio)-propionanilide, 2-amino-5-(2-chloro-phenylthio)-butyranilide, 2-amino-5-(2-chloro-phenylthio)-acetanilide, 2-amino-5-(4-methoxy-phenylthio)-propionanilide, 2-amino-5-(4-methoxy-phenylthio)-butyranilide, 2-amino-5-(4-methoxy-phenylthio)-acetanilide, 2-amino-5-(3-methoxy-phenylthio)-propionanilide, 2-amino-5-(3-methoxyphenylthio)-butyranilide, 2-amino-5-(3-methoxy-phenylthio)-acetanilide, 2-amino-5-(4-methylthio-phenylthio)-propionanilide, 2-amino-5-(4-methylthio-phenylthio)-butyranilide, 2-amino-5-(4-methylthio-phenylthio)-acetanilide, 2-amino-5-(3-methylthio-phenylthio)-propionanilide, 2-amino-5-(3-methylthio-phenylthio)-butyranilide, 2-amino-5-(3-methylthio-phenylthio)-acetanilide, 2-amino-5-(4-cyano-phenylthio)-propionanilide, 2-amino-5-(4-cyano-phenylthio)-butyranilide, 2-amino-5-(4-cyano-phenylthio)-acetanilide, 2-amino-5-(3-cyano-phenylthio)-propionanilide, 2-amino-5-(3-cyano-phenylthio)-butyranilide, 2-amino-5-(3-cyano-phenylthio)-acetanilide, 2-amino-5-(4-acetyl-phenylthio)-propionanilide, 2-amino-5-(4-acetyl-phenylthio)-butyranilide, 2-amino-5-(4-acetyl-phenylthio)-acetanilide, 2-amino-5-(4-propionyl-phenylthio)-propionanilide, 2-amino-5-(4-propionyl-phenylthio)-butyranilide, 2-amino-5-(4-propionyl-phenylthio)-acetanilide, 2-amino-5-(4-acetylamino-phenylthio)-propionanilide, 2-amino-5-(4-acetylamino-phenylthio)-butyranilide, 2-amino-5-(4-acetylamino-phenylthio)-acetanilide, 2-amino-5-(4-methoxycarbonylamino-phenylthio)-propionanilide, 2-amino-5-(4-methoxycarbonylamino-phenylthio)-butyranilide, 2-amino-5-(4-methoxycarbonylamino-phenylthio)-acetanilide, 2-amino-5-(4-methoxycarbonyl-phenylthio)-propionanilide, 2-amino-5-(4-methoxycarbonyl-phenylthio)-butyranilide, 2-amino-5-(4-methoxycarbonyl-phenylthio)-acetanilide, 2-amino-5-(3,4-dimethylphenylthio)-propionanilide, 2-amino-5-(3,4-dimethyl-phenylthio)-butyranilide, 2-amino-5-(3,4-dimethyl-phenylthio)-acetanilide, 2-amino-5-(2-methyl-4-chloro-phenylthio)-propionanilide, 2-amino-5-(2-methyl-4-chloro-phenylthio)-butyranilide, 2-amino-5-(2-methyl-4-chloro-phenylthio)-acetanilide, 2-amino-5-(4-ethyl-phenylthio)-propionanilide, 2-amino-5-(4-ethyl-phenylthio)-butyranilide, 2-amino-5-(4-ethyl-phenylthio)-acetanilide, 2-amino-5-(3,4-dichloro-phenylthio)-propionanilide, 2-amino-5-(3,4-dichloro-phenylthio)-butyranilide, 2-amino-5-(3,4-dichlorophenylthio)-acetanilide, 2-amino-5-(4-bromo-phenylthio)-propionanilide, 2-amino-5-(4-bromo-phenylthio)-butyranilide, 2-amino-5-(4-bromo-phenylthio)-acetanilide, 2-amino-5-(3,5-dimethyl-phenylthio)-propionanilide, 2-amino-5-(3,5-dimethyl-phenylthio)-butyranilide, 2-amino-5-(3,5-dimethyl-phenylthio)-acetanilide, 2-amino-5-(4-butyl-phenylthio)-propionanilide, 2-amino-5-(4-butyl-phenylthio)-butyranilide, 2-amino-5-(4-butyl-phenylthio)-acetanilide, 2-amino-5-(3-butyl-phenylthio)-propionanilide, 2-amino-5-(3-butyl-phenylthio)-butyranilide, 2-amino-5-(3-butyl-phenylthio)-acetanilide, 2-amino-4-phenylthio-acetanilide, 2amino-4-phenylthio-propionanilide, 2-amino-4-phenylthio-butyranilide, 2-amino-4-phenylthio-iso-butyranilide, 2-amino-4-phenylthio-valeranilide, 2-amino-4-phenylthio-iso-valeranilide, 2-amino-4-phenylthio-caproanilide, 2-amino-4-phenylthio-iso-caproanilide, 2-amino-4-phenylthio-cyclopentanecarboxylic acid anilide, 2-amino-4-phenylthio-cyclohexanecarboxylic acid anilide, 2-amino-4-phenylthio-phenylacetanilide, 2-amino-4-phenylthio-phenoxyacetanilide, 2-amino-4-phenylthio-benzanilide, N-(2-amino-4-phenylthio-phenyl)-N'-methyl-urea, N-(2-amino-4-phenylthio-phenyl)-N'-ethyl-urea, N-(2-amino-4-phenylthio-phenyl)-N'-butyl-urea, N-(2-amino-4-phenylthio-phenyl)-N'-ω-cyanopentyl-urea, N-(2-amino-4-phenylthio-phenyl)-N'-β-methoxyethyl-urea, N-(2-amino-4-phenylthio-phenyl)-N'-benzyl-urea, N-(2-amino-4-phenylthio-phenyl)-N'-phenyl-urea, 2-amino-4-(4-phenylthio)-propionanilide, 2-amino-4-(4-methyl-phenylthio)-butyranilide, 2-amino-4-(4-methyl-phenylthio)-acetanilide, 2-amino-4-(3-methyl-phenylthio)-propionanilide, 2-amino-4-(3-methyl-phenylthio)-butyranilide, 2-amino-4-(3-methyl-phenylthio)-acetanilide, 2-amino-4-(2-methyl-phenylthio)-propionanilide, 2-amino-4-(2-methyl-phenylthio)-butyranilide, 2-amino-4-(2-methyl-phenylthio)-acetanilide, 2-amino-4-(4-chloro-phenylthio)-propionanilide, 2-amino-4-(4-chloro-phenylthio)-butyranilide, 2-amino-4-(4-chloro-phenylthio)-acetanilide, 2-amino-4-(3-chloro-phenylthio)-propionanilide, 2-amino-4-(3-chloro-phenylthio)-butyranilide, 2-amino-4-(3-chloro-phenylthio)-acetanilide, 2-amino-4-(2-chloro-phenylthio)-propionanilide, 2-amino-4-chloro phenylthio)-butyranilide, 2-amino-4-(2-chloro-phenylthio)-acetanilide, 2-amino-4-(4-methoxy-phenylthio)-propionanilide, 2-amino-4-(4-methoxy-phenylthio)-butyranilide, 2-amino-4-(4-methoxy-phenylthio)-acetanilide, 2-amino-4-(3-methoxy-phenylthio)-propionanilide, 2-amino-4-(3-methoxy-phenylthio)-butyranilide, 2-amino-4-(3-methoxy-phenylthio)-acetanilide, 2-amino-4-(4-methylthio-phenylthio)-propionanilide, 2-amino-4-(4-methylthio-phenylthio)-butyranilide, 2-amino-4-(4-methylthio-phenylthio)-acetanilide, 2-amino-4-(3-methylthio-phenylthio)-propionanilide, 2-amino-4-(3-methylthio-phenylthio)-butyranilide, 2-amino-4-(3-methylthio-phenylthio)-acetanilide, 2-amino-4-(4-cyano-phenylthio)-propionanilide, 2-amino-4-(4-cyano-phenylthio)-butyranilide, 2-amino-4-(4-cyano-phenylthio)-acetanilide, 2-amino-4-(3-cyano-phenylthio)-propionanilide, 2-amino-4-(3-cyano-phenylthio)-butyranilide, 2-amino-4-(3-cyano-phenylthio)-acetanilide, 2-amino-4-(4-acetyl-phenylthio)-propionanilide, 2-amino-4-(4-acetyl-phenylthio)-butyranilide, 2-amino-4-(4-acetyl-phenylthio)-acetanilide, 2-amino-4-(4-propionyl-phenylthio)-propionanilide, 2-amino-4-(4-propionyl-phenylthio)-butyranilide, 2-amino-4-(4-propionyl-phenylthio)-acetanilide, 2-amino-4-(4-acetylamino-phenylthio)-propionanilide, 2-amino-4-(4-acetylamino-phenylthio)-butyranilide, 2-amino-4-(4-acetylamino-phenylthio)-acetanilide, 2-amino-4-(4-methoxycarbonylamino-phenylthio)-propionanilide, 2-amino-4-(4-methoxycarbonylamino-phenylthio)-butyranilide, 2-amino-4-(4-methoxycarbonylamino-phenylthio)-acetanilide, 2-amino-4-(4-methoxycarbonyl-phenylthio)-propionanilide, 2-amino-4-(4-methoxycarbonyl-phenylthio)-butyranilide, 2-amino-4-(4-methoxycarbonyl-phenylthio)-acetanilide, 2-amino-4-(3,4-dimethyl-phenylthio)-propionanilide, 2-amino-4-(3,4-dimethyl-phenylthio)-butyranilide, 2-amino-4-(3,4-dimethyl-phenylthio)-acetanilide, 2-amino-4-(2-methyl-4-chloro-phenylthio)-propionanilide, 2-amino-4-(2-methyl-4-chloro-phenylthio)-butyranilide, 2-amino-4-(2-methyl-4-chloro-phenylthio)-acetanilide, 2-amino-4-(4-ethyl-phenylthio)-propionanilide, 2-amino-4-(4-ethyl-phenylthio)-butyranilide, 2-amino-4-(4-ethyl-phenylthio)-acetanilide, 2-amino-4-(3,4-dichloro-phenylthio)-propionanilide, 2-amino-4-(3,4-dichloro-phenylthio)-butyranilide, 2-amino-4-(3,4-dichloro-phenylthio)-acetanilide, 2-amino-4-(4-bromo-phenylthio)-propionanilide, 2-amino-4-(4-bromo-phenylthio)-butyranilide, 2-amino-4-(4-bromo-phenylthio)-acetanilide, 2-amino-4-(3,5-dimethyl-phenylthio)-propionanilide, 2-amino-4-(3,5-dimethyl-phenylthio)-butyranilide, 2-amino-4-(3,5-dimethyl-phenylthio)-acetanilide, 2-amino-4-(4-butyl-phenylthio)-propionanilide, 2-amino-4-(4-butyl-phenylthio)-butyranilide, 2-amino-4-(4-butyl-phenylthio)-acetanilide, 2-amino-4-(3-butyl-phenylthio)-propionanilide, 2-amino-4-(3-butyl-phenylthio)-butyranilide, 2-amino-4-(3-butyl-phenylthio)-acetanilide, 2-amino-5-phenylsulphinyl-acetanilide, 2-amino-5-phenylsulphinyl-propionanilide, 2-amino-5-phenylsulphinyl-butyranilide, 2-amino-5-phenylsulphinyl-iso-butyranilide, 2-amino-5-phenylsulphinyl-valeranilide, 2-amino-5-phenylsulphinyl-iso-valeranilide, 2-amino-5-phenylsulphinyl-caproanilide, 2-amino-5-phenylsulphinyl-iso-caproanilide, 2-amino-5-phenylsulphinyl-cyclopentanecarboxylic acid anilide, 2-amino-5-phenylsulphinyl-cyclohexanecarboxylic acid anilide, 2-amino-5-phenylsulphinyl-phenylacetanilide, 2-amino-5-phenylsulphinyl-phenoxyacetanilide, 2-amino-5-phenylsulphinyl-benzanilide, N-(2-amino-5-phenylsulphinyl-phenyl)-N'-methyl-urea, 2-amino-5-phenylsulphinyl-methoxyacetanilide, N-(2-amino-5-phenylsulphinyl-phenyl)-N'-butyl-urea, N-(2-amino-5-phenylsulphinyl-phenyl)-N'-ω-cyanopentyl-urea, N-(2-amino-5-phenylsulphinyl-phenyl)-N'-β-methoxyethyl-urea, N-(2-amino-5-phenylsulphinyl-phenyl)-N'-benzyl-urea, N-(2-amino-5-phenylsulphinyl-phenyl)-N'-phenyl-urea, 2-amino-5-(4-methyl-phenylsulphinyl)-propionanilide, 2-amino-5-(4-methyl-phenylsulphinyl)-butyranilide, 2-amino-5-(4-methyl-phenylsulphinyl)-acetanilide, 2-amino-5-(3-methyl-phenylsulphinyl)-propionanilide, 2-amino-5-(3-methyl-phenylsulphinyl)-butyranilide, 2-amino-5-(3-methyl-phenylsulphinyl)-acetanilide, 2-amino-5-(2-methyl-phenylsulphinyl)-propionanilide, 2-amino-5-(2-methyl-phenylsulphinyl)-butyranilide, 2-amino-5-(2-methyl-phenylsulphinyl)-acetanilide, 2-amino-5-(4-chloro-phenylsulphinyl)-propionanilide, 2-amino-5-(4-chloro-phenylsulphinyl)-butyranilide, 2-amino-5-(4-chloro-phenylsulphinyl)-acetanilide, 2-amino-5-(3-chloro-phenylsulphinyl)-propionanilide, 2-amino-5-(3-chloro-phenylsulphinyl)-butyranilide, 2-amino-5-(3-chloro-phenylsulphinyl-acetanilide, 2-amino-5-(2-chloro-phenylsulphinyl)-propionanilide, 2-amino-5-(2-chloro-phenylsulphinyl)-butyranilide, 2-amino-5-(2-chloro-phenylsulphinyl)-acetanilide, 2-amino-5-(4-methoxy-phenylsulphinyl)-propionanilide, 2-amino-5-(4-methoxy-phenylsulphinyl)-butyranilide, 2-amino-5-(4-methoxy-phenylsulphinyl)-acetanilide, 2-amino-5-(3-methoxy-phenylsulphinyl)-propionanilide, 2-amino-5-(3-methoxy-phenylsulphinyl)-butyranilide, 2-amino-5-(3-methoxy-phenylsulphinyl)-acetanilide, 2-amino-5-(4-methylthio-phenylsulphinyl)-propionanilide, 2-amino-5-(4-methylthio-phenylsulphinyl)-butyranilide, 2-amino-5-(4-methylthio-phenylsulphinyl)-acetanilide, 2-amino-5-(3-methylthio-phenylsulphinyl)-propionanilide, 2-amino-5-(3-methylthio-phenylsulphinyl)-butyranilide, 2-amino-5-(3-methylthio-phenylsulphinyl)-acetanilide, 2-amino-5-(4-cyano-phenylsulphinyl)-propionanilide, 2-amino-5-(4-cyano-phenylsulphinyl)-butyranilide, 2-amino-5-(4-cyano-phenylsulphinyl)-acetanilide, 2-amino-5-(3-cyano-phenylsulphinyl)-propionanilide, 2-amino-5-(3-cyano-phenylsulphinyl)-butyranilide, 2-amino-5-(3-cyano-phenylsulphinyl)-acetanilide, 2-amino-5-(4-acetyl-phenylsulphinyl)-propionanilide, 2-amino-5-(4-acetyl-phenylsulphinyl)-butyranilide, 2-amino-5-(4-acetyl-phenylsulphinyl)-acetanilide, 2-amino-5-(4-propionyl-phenylsulphinyl)-propionanilide, 2-amino-5-(4-propionyl-phenylsulphinyl)-butyranilide, 2-amino-5-(4-propionyl-phenylsulphinyl)-acetanilide, 2-amino-5-(4-acetylamino-phenylsulphinyl)-propionanilide, 2-amino-5-(4-acetylamino-phenylsulphinyl)-butyranilide, 2-amino-5-(4-acetylamino-phenylsulphinyl)-acetanilide, 2-amino-5-(4-methoxycarbonylamino-phenylsulphinyl)-propionanilide, 2-amino-5-(4-methoxycarbonylamino-phenylsulphinyl)-butyranilide, 2-amino-5-(4-methoxycarbonylamino-phenylsulphinyl)-acetanilide, 2-amino-5-(4-methoxycarbonyl-phenylsulphinyl)-propionanilide, 2-amino-5-(4-methoxycarbonyl-phenylsulphinyl)-butyranilide, 2-amino-5-(4-methoxycarbonyl-phenylsulphinyl)-acetanilide, 2-amino-5-(3,4-dimethyl-phenylsulphinyl)-propionanilide, 2-amino-5-(3,4-dimethyl-phenylsulphinyl)-butyranilide, 2-amino-5-(3,4-dimethyl-phenylsulphinyl)-acetanilide, 2-amino-5-(2-methyl-4-chloro-phenylsulphinyl)-propionanilide, 2-amino-5-(2-methyl-4-chloro-phenylsulphinyl)-butyranilide, 2-amino-5-(2-methyl-4-chloro-phenylsulphinyl)-acetanilide, 2-amino-5-(4-ethyl-phenylsulphinyl)-propionanilide, 2-amino-5-(4-ethyl-phenylsulphinyl)-butyranilide, 2-amino-5-(4-ethyl-phenylsulphinyl)-acetanilide, 2-amino-5-(3,4-dichloro-phenylsulphinyl)-propionanilide, 2-amino-5-(3,4-dichloro-phenylsulphinyl)-butyranilide, 2-amino-5-(3,4-dichloro-phenylsulphinyl)-acetanilide, 2-amino-5-(4-bromo-phenylsulphinyl)-propionanilide, 2-amino-5-(4-bromo-phenylsulphinyl)-butyranilide, 2-amino-5-(4-bromo-phenylsulphinyl)-acetanilide, 2-amino-5-(3,5-dimethyl-phenylsulphinyl)-propionanilide, 2-amino-5-(3,5-dimethyl-phenylsulphinyl)-butyrani-2-amino-5-(3,5-dimethyl-phenylsulphinyl)-acetanilide, 2-amino-5-(4-butyl-phenylsulphinyl)-propionanilide, 2-amino-5-(4-butyl-phenylsulphinyl)-butyranilide, 2-amino-5-(4-butyl-phenylsulphinyl)-acetanilide, 2-amino-5-(3-butyl-phenylsulphinyl)-propionanilide, 2-amino-5-(3-butyl-phenylsulphinyl)-butyranilide, 2-amino-5-(3-butyl-phenylsulphinyl)-acetanilide, 2-amino-4-phenylsulphinyl-acetanilide, 2-amino-4-phenylsulphinyl-propionanilide, 2-amino-4-phenylsulphinyl-butyranilide, 2-amino-4-phenylsulphinyl-iso-butyranilide, 2-amino-4-phenylsulphinyl-valeranilide, 2-amino-4-phenylsulphinyl-iso-valeranilide, 2-amino-4-phenylsulphinyl-caproanilide, 2-amino-4-phenylsulphinyl-iso-caproanilide, 2-amino-4-phenylsulphinyl-cyclopentanecarboxylic acid anilide, 2-amino-4-phenylsulphinyl-cyclohexanecarboxylic acid anilide, 2-amino-4-phenylsulphinyl-phenylacetanilide, 2-amino-4-phenylsulphinyl-phenoxyacetanilide, 2-amino-4-phenylsulphinyl-benzanilide, N-(2-amino-4-phenylsulphinyl-phenyl)-N'-methyl-urea, N-(2-amino-4-phenylsulphinyl-phenyl)-N'-ethyl-urea, N-(2-amino-4-phenylsulphinyl-phenyl)-N'-butyl-urea, N-(2-amino-4-phenylsulphinyl-phenyl)-N'-ω-cyanopentyl-urea, N-(2-amino-4-phenylsulphinyl-phenyl)-N'-β-methoxyethyl-urea, N-(2-amino-4-phenylsulphinyl-phenyl)-N'-benzyl-urea, N-(2-amino-4-phenylsulphinyl-phenyl)-N'-phenyl-urea, 2-amino-4-(4-methyl-phenylsulphinyl)-propionanilide, 2-amino-4-(4-methyl-phenylsulphinyl)-butyranilide, 2-amino-4-(4-methyl-phenylsulphinyl)-acetanilide, 2-amino-4-(3-methyl-phenylsulphinyl)-propionanilide, 2-amino-4-(3-methyl-phenylsulphinyl)-butyranilide, 2-amino-4-(3-methyl-phenylsulphinyl)-acetanilide, 2-amino-4-(2-methyl-phenylsulphinyl)-propionanilide, 2-amino-4-(2-methyl-phenylsulphinyl)-butyranilide, 2-amino-4-(2-methyl-phenylsulphinyl)-acetanilide, 2-amino-4-(4-chloro-phenylsulphinyl)-propionanilide, 2-amino-4-(4-chloro-phenylsulphinyl)-butyranilide, 2-amino-4-(4-chloro-phenylsulphinyl)-acetanilide, 2-amino-4-(3-chloro-phenylsulphinyl)-propionanilide, 2-amino-4-(3-chloro-phenylsulphinyl)-butyranilide, 2-amino-4-(3-chloro-phenylsulphinyl)-acetanilide, 2-amino-4-(2-chloro-phenylsulphinyl)-propionanilide, 2-amino-4-(2-chloro-phenylsulphinyl)-butyranilide, 2-amino-4-(2-chloro-phenylsulphinyl)-acetanilide, 2-amino-4-(4-methoxy-phenylsulphinyl)-propionanilide, 2-amino-4-(4-methoxy-phenylsulphinyl)-butyranilide, 2-amino-4-(4-methoxy-phenylsulphinyl)-acetanilide, 2-amino-4-(3-methoxy-phenylsulphinyl)-propionanilide, 2-amino-4-(3-methoxy-phenylsulphinyl)-butyranilide, 2-amino-4-(3-methoxy-phenylsulphinyl)-acetanilide, 2-amino-4-(4-methylthio-phenylsulphinyl)-propionanilide, 2-amino-4-(4-methylthio-phenylsulphinyl)-butyranilide, 2-amino-4-(4-methylthio-phenylsulphinyl)-acetanilide, 2-amino-4-(3-methylthio-phenylsulphinyl)-propionanilide, 2-amino-4-(3-methylthio-phenylsulphinyl)-butyranilide, 2-amino-4-(3-methylthio-phenylsulphinyl)-acetanilide, 2-amino-4-(4-cyano-phenylsulphinyl)-propionanilide, 2-amino-4-(4-cyano-phenylsulphinyl)-butyranilide, 2-amino-4-(4-cyano-phenylsulphinyl)-acetanilide, 2-amino-4-(3-cyano-phenylsulphinyl)-propionanilide, 2-amino-4-(3-cyano-phenylsulphinyl)-butyranilide, 2-amino-4-(3-cyano-phenylsulphinyl)-acetanilide, 2-amino-4-(4-acetyl-phenylsulphinyl)-propionanilide, 2-amino-4-(4-acetyl-phenylsulphinyl)-butyranilide, 2-amino-4-(4-acetyl-phenylsulphinyl)-acetanilide, 2-amino-4-(4-propionyl-phenylsulphinyl)-propionanilide, 2-amino-4-(4-propionyl-phenylsulphinyl)-butyranilide, 2-amino-4-(4-propionyl-phenylsulphinyl)-acetanilide, 2-amino-4-(4-acetylamino-phenylsulphinyl)-propionanilide, 2-amino-4-(4-acetylamino-phenylsulphinyl)-butyranilide, 2-amino-4-(4-acetylamino-phenylsulphinyl)-acetanilide, 2-amino-4-(4-methoxycarbonylamino-phenylsulphinyl)-propionanilide, 2-amino-4-(4-methoxycarbonylamino-phenylsulphinyl)-butyranilide, 2-amino-4-(4-methoxycarbonylamino-phenylsulphinyl)-acetanilide, 2-amino-4-(4-methoxycarbonyl-phenylsulphinyl)-propionanilide, 2-amino-4-(4-methoxycarbonyl-phenylsulphinyl)-butyranilide, 2-amino-4-(4-methoxycarbonyl-phenylsulphinyl)-acetanilide, 2-amino-4-(3,4-dimethyl-phenylsulphinyl)-propionanilide, 2-amino-4-(3,4-dimethyl-phenylsulphinyl)-butyranilide, 2-amino-4-(3,4-dimethyl-phenylsulphinyl)-acetanilide, 2-amino-4-(2-methyl-4-chloro-phenylsulphinyl)-propionanilide, 2-amino-4-(2-methyl-4-chloro-phenylsulphinyl)-butyranilide, 2-amino-4-(2-methyl-4-chloro-phenylsulphinyl)-acetanilide, 2-amino-4-(4-ethyl-phenylsulphinyl)-propionanilide, 2-amino-4-(4-ethyl-phenylsulphinyl)-butyranilide, 2-amino-4-(4-ethyl-phenylsulphinyl)-acetanilide, 2-amino-4-(3,4-dichloro-phenylsulphinyl)-propionanilide, 2-amino-4-(3,4-dichloro-phenylsulphinyl)-butyranilide, 2-amino-4-(3,4-dichloro-phenylsulphinyl)-acetanilide, 2-amino-4-(4-bromo-phenylsulphinyl)-propionanilide, 2-amino-4-(4-bromo-phenylsulphinyl)-butyranilide, 2-amino-4-(4-bromo-phenylsulphinyl)-acetanilide, 2-amino-4-(3,5-dimethyl-phenylsulphinyl)-propionanilide, 2-amino-4-(3,5-dimethyl-phenylsulphinyl)-butyranilide, 2-amino-4-(3,5-dimethyl-phenylsulphinyl)-acetanilide, 2-amino-4-(4-butyl-phenylsulphinyl)-propionanilide, 2-amino-4-(4-butyl-phenylsulphinyl)-butyranilide, 2-amino-4-(4-butyl-phenylsulphinyl)-acetanilide, 2-amino-4-(3-butyl-phenylsulphinyl)-propionanilide, 2-amino-4-(3-butyl-phenylsulphinyl)-butyranilide, 2-amino-4-(3-butyl-phenylsulphinyl)-acetanilide, 2-amino-5-phenylsulphonyl-acetanilide, 2-amino-5-phenylsulphonyl-propionanilide, 2-amino-5-phenylsulphonyl-butyranilide, 2-amino-5-phenylsulphonyl-iso-butyranilide, 2-amino-5-phenylsulphonyl-valeranilide, 2-amino-5-phenylsulphonyl-iso-valeranilide, 2-amino-5-phenylsulphonyl-caproanilide, 2-amino-5-phenylsulphonyl-iso-caproanilide, 2-amino-5-phenylsulphonyl-cyclopentanecarboxylic acid anilide, 2-amino-5-phenylsulphonyl-cyclohexanecarboxylic acid anilide, 2-amino-5-phenylsulphonyl-phenylacetanilide, 2-amino-5-phenylsulphonyl-phenoxyacetanilide, 2-amino-5-phenylsulphonyl-benzanilide, N-(2-amino-5-phenylsulphonyl-phenyl)-N'-methyl-urea, N-(2-amino-5-phenylsulphonyl-phenyl)-N'-ethyl-urea, N-(2-amino-5-phenylsulphonyl-phenyl)-N'-butyl-urea, N-(2-amino-5-phenylsulphonyl-phenyl)-N'-ω-cyanopentyl-urea, N-(2-amino-5-phenylsulphonyl-phenyl)-N'-β-methoxyethyl-urea, N-(2-amino-5-phenylsulphonyl-phenyl)-N'-benzyl-urea, N-(2-amino-5-phenylsulphonyl-phenyl)-N'-phenyl-urea, 2-amino-5-(4-methyl-phenylsulphonyl)-propionanilide, 2-amino-5-(4-methyl-phenylsulphonyl)-butyranilide, 2-amino-5-(4-methyl-phenylsulphonyl)-acetanilide, 2-amino-5-(3-methyl-phenylsulphonyl)-propionanilide, 2-amino-5-(3-methyl-phenylsulphonyl)-butyranilide, 2-amino-5-(3-methyl-phenylsulphonyl)-acetanilide, 2-amino-5-(2-methyl-phenylsulphonyl)-propionanilide, 2-amino-5-(2-methyl-phenylsulphonyl)-butyranilide, 2-amino-5-(2-methyl-phenylsulphonyl)-acetanilide, 2-amino-5-(4-chloro-phenylsulphonyl)-propionanilide, 2-amino-5-(4-chloro-phenylsulphonyl)-butyranilide, 2-amino-5-(4-chloro-phenylsulphonyl)-acetanilide, 2-amino-5-(3-chloro-phenylsulphonyl)-propionanilide, 2-amino-5-(3-chloro-phenylsulphonyl)-butyranilide, 2-amino-5-(3-chloro-phenylsulphonyl)-acetanilide, 2-amino-5-(2-chloro-phenylsulphonyl)-propionanilide, 2-amino-5-(2-chloro-phenysulphonyl)-butyranilide, 2-amino-5-(2-chloro-phenylsulphonyl)-acetanilide, 2-amino-5-(4-methoxy-phenylsulphonyl)-propionanilide, 2-amino-5-(4-methoxy-phenylsulphonyl)-butyranilide, 2-amino-5-(4-methoxy-phenylsulphonyl)-acetanilide, 2-amino-5-(3-methoxy-phenylsulphonyl)-propionanilide, 2-amino-5-(3-methoxy-phenylsulphonyl)-butyranilide, 2-amino-5-(3-methoxy-phenylsulphonyl)-acetanilide, 2-amino-5-(4-methylthio-phenylsulphonyl)-propionanilide, 2-amino-5-(4-methylthio-phenylsulphonyl)-butyranilide, 2-amino-5-(4-methylthio-phenylsulphonyl)-acetanilide, 2-amino-5-(3-methylthio-phenylsulphonyl)-propionanilide, 2-amino-5-(3-methylthio-phenylsulphonyl)-butyranilide, 2-amino-5-(3-methylthio-phenylsulphonyl)-acetanilide, 2-amino-5-(4-cyano-phenylsulphonyl)-propionanilide, 2-amino-5-(4-cyano-phenylsulphonyl)-butyranilide, 2-amino-5-(4-cyano-phenylsulphonyl)-acetanilide, 2-amino-5-(3-cyano-phenylsulphonyl)-propionanilide, 2-amino-5-(3-cyano-phenylsulphonyl)-butyranilide, 2-amino-5-(3-cyano-phenylsulphonyl)-acetanilide, 2-amino-5-(4-acetyl-phenylsulphonyl)-propionanilide, 2-amino-5-(4-acetyl-phenylsulphonyl)-butyranilide, 2-amino-5-(4-acetyl-phenylsulphonyl)-acetanilide, 2-amino-5-(4-propionyl-phenylsulphonyl)-propionanilide, 2-amino-5-(4-propionyl-phenylsulphonyl)-butyranilide, 2-amino-5-(4-propionyl-phenylsulphonyl)-acetanilide, 2-amino-5-(4-acetylamino-phenylsulphonyl)-propionanilide, 2-amino-5-(4-acetylamino-phenylsulphonyl)-butyranilide, 2-amino-5-(4-acetylamino-phenylsulphonyl)-acetanilide, 2-amino-5-(4-methoxycarbonylamino-phenylsulphonyl)-propionanilide, 2-amino-5-(4-methoxycarbonylamino-phenylsulphonyl)-butyranilide, 2-amino-5-(4-methoxycarbonylamino-phenylsulphonyl)-acetanilide, 2-amino-5-(4-methoxycarbonyl-phenylsulphonyl)-propionanilide, 2-amino-5-(4-methoxycarbonyl-phenylsulphonyl)-butyranilide, 2-amino-5-(4-methoxycarbonyl-phenylsulphonyl)-acetanilide, 2-amino-5-(3,4-dimethyl-phenylsulphonyl)-propionanilide, 2-amino-5-(3,4-dimethyl-phenylsulphonyl)-butyranilide, 2-amino-5-(3,4-dimethyl-phenylsulphonyl)-acetanilide, 2-amino-5-(2-methyl-4-chloro-phenylsulphonyl)-acetanilide, 2-amino-5-(2-methyl-4-chloro-phenylsulphonyl)-propionanilide, 2-amino-5-(2-methyl-4-chloro-phenylsulphonyl)-butyranilide, 2-amino-5-(2-methyl-4-chloro-phenylsulphonyl)-acetanilide, 2-amino-5-(4-ethyl-phenylsulphonyl)-propionanilide, 2-amino-5-(4-ethyl-phenylsulphonyl)-butyranilide, 2-amino-5-(4-ethyl-phenylsulphonyl)-acetanilide, 2-amino-5-(3,4-dichloro-phenylsulphonyl)-propionanilide, 2-amino-5-(3,4-dichloro-phenylsulphonyl)-butyranilide, 2-amino-5-(3,4-dichloro-phenylsulphonyl)-acetanilide, 2-amino-5-(4-bromo-phenylsulphonyl)-proplonanilide, 2-amino-5-(4-bromo-phenylsulphonyl)-butyranilide, 2-amino-5-(4-bromo-phenylsulphonyl)-acetanilide, 2-amino-5-(3,5-dimethyl-phenylsulphonyl)-propionanilide, 2-amino-5-(3,5-dimethyl-phenylsulphonyl)-butyranilide, 2-amino-5-(3,5-dimethyl-phenylsulphonyl)-acetanilide, 2-amino-5-(4-butyl-phenylsulphonyl)-propionanilide, 2-amino-5-(4-butyl-phenylsulphonyl)-butyranilide, 2-amino-5-(4-butylphenylsulphonyl)-acetanilide, 2-amino-5-(3-butyl-phenylsulphonyl)-propionanilide, 2-amino-5-(3-butyl-phenylsulphonyl)-butyranilide, 2-amino-5-(3-butyl-phenylsulphonyl)-acetanilide, 2-amino-4-phenylsulphonyl-acetanilide, 2-amino-4-phenylsulphonyl-propionanilide, 2-amino-4-phenylsulphonyl-butyranilide, 2-amino-4-phenylsulphonyl-iso-butyranilide, 2-amino-4-phenylsulphonyl-valeranilide, 2-amino-4-phenylsulphonyl-isovaleranilide, 2-amino-4-phenylsulphonyl-caproanilide, 2-amino-4-phenylsulphonyl-iso-caproanilide, 2-amino-4-phenylsulphonyl-cyclopentanecarboxylic acid anilide, 2-amino-4-phenylsulphonyl-cyclohexanecarboxylic acid anilide, 2-amino-4-phenylsulphonyl-phenylacetanilide, 2-amino-4-phenylsulphonyl-phenoxyacetanilide, 2-amino-4-phenylsulphonyl-benzanilide, N-(2-amino-4-phenylsulphonyl-phenyl)-N'-methyl-urea, N-(2-amino-4-phenylsulphonyl-phenyl)-N'-ethyl-urea, N-(2-amino-4-phenylsulphonyl-phenyl)-N'-butyl-urea, N-(2-amino-4-phenylsulphonyl-phenyl)-N-'-ω-cyanopentyl-urea, N-(2-amino-4-phenylsulphonyl-phenyl)-N'-β-methoxyethyl-urea, N-(2-amino-4-phenylsulphonyl-phenyl)-N'-benzyl-urea, N-(2-amino-4-phenylsulphonyl-phenyl)-N'-phenyl-urea, 2-amino-4-(4-methyl-phenylsulphonyl)-propionanilide, 2-amino-4-(4-methyl-phenylsulphonyl)-butyranilide, 2-amino-4-(4-methyl-phenylsulphonyl)-acetanilide, 2-amino-4-(3-methyl-phenylsulphonyl)-propionanilide, 2-amino-4-(3-methyl-phenylsulphonyl)-butyranilide, 2-amino-4-(3-methyl-phenylsulphonyl)-acetailide, 2-amino-4-(2-methyl-phenylsulphonyl)-propionanilide, 2-amino-4-(2-methyl-phenylsulphonyl)-butyranilide, 2-amino-4-(2-methyl-phenylsulphonyl)-acetanilide, 2-amino-4-(4-chloro-phenylsulphonyl)-propionanilide, 2-amino-4-(4-chloro-phenylsulphonyl)-butyranilide, 2-amino-4-(4-chloro-phenylsulphonyl)-acetanilide, 2-amino-4-(3-chloro-phenylsulphonyl)-propionanilide, 2-amino-4-(3-chloro-phenylsulphonyl)-butyranilide, 2-amino-4-(3-chloro-phenylsulphonyl)-acetanilide, 2-amino-4-(2-chloro-phenylsulphonyl)-propionanilide, 2-amino-4-(2-chloro-phenylsulphonyl)-butyranilide, 2-amino-4-(2-chloro-phenylsulphonyl)-acetanilide, 2-amino-4-(4-methoxy-phenylsulphonyl)-propionanilide, 2-amino-4-(4-methoxy-phenylsulphonyl)-butyranilide, 2-amino-4-(4-methoxy-phenylsulphonyl)-acetanilide 2-amino-4-(3-methoxy-phenylsulphonyl)-propionanilide, 2-amino-4-(3-methoxy-phenylsulphonyl)-butyranilide, 2-amino-4-(3-methoxy-phenylsulphonyl)-acetanilide, 2-amino- 4-(4-methylthio-phenylsulphonyl)-propionanilide, 2-amino-4-(4-methylthio-phenylsulphonyl)-butyranilide, 2-amino-4-(4-methylthio-phenylsulphonyl)-acetanilide, 2-amino-4-(3-methylthio-phenylsulphonyl)-propionanilide, 2-amino-4-(3-methylthio-phenylsulphonyl)-butyranilide, 2-amino-4-(3-methylthio-phenylsulphonyl)-acetanilide, 2-amino-4-(4-cyano-phenylsulphonyl)-propionanilide, 2-amino-4-(4-cyano-phenylsulphonyl)-butyranilide, 2-amino-4-(4-cyano-phenylsulphonyl)-acetanilide, 2-amino-4-(3-cyano-phenylsulphonyl)-propionanilide, 2-amino-4-(3-cyano-phenylsulphonyl)-butyranilide, 2-amino-4-(3-cyano-phenylsulphonyl)-acetanilide, 2-amino-4-(4-acetyl-phenylsulphonyl)-propionanilide, 2-amino-4-(4-acetyl-phenylsulphonyl)-butyranilide, 2-amino-4-(4-acetyl-phenylsulphonyl)-acetanilide, 2-amino-4-(4-propionyl-phenylsulphonyl)-propionanilide, 2-amino-4-(4-propionyl-phenylsulphonyl)-butyranilide, 2-amino-4-(4-propionayl-phenylsulphonyl)-acetanilide, 2-amino-4-(4-acetylamino-phenylsulphonyl)-propionanilide, 2-amino-4-(4-acetylamino-phenylsulphonyl)-butyranilide, 2-amino-4-(4-acetylamino-phenylsulphonyl)-acetanilide, 2-amino-4-(4-methoxycarbonylamino-phenylsulphonyl)-propionanilide, 2-amino-4-(4-methoxycarbonylamino-phenylsulphonyl)-butyranilide, 2-amino-4-(4-methoxycarbonylamino-phenylsulphonyl)-acetanilide, 2-amino-4-(4-methoxycarbonyl-phenylsulphonyl)-propionanilide, 2-amino-4-(4-methoxycarbonyl-phenylsulphonyl)-butyranilide, 2-amino-4-(4-methoxycarbonyl-phenylsulphonyl)-acetanilide, 2-amino-4-(3,4-dimethyl-phenylsulphonyl)-propionanilide, 2-amino-4-(3,4-dimethyl-phenylsulphonyl)-butyranilide, 2-amino-4-(3,4-dimethyl-phenylsulphonyl)-acetanilide, 2-amino-4-(2-methyl-4-chloro-phenylsulphonyl)-propionanilide, 2-amino-4-(2-methyl-4-chloro-phenylsulphonyl)-butyranilide, 2-amino-4-(2-methyl-4-chloro-phenylsulphonyl)-acetanilide, 2-amino-4-( 4-ethyl-phenylsulphonyl)-propionanilide, 2-amino-4-(4-ethyl-phenylsulphonyl)-butyranilide, 2-amino-4-(4-ethyl-phenylsulphonyl)-acetanilide, 2-amino-4-(3,4-dichloro-phenylsulphonyl)-propionanilide, 2-amino-4-(3,4-dichloro-phenylsulphonyl)-butyranilide, 2-amino-4-(3,4-dichloro-phenylsulphonyl)-acetanilide, 2-amino-4-(4-bromo-phenylsulphonyl)-propionanilide, 2-amino-4-(4-bromo-phenylsulphonyl)-butyranilide, 2-amino-4-(4-bromo-phenylsulphonyl)-acetanilide, 2-amino-4-(3,5-dimethyl-phenylsulphonyl)-propionanilide, 2-amino-4-(3,5-dimethyl-phenylsulphonyl)-butyranilide, 2-amino-4-(3,5-dimethyl-phenylsulphonyl)-acetanilide, 2-amino-4-(4-butyl-phenylsulphonyl)-propionanilide, 2-amino-4-(4-butyl-phenylsulphonyl)-butyranilide, 2-amino-4-(4-butyl-phenylsulphonyl)-acetanilide, 2-amino-4-(3-butyl-phenylsulphonyl)-propionanilide, 2-amino-4-(3-butyl-phenylsulphonyl)-butyranilide and 2-amino-4-(3-butyl-phenylsulphonyl)-acetanilide.

The following may be mentioned individually as new active compounds: N-(2-acetamido-4-phenoxy-phenyl)-N'-methoxycarbonyl-N''-propionyl-guanidine, N-(2-acetamido-4-phenoxyphenyl)-N'-ethoxycarbonyl-N''-propionyl-guanidine, N-(2-acetamido-4-phenoxyphenyl)-N'-iso-propoxycarbonyl-N''-propionylguanidine, N-(2-acetamido-4-phenoxy-phenyl)-N'-sec.-butoxycarbonyl-N''-propionyl-guanidine, N-(2-propionamido-4-phenoxyphenyl)-N'-methoxycarbonyl-N''-propionyl-guanidine, N-(2-butyramido-4-phenoxyphenyl)-N'-methoxycarbonyl-N''-propionyl-guanidine, N-(2-valeramido-4-phenoxy-phenyl)-N'-methoxycarbonyl-N''-propionyl-guanidine, N-(2-cyclopentanecarboxylic acid amido-4-phenoxy-phenyl)-N'-methoxycarbonyl-N''-propionyl-guanidine, N-(2-cyclohexanecarboxylic acid amido-4-phenoxy-phenyl)-N'-methoxycarbonyl-N''-propionyl-guanidine, N-(2-benzamido-4-phenoxy-phenyl)-N'-methoxycarbonyl-N''-propionyl-guanidine, N-(2-acetamido-4-phenoxy-phenyl)-N'-methoxycarbonyl-N''-acetylguanidine, N-(2-acetamido-4-phenoxy-phenyl)-N'-methoxycarbonyl-N''-butyryl-guanidine, N-(2-acetamido-4-phenoxy-phenyl)-N'-methoxycarbonyl-N''-cyclohexanecarbonyl-guanidine, N-(2-acetamido-4-phenoxy-phenyl)-N'-methoxycarbonyl-N''-benzoyl-guanidine, N-(2-acetamido-4-phenoxyphenyl)-N'-methoxycarbonyl-N''-phenylacetyl-guanidine, N-(2-acetamido-4-phenoxy-phenyl)-N'-methoxycarbonyl-N''-phenoxyacetyl-guanidine, N-[2-(2'-methylureido)-4-phenoxy-phenyl]-N'-methoxycarbonyl-N''-propionylguanidine, N-[2-(2'-ethylureido)-4-phenoxy-phenyl]-N'-methoxycarbonyl-N''propionyl-guanidine, N-[2-(2'-butylureido)-4-phenoxy-phenyl]-N'-methoxycarbonyl-N''-propionyl-guanidine, N-[2-(2'-ω-cyanopentylureido)-4-phenoxy-phenyl]-N'-methoxycarbonyl-N''-propionyl-guanidine, N-[2-(2'-β-methoxymethylureido)-4-phenoxy-phenyl]-N'-methoxycarbonyl-N''-propionyl-guanidine, N-[2-(2'-benzylureido)-4-phenoxy-phenyl]-N'-methoxycarbonyl-N''-propionyl-guanidine, N-[2-(2'-phenylureido)-4-phenoxy-phenyl]-N'-methoxycarbonyl-N''-propionyl-guanidine, N-(2-acetamido-4-phenoxy-phenyl)-N',N''-bis-methoxycarbonyl-guanidine, N-(2-acetamido-4-phenoxy-phenyl)-

N',N''-bis-ethoxycarbonyl-guanidine, N-(2-acetamido-4-phenoxy-phenyl)-N',N''-bis-iso-propoxycarbonyl-guanidine, N-(2-acetamido-4-phenoxy-phenyl)-N',N''-bis-sec.-butoxycarbonyl-guanidine, N-(2-propionamido-4-phenoxy-phenyl)-N',N''-bis-methoxycarbonyl-guanidine, N-(2-butyramido-4-phenoxy-phenyl)-N',N''-bis-methoxycarbonyl-guanidine, N-(2-iso-butyramido-4-phenoxy-phenyl)-N',N''-bis-methoxycarbonyl-guanidine, N-(2-valeramido-4-phenoxy-phenyl)-N',N''-bis-methoxycarbonyl-guanidine N-(2-iso-valeramido-4-phenoxyphenyl)-N',N''-bis-methoxycarbonyl-guanidine, N-(2-caproamido-4-phenoxy-phenyl)-N',N''-bis-methoxycarbonyl-guanidine, N-(2-iso-caproamido-4-phenoxy-phenyl)-N',N''-bis-methoxycarbonyl-guanidine, N-(2-cyclopentanecarboxylic acid amido-4-phenoxy-phenyl)-N',N''-bis-methoxycarbonyl-guanidine, N-(2-cyclohexanecarboxylic acid amido-4-phenoxy-phenyl)-N',N''-bis-methoxycarbonyl-guanidine, N-(2-phenylacetamido-4-phenoxy-phenyl)-N',N''-bis-methoxycarbonyl-guanidine, N-(2-phenoxyacetamido-4-phenoxy-phenyl)-N',N''-bis-methoxycarbonyl-guanidine, N-(2-benzamido-4-phenoxy-phenyl)-N',N''-bis-methoxycarbonyl-guanidine, N-[2-(2'-methylureido)-4-phenoxy-phenyl]-N',N''-bis-methoxycarbonyl-guanidine, N-[2-(2'-ethylureido)-4-phenoxy-phenyl]-N',N''-bis-methoxycarbonyl-guanidine, N-[2-(2'-butylureido)-4-phenoxy-phenyl]-N',N''-bis-methoxycarbonyl-guanidine, N-[2-(2'-ω-cyanopentylureido)-4-phenoxy-phenyl]-N',N''-bis-methoxycarbonyl-guanidine, N-[2-(2'-β-methoxyethyl-ureido)-4-phenoxy-phenyl]-N',N''-bis-methoxycarbonyl-guanidine, N-[2-(2'-benzylureido)-4-phenoxy-phenyl]-N',N''-bis-methoxycarbonyl-guanidine, N-[2-(2'-phenylureido)-4-phenoxy-phenyl]-N',N''-bis-methoxycarbonyl-guanidine, N-[2-propionamido-4-(4-methyl-phenoxy)-phenyl]-N',N''-bis-methoxycarbonyl-guanidine, N-[2-propionamido-4-(3-methyl-phenoxy)-phenyl]-N',N''-bis-methoxycarbonyl-guanidine, N-[2-propionamido-4-(4-chloro-phenoxy)-phenyl]-N',N''-bis-methoxycarbonyl-guanidine, N-[2-propionamido-4-(3-chloro-phenoxy)-phenyl]-N',N''-bis-methoxycarbonyl-guanidine, N-[2-propionamido-4-(2-chloro-phenoxy)-phenyl]-N',N''-bis-methoxycarbonyl-guanidine, N-[2-propionamido-4-(4-methoxy-phenoxy)-phenyl]-N',N''-bis-methoxycarbonyl-guanidine, N-[2-propionamido-4-(3-methoxy-phenoxy)-phenyl]-N',N''-bis-methoxycarbonyl-guanidine, N-[2-propionamido-4-(4-methylthio-phenoxy)-phenyl]-N',N''-bis-methoxycarbonyl-guanidine, N-[2-propionamido-4-(3-methylthio-phenoxy)-phenyl]-N',N''-bis-methoxycarbonyl-guanidine, N-[2-propionamido-4-(4-cyano-phenoxy)-phenyl]-N',N''-bis-methoxycarbonyl-guanidine, N-[2-propionamido-4-(4-acetyl-phenoxy)-phenyl]-N',N''-bis-methoxycarbonyl-guanidine, N-[2-propionamido-4-(3-cyano-phenoxy)-phenyl]-N',N''-bis-methoxy-carbonyl-guanidine, N-[2-propionamido-4-(4-propionyl-phenoxy)-phenyl]-N',N''-bis-methoxycarbonyl-guanidine, N-[2-propionamido-4-(4-acetylamino-phenoxy)-phenyl]-N',N''-bis-methoxycarbonyl-guanidine, N-[2-propionamido-4-(4-methoxycarbonyl-phenoxy)-phenyl]-N',N''-bis-methoxycarbonyl-guanidine, N-[2-propionamido-4-(3,4-dimethyl-phenoxy)-phenyl]-N',N''-bis-methoxycarbonyl-guanidine, N-[2-propionamido-4-(3,4-dichloro-phenoxy)-phenyl]-N',N''-bis-methoxycarbonyl-guanidine, N-(2-acetamido-4-phenoxy-phenyl)-N'-methoxycarbonyl-N''-propionyl-guanidine, N-(2-acetamido-5-phenoxyphenyl)-N'-ethoxycarbonyl-N''-propionyl-guanidine, N-(2-acetamido-5-phenoxy-phenyl)-N'-iso-propoxycarbonyl-N''-propionyl-guanidine, N-(2-acetamido-5-phenoxy-phenyl)-N'-sec.-butoxycarbonyl-N''-propionyl-guanidine, N-(2-propionamido-5-phenoxy-phenyl)-N'-methoxycarbonyl-N''-propionyl-guanidine, N-(2-butyramido-5-phenoxy-phenyl)-N'-methoxycarbonyl-N''-propionyl-guanidine, N-(2-valeramido-5-phenoxy-phenyl)-N'-methoxycarbonyl-N''-propionyl-guanidine, N-(2-cyclopentanecarboxylic acid amido-5-phenoxy-phenyl)-N'-methoxy-carbonyl-N''-propionyl-guanidine, N-(2-cyclohexanecarboxylic acid amido-5-phenoxy-phenyl)-N'-methoxycarbonyl-N''-propionyl-guanidine, N-(2-benzamido-5-phenoxy-phenyl)-N'-methoxycarbonyl-N''-propionyl-guanidine, N-(2-acetamido-5-phenoxy-phenyl)-N'-methoxycarbonyl-N''-acetyl-guanidine, N-(2-acetamido-5-phenoxy-phenyl)-N'-methoxycarbonyl-N''-butyryl-guanidine, N-(2-acetamido-5-phenoxy-phenyl)-N'-methoxycarbonyl-N''-cyclohexanecarbonyl-guanidine, N-(2-acetamido-5-phenoxy-phenyl)-N'-methoxycarbonyl-N''-benzoyl-guanidine, N-(2-acetamido-5-phenoxy-phenyl)-N'-methoxycarbonyl-N''-phenylacetyl-guanidine, N-(2-acetamido-5-phenoxy-phenyl)-N'-methoxycarbonyl-N''-phenoxyacetyl-guanidine, N-[2-(2'-methylureido)-5-phenoxy-phenyl]-N'-methoxycarbonyl-N''-propionyl-guanidine, N-[2-(2'-ethylureido)-5-phenoxy-phenyl]-N'-methoxycarbonyl-N''-propionyl-guanidine, N-[2-(2'-butylureido)-5-phenoxy-phenyl]-N'-methoxycarbonyl-N''-propionyl-guanidine, N-[2-(2'-ω-cyanopentylureido)-5-phenoxy-phenyl]-N'methoxycarbonyl-N''-propionyl-guanidine, N-[2-(2'-β-methoxymethylureido)-5-phenoxy-phenyl]-N'-methoxycarbonyl-N''-propionyl-guanidine, N-[2-(2'-benzylureido)-5-phenoxy-phenyl]-N'-methoxycarbonyl-N''-propionyl-guanidine, N-[2-(2-phenylureido)-5-phenoxy-phenyl]-N'-methoxycarbonyl-N''-propionyl-guanidine, N-(2-acetamido-5-phenoxy-phenyl)-N',N''-bis-methoxycarbonyl-guanidine, N-(2-acetamido-5-phenoxy-phenyl)-N',N''-bis-ethoxycarbonyl-guanidine, N-(2-acetamido-5-phenoxy-phenyl)-N',N''-bis-iso-propoxycarbonyl-guanidine, N-(2-acetamido-5-phenoxy-phenyl)-N',N''-bis-sec.-butoxycarbonyl-guanidine, N-(2-propionamido-5-phenoxy-phenyl)-N',N''-bis-methoxycarbonyl-guanidine, N-(2-butyramido-5-phenoxy-phenyl)-N',N''-bis-methoxycarbonyl-guanidine, N-(2-iso-butyramido-5-phenoxy-phenyl)-N',N''-bis-methoxycarbonyl-guanidine, N-(2-valeramido-5-phenoxy-phenyl)-N',N''-bis-methoxycarbonyl-guanidine, N-(2-iso-valeramido-5-phenoxyphenyl)-N',N''-bis-methoxycarbonyl-guanidine, N-(2-caproamido-5-phenoxy-phenyl)-N',N''-bis-methoxycarbonyl-guanidine, N-(2-iso-caproamido-5-phenoxy-phenyl)-N',N''-bis-methoxycarbonyl-guanidine, N-(2-cyclopentanecarboxylic acid amino-5-phenoxy-phenyl)-N',N''-bis-methoxycarbonyl-guanidine, N-(2-cyclohexanecarboxylic acid amino-5-phenoxy-phenyl)-N',N''-bis-methoxycarbonyl-guanidine, N-(2-phenylacetamido-5-phenoxyphenyl)-N',N''-bis-methoxycarbonyl-guanidine, N-(2-phenoxyacetamido-5-phenoxy-phenyl)-N',N''-bis-methoxycarbonyl-guanidine, N-(2-benzamido-5-phenoxy-phenyl)-N',N''-bis-methoxycarbonyl-guanidine, N-[2-(2'-methylureido)-5-phenoxy-phenyl]-N',N''-bis-methoxycarbonyl-guanidine, N-[2-(2'-ethylureido)-5-phenoxy-phenyl]-N',N''-bis-methoxycarbonyl-guanidine, N-[2-(2'-butylureido)-5-phenoxy-phenyl]-N',N''-bis-methoxycarbonyl-guanidine, N-[2-(2'-ω-cyanopentylureido)-5-phenoxy-phenyl]-N',N''-bis-methoxycarbonyl-guanidine, N-[2-(2'-β-methoxyethylureido)-5-phenoxy-phenyl]-N',N''-bis-methoxycarbonyl-guanidine, N-[2-

(2'-benzylureido)-5-phenoxy-phenyl]-N',N''-bis-methoxycarbonyl-guanidine, N-[2-(2'-phenylureido)-5-phenoxy-phenyl]-N',N''-bis-methoxycarbonyl-guanidine, N-[2-propionamido-5-(4-methyl-phenoxy)-phenyl]-N',N''-bis-methoxycarbonyl-guanidine, N-[2-propionamido-5-(3-methyl-phenoxy)-phenyl]-N',N''-bis-methoxycarbonyl-guanidine, N-[2-propionamido-5-(4-chlorophenoxy)-phenyl]-N',N''-bis-methoxycarbonyl-guanidine, N-[2-propionamido-5-(3-chloro-phenoxy)-phenyl]-N',N''-bis-methoxycarbonyl-guanidine, N-[2-propionamido-5-(2-chloro-phenoxy)-phenyl]-N',N''-bis-methoxycarbonyl-guanidine, N-[2-propionamido-5-(4-methoxy-phenoxy)-phenyl]-N',N''-bis-methoxycarbonyl-guanidine, N-[2-propionamido-5-(4-methylthio-phenoxy)-phenyl]-N',N''-bis-methoxycarbonyl-guanidine, N-[2-propionamido-5-(3-methylthio-phenoxy)-phenyl]-N',N''-bis-methoxycarbonyl-guanidine, N-[2-propionamido-5-(4-cyano-phenoxy)-phenyl]-N',N''-bis-methoxycarbonyl-guanidine, N-[2-propionamido-5-(4-acetyl-phenoxy)-phenyl]-N',N''-bis-methoxycarbonyl-guanidine, N-[2-propionamido-5-(3-cyano-phenoxy)-phenyl]-N',N''-bis-methoxycarbonyl-guanidine, N-[2-propionamido-5-(4-propionyl-phenoxy)-phenyl]-N',N''-bis-methoxycarbonyl-guanidine, N-[2-propionamido-5-(4-acetylamino-phenoxy)-phenyl]-N',N''-bis-methoxycarbonyl-guanidine, N-[2-propionamido-5-(4-methoxycarbonyl-phenoxy)-phenyl]-N',N''-bis-methoxycarbonyl-guanidine, N-[2-propionamido-5-(3,4-dimethyl-phenoxy)-phenyl]-N',N''-bis-methoxycarbonyl-guanidine, N-[2-propionamido-5-(3,4-dichloro-phenoxy)-phenyl]-N',N''-bis-methoxycarbonyl-guanidine, N-(2-acetamido-4-phenylthio-phenyl)-N'-methoxycarbonyl-N''-propionyl-guanidine, N-(2-acetamido-4-phenylthio-phenyl)-N'-ethoxycarbonyl-N''-propionyl-guanidine, N-(2-acetamido-4-phenylthio-phenyl)-N'-iso-propoxycarbonyl-N''-propionyl-guanidine, N-(2-acetamido-4-phenylthio-phenyl)-N'-sec.-butoxycarbonyl-N''-propionyl-guanidine, N-(2-propionamido-4-phenylthio-phenyl)-N'-methoxycarbpnyl-N''-propionyl-guanidine, N-(2-butyramido-4-phenylthio-phenyl)-N'-methoxycarbonyl-N''-propionyl-guanidine, N-(2-valeramido-4-phenylthio-phenyl)-N'-methoxycarbonyl-N''-propionyl-guanidine, N-(2-cyclopentanecarboxylic acid amido-4-phenylthio-phenyl)-N'-methoxycarbonyl-N''-propionyl-guanidine, N-(2-cyclohexanecarboxylic acid amido-4-phenylthio-phenyl)-N'-methoxycarbonyl-N''-propionyl-guanidine, N-(2-benzamido-4-phenylthio-phenyl)-N'-methoxycarbonyl-N''-propionyl-guanidine, N-(2-acetamido-4-phenylthio-phenyl)-N'-methoxycarbonyl-N''-acetyl-guanidine, N-(2-acetamido-4-phenylthio-phenyl)-N'-methoxycarbonyl-N''-butyryl-guanidine, N-(2-acetamido-4-phenylthio-phenyl)-N'-methoxycarbonyl-N''-cyclohexanecarbonyl-guanidine, N-(2-acetamido-4-phenylthio-phenyl)-N'-methoxycarbonyl-N''-benzoyl-guanidine, N-(2-acetamido-4-phenylthio-phenyl)-N'-methoxycarbonyl-N''-phenylacetyl-guanidine, N-(2-acetamido-4-phenylthio-phenyl)-N'-methoxycarbonyl-N''-phenoxyacetyl-guanidine, N-[2-(2'-methylureido)-4-phenylthio-phenyl]-N'-methoxycarbonyl-N''-propionyl-guanidine, N-[2-(2'-ethylureido)-4-phenylthio-phenyl]-N'-methoxycarbonyl-N''-propionyl-guanidine, N-[2-(2'-butylureido)-4-phenylthio-phenyl]-N'-methoxycarbonyl-N''-propionyl-guanidine, N-[2-(2'-ω-cyanopentylureido)-4-phenylthio-phenyl]-N'-methoxycarbonyl-N''-propionyl-guanidine, N-[2-(2'-β-methoxymethylureido)-4-phenylthio-phenyl]-N'-methoxycarbonyl-N''-propionyl-guanidine, N[2-(2'-benzylureido)-4-phenylthio-phenyl]-N'-methoxycarbonyl-N''-propionyl-guanidine, N-[2-(2'-phenylureido)-4-phenylthiophenyl]-N'-methoxycarbonyl-N''-propionyl-guanidine, N-(2-acetamido-4-phenylthio-phenyl)-N',N''-bis-methoxycarbonyl-guanidine, N-(2-acetamido-4-phenylthio-phenyl)-N',N''-bis-ethoxycarbonyl-guanidine, N-(2-acetamido-4-phenylthio-phenyl)-N',N''-bis-iso-propoxycarbonyl-guanidine, N-(2-acetamido-4-phenylthio-phenyl)-N',N''-bis-sec.-butoxycarbonyl-guanidine, N-(2-propionamido-4-phenylthio-phenyl)-N',N''-bis-methoxycarbonyl-guanidine, N-(2-butyramido-4-phenylthio-phenyl)-N',N''-bis-methoxycarbonyl-guanidine, N-(2-iso-butyramido-4-phenylthiophenyl)-N',N''-bis-methoxycarbonyl-guanidine, N-(2-valeramido-4-phenylthio-phenyl)-N',N''-bis-methoxycarbonyl-guanidine, N-(2-iso-valeramido-4-phenylthio-phenyl)-N',N''-bis-methoxycarbonyl-guanidine, N-(2-caproamido-4-phenylthio-phenyl)-N',N''-bis-methoxycarbonyl-guanidine, N-(2-iso-caproamido-4-phenylthio-phenyl)-N',N''-bis-methoxycarbonyl-guanidine, N-(2-cyclopentanecarboxylic acid amido-4-phenylthio-phenyl)-N',N''-bis-methoxycarbonyl-guanidine, N-(2-cyclohexanecarboxylic acid amido-4-phenylthio-phenyl)-N',N''-bis-methoxycarbonyl-guanidine, N-(2-phenylacetamido-4-phenylthio-phenyl)-N',N''-bis-methoxycarbonyl-guanidine, N-(2-phenoxyacetamido-4-phenylthiophenyl)-N',N''-bis-methoxycarbonyl-guanidine, N-(2-benzamido-4-phenylthio-phenyl)-N',N''-bis-methoxycarbonyl-guanidine, N-[2-(2'-methylureido)-4-phenylthio-phenyl]-N',N''-bis-methoxycarbonyl-guanidine, N-[2-(2'-ethylureido)-4-phenylthiophenyl]-N',N''-bis-methoxycarbonyl-guanidine, N-[2-(2'-butylureido)-4-phenylthio-phenyl]N',N''-bis-methoxy-carbonyl-guanidine, N-[2-(2'-ω-cyanopentylureido)-4-phenylthio-phenyl]-N',N''-bis-methoxycarbonyl-guanidine, N-[2-(2'-β-methoxyethylureido)-4-phenylthio-phenyl]-N',N''-bis-methoxycarbonyl-guanidine, N-[2-(2'-benzylureido)-4-phenylthio-phenyl]-N',N''-bis-methoxycarbonyl-guanidine, N-[2-(2'-phenylureido)-4-phenylthio-phenyl]-N',N''-bis-methoxycarbonyl-guanidine, N-[2-propionamido-4-(4-methyl-phenylthio)-phenyl]-N',N''-bis-methoxycarbonyl-guanidine, N-[2-propionamido-4-(3-methyl-phenylthio)phenyl]N',N''-bis-methoxycarbonyl-guanidine, N-[2-propionamido-4-(4-chloro-phenylthio)-phenyl]-N',N''-bis-methoxycarbonyl-guanidine, N-[2-propionamido-4-(3-chloro-phenylthio)-phenyl]-N',N''-bis-methoxycarbonyl-guanidine, N-[2-propion amido-4-(2-chloro-phenylthio)-phenyl]-N',N''-bis-methoxycarbonyl-guanidine, N-[2-propionamido-4-(4-methoxy-phenylthio)-phenyl]-N',N''-bis-methoxycarbonyl-guanidine, N-[2-propionamido-4-(3-methoxy-phenylthio)-phenyl]-N',N''-bis-methoxycarbonyl-guanidine, N-[2-propionamido-4-(4-methylthio-phenylthio)-phenyl]-N',N''-bis-methoxycarbonyl-guanidine, N-[2-propionamido-4-(3-methylthio-phenylthio)-phenyl]-N',N''-bismethoxycarbonyl-guanidine, N-[2-propionamido-4-(4-cyanophenylthio)-phenyl]-N',N''-bis-methoxycarbonyl-guanidine, N-[2-propionamido-4-(4-acetyl-phenylthio)-phenyl]-N',N''-bis-methoxycarbonyl-guanidine, N-[2-propionamido-4-(3-cyano-phenylthio)-phenyl]-N',N''-bis-methoxycarbonyl-guanidine, N-[2-propionamido-4-(4-propionyl-phenylthio)-phenyl]-N',N''-bis-methoxycarbonyl-guanidine, N-[2-propionamido-4-(4-acetylaminophenylthio)-phenyl]-N',N''-bis-methoxycarbonyl-guanidine, N-[2-propionamido-4-(4-methoxycarbonyl-phenylthio)-phenyl]-N',N''-bis-methoxycarbonyl-guanidine, N-[2-propionamido-4-(3,4-dimethylphenylthio)-phenyl]-N',N''-bis-methoxycarbonylguanidine, N-[2-propionamido-4-(3,4-dichloro-phenylthio)-phenyl]-N',N''-bis-methoxycarbonyl-guanidine, N-(2-acetamido-5-phenylthio-phenyl)-N'-methoxycarbonyl-N''-propionyl-guanidine, N-(2-acetamido-5-phenylthio-phenyl)-N'-ethoxycarbonyl-N''-propionyl-guanidine, N-(2-acetamido-4-phenylthio-phenyl)-N'-iso-propoxycarbonyl-N''-propionyl-guanidine, N-(2-acetamido-5-phenylthio-phenyl)-N'-sec.-butoxycarbonyl-N''-propionyl-quanidine, N-(2-propionamido-5-phenylthio-phenyl)-N'-methoxycarbonyl-N''-propionyl-guanidine, N-(2-butyramido-5-phenylthiophenyl)-N'-methoxycarbonyl-N''-propionyl-guanidine, N-(2-valeramido-5-phenylthio-phenyl)-N'-methoxycarbonyl-N''-propionyl-guanidine, N-(2-cyclopentanecarboxylic acid amido-5-phenylthio-phenyl)-N'-methoxycarbonyl-N''-propionyl-guanidine, N-(2-cyclohexanecarboxylic acid amido-5-phenylthio-phenyl)-N'-methoxycarbonyl-N''-propionyl-guanidine, N-(2-benzamido-5-phenylthio-phenyl)-N'-methoxycarbonyl-N''-propionyl-guanidine, N-(2-acetamido-5-phenylthio-phenyl)-N'-methoxycarbonyl-N''-acetyl-guanidine, N-(2-acetamido-5-phenylthio-phenyl)-N'-methoxycarbonyl-N''-butyryl-guanidine, N-(2-acetamido-5-phenylthio-phenyl)-N'-methoxycarbonyl-N''-cyclohexanecarbonyl-guanidine, N-(2-acetamido-5-phenylthio-phenyl)-N'-methoxycarbonyl-N''-benzoyl-guanidine, N-(2-acetamido-5-phenylthiophenyl)-N'-methoxycarbonyl-N''-phenylacetyl-guanidine, N-(2-acetamido-5-phenylthio-phenyl)-N'-methoxycarbonyl-N''-phenoxyacetyl-guanidine, N-[2-(2'-methylureido)-5-phenylthio-phenyl]-N'-methoxycarbonyl-N''-propionyl-guanidine, N-[2-(2'-ethylureido)-5-phenylthio-phenyl]-N'-methoxycarbonyl-N''-propionyl-guanidine, N-[2-(2'-butylureido)-5-phenylthio-phenyl]-N'-methoxycarbonyl-N''-propionyl-guanidine, N-[2-(2'-ω-cyanopentylureido)-5-phenylthio-phenyl]-N'-methoxycarbonyl-N''-propionyl-guanidine, N-[2-(2'-β-methoxymethylureido)-5-phenylthio-phenyl]-N'-methoxycarbonyl-N''-propionyl-guanidine, N-[2-(2'benzylureido)-5-phenylthio-phenyl]-N'-methoxycarbonyl-N''-propionyl-guanidine, N-[2-(2'-phenylureido)-5-phenylthio-phenyl]-N'-methoxycarbonyl-N''-propionyl-guanidine, N-(2-acetamido-5-phenylthio-phenyl)-N',N''-bis-methoxycarbonyl-guanidine, N-(2-acetamido-5-phenylthio-phenyl)-N',N''-bis-ethoxycarbonyl-guanidine, N-(2-acetamido-5-phenylthio-phenyl)-N',N''-bis-iso-propoxycarbonyl-guanidine, N-(2-acetamido-5-phenylthio-phenyl)-N',N''-bis-sec.-butoxycarbonyl-guanidine, N-(2-propionamido-5-phenylthio-phenyl)-N',N''-bis-methoxycarbonyl-guanidine, N-(2-butyramido-5-phenylthio-phenyl)-N',N''-bis-methoxycarbonyl-guanidine, N-(2-iso-butyramido-5-phenylthio-phenyl)-N',N''-bis-methoxycarbonyl-guanidine, N-(2-valeramido- 5-phenylthio-phenyl)-N',N''-bis-methoxycarbonyl-guanidine, N-(2-iso-valeramido-5-phenylthio-phenyl)-N',N''-bis-methoxycarbonyl-guanidine, N-(2-caproamido-5-phenylthio-phenyl)-N',N''-bis-methoxycarbonyl-guanidine, N-(2-iso-caproamido-5-phenylthio-phenyl)-N',N''-bis-methoxycarbonyl-guanidine, N-(2-cyclopentanecarboxylic acid amido-5-phenylthio-phenyl)-N',N''-bis-methoxycarbonyl-guanidine, N-(2-cyclohexanecarboxylic acid amido-5-phenylthio-phenyl)-N',N''-bis-methoxycarbonyl-guanidine, N-(2-phenylacetamido-5-phenylthio-phenyl)-N',N''-bis-methoxycarbonyl-guanidine, N-(2-phenoxyacetamido-5-phenylthio-phenyl)-N',N''-bis-methoxycarbonyl-guanidine, N-(2-benzamido-5-phenylthio-phenyl-N',N''-bis-methoxycarbonyl-guanidine, N-[2-(2'-methylureido)-5-phenylthio-phenyl]-N',N''-bis-methoxycarbonyl-guanidine, N-[2-(2'-ethylureido)-5-phenylthio-phenyl]-N',N''-bis-methoxycarbonyl-guanidine, N-[2-(2'-butylureido)-5-phenylthio-phenyl]-N',N''-bis-methoxycarbonyl-guanidine, N-[2-(2'-ω-cyanopentylureido)-5-phenylthio-phenyl]-N',N''-bis-methoxycarbonyl-guanidine, N-[2-(2'-β-methoxyethylureido)-5-phenylthio-phenyl]-N',N''-bis-methoxycarbonyl-guanidine, N-[2-(2'-benzylureido)-5-phenylthio-phenyl]-N',N''-bis-methoxycarbonyl-guanidine, N-[2-(2'-phenylureido)-5-phenylthio-phenyl]-N',N''-bis-methoxycarbonyl-guanidine, N-[2-propionamido-5-(4-methyl-phenylthio)-phenyl]-N',N''-bis-methoxycarbonyl-guanidine, N-[2-propionamido-5-(3-methyl-phenylthio)-phenyl]-N',N''-bis-methoxycarbonyl-guanidine, N-[2-propionamido-5-(4-chloro-phenylthio)-phenyl]-N',N''-bis-methoxycarbonyl-guanidine, N-[2-propionamido-5-(3-chloro-phenylthio)-phenyl]-N',N''-bis-methoxycarbonyl-guanidine, N-[2-propionamido-5-(3-chloro-phenylthio)-phenyl]-N',N''-bis-methoxycarbonyl-guanidine, N-[2-propionamido-5-(4-methoxy-phenylthio)-phenyl]-N',N''-bis-methoxycarbonyl-guanidine, N-[2-propionamido- 5-(3-methoxy-phenylthio)-phenyl]-N',N''-bis-methoxycarbonyl-guanidine, N-[2-propionamido-5-(4-methylthio-phenylthio)-phenyl]-N',N''-bis-methoxycarbonyl-guanidine, N-[2-propionamido-5-(3-methylthio-phenylthio)-phenyl]-N',N''-bis-methoxycarbonyl-guanidine, N-[2-propionamido-5-(4-cyano-phenylthio)-phenyl]-N',N''-bis-methoxycarbonyl-guanidine, N-[2-propionamido-5-(4-acetyl-phenylthio)-phenyl]-N',N''-bis-methoxycarbonyl-guanidine, N-[2-propionamido-5-(3-cyano-phenylthio)-phenyl]-N',N''-bis-methoxycarbonyl-quanidine, N-[2-propionamido-5-(4-propionyl-phenylthio)-phenyl]-N',N''-bis-methoxycarbonyl-guanidine, N-[2-propionamido-5-(4-acetylamino-phenyl-thio)-phenyl]-N',N''-bis-methoxycarbonyl-guanidine, N-[2-propionamido-5-(4-methoxycarbonyl-phenylthio)-phenyl]-N',N''-bis-methoxycarbonyl-guanidine, N-[2-propionamido-5-(3,4-dimethyl-phenylthio)-phenyl]-N',N''-bis-methoxycarbonyl-quanidine, N-[2-propionamido-5-(3,4-dichloro-phenylthio)-phenyl]-N',N''-bis-methoxycarbonyl-guanidine, N-(2-acetamido-4-phenylsulphinyl-phenyl)-N'-methoxycarbonyl-N''-propionyl-guanidine, N-(2-acetamido-4-phenylsulphinyl-phenyl)-N'-ethoxycarbonyl-N''-propionyl-guanidine, N-(2-acetamido-4-phenylsulphinyl-phenyl)-N'-iso-propoxycarbonyl-N''-propionyl-guanidine, N-(2-acetamido-4-phenylsulphinyl-phenyl)-N'-sec.-butoxycarbonyl-N''-propionyl-guanidine, N-(2-propionamido-4-phenylsulphinyl-phenyl)-N'-methoxycarbonyl-N''-propionyl-guanidine, N-(2-butyramido-4-phenylsulphinyl-phenyl)-n'-methoxycarbonyl-N''-propionyl-guanidine, N-(2-valeramido-4-phenylsulphinyl-phenyl)-N'-methoxycarbonyl-N''-propionyl-guanidine, N-(2-cyclopentanecarboxylic acid amido-4-phenylsulphinyl-phenyl)-N'-methoxycarbonyl-N''-propionyl-guanidine, N-(2-cyclohexanecarboxylic acid amido-4-phenylsulphinyl-phenyl)-N'-methoxycarbonyl-N''-propionyl-quanidine, N-(2-benzamido-4-phenylsulphinyl-phenyl)-N'-methoxycarbonyl-N''-propionyl-guanidine, N-(2-acetamido-4-phenylsulphinyl-phenyl)-N'-methoxycarbonyl-N''-acetyl-guanidine, N-(2-acetamido-4-phenylsulphinyl-phenyl)-N'-methoxycarbonyl-N''-butyryl-guanidine, N-(2-acetamido-4-phenylsulphinyl-phenyl)-N'-methoxycarbonyl-N''-cyclohexanecarbonyl-guanidine, N-(2-acetamido-4-phenylsulphinyl-phenyl)-N'-methoxycarbonyl-N''-benzoyl-guanidine, N-(2-acetamido-4-phenylsulphinyl phenyl)-N'-methoxycarbonyl-N"-phenylacetyl-guanidine, N-(2-acetamido-4-phenylsulphinyl-phenyl)-N'-methoxycarbonyl-N"-phenoxyacetyl-guanidine, N-[2-(2'-methylureido)-4-phenylsulphinyl-phenyl]-N'-methoxycarbonyl-N"-propionyl-guanidine, N-[2-(2'-ethylureido)-4-phenylsulphinyl-phenyl]-N'-methoxycarbonyl-N"-propionyl-guanidine, N-[2-(2'-butylureido)-4-phenylsulphinyl-phenyl]-N'-methoxycarbonyl-N"-propionyl-guanidine, N-[2-(2'-ω-cyanopentylureido)-4-phenylsulphinyl-phenyl]-N'-methoxycarbonyl-N"-propionyl-guanidine, N-[2-(2'-β-methoxymethylureido)-4-phenylsulphinyl-phenyl]-N'-methoxycarbonyl-N"-propionyl-guanidine, N-[2-(2'-benzylureido)-4-phenylsulphinyl-phenyl]-N'-methoxycarbonyl-N"-propionyl-guanidine, N-[2-(2'-phenylureido)-4-phenylsulphinyl-phenyl]-N'-methoxycarbonyl-N"-propionyl-guanidine, N-(2-acetamido-4-phenylsulphinyl-phenyl)-N',-N"-bis-methoxycarbonyl-guanidine, N-(2-acetamido-4-phenylsulphinyl-phenyl)-N' ,N"-bis-ethoxycarbonyl-guanidine, N-(2-acetamido-4-phenylsulphinyl-phenyl)-N',N"-bis-iso-propoxycarbonyl-guanidine, N-(2-acetamido-4-phenylsulphinyl-phenyl)-N',N"-bis-sec.-butoxycarbonyl-guanidine, N-(2-propionamido-4-phenylsulphinyl-phenyl)-N',N"-bis-methoxycarbonyl-guanidine, N-(2-butyramido-4-phenylsulphinyl-phenyl)-N', N"-bis-methoxycarbonyl-guanidine, N-(2-iso-butyramido-4-phenylsulphinyl-phenyl)-N',N"-bis-methoxycarbonyl-guanidine, N-(2-valeramido-4-phenylsulphinyl-phenyl)-N',N"-bis-methoxycarbonyl-guanidine, N-(2-iso-valeramido-4-phenylsulphinyl-phenyl)-N',N"-bis-methoxycarbonyl-guanidine, N-(2-caproamido-4-phenylsulphinyl-phenyl)-N',N"-bis-methoxycarbonyl-guanidine, N 2-iso-caproamido-4-phenylsulphinyl-phenyl)-N',N"-bis-methoxycarbonyl-guanidine, N-(2-cyclopentanecarboxylic acid amido-4-phenylsulphinyl-phenyl)-N',N"-bis-methoxycarbonyl-guanidine, N-(2-cyclohexanecarboxylic acid amido-4-phenylsulphinyl-phenyl)-N',N"-bis-methoxycarbonyl-guanidine, N-(2-phenylacetamido-4-phenylsulphinyl-phenyl)-N',N"-bis-methoxycarbonyl-guanidine, N-(2-phenoxyacetamido-4-phenylsulphinyl-phenyl)-N',N"-bis-methoxycarbonyl-guanidine, N-(2-benzamido-4-phenylsulphinyl-phenyl)-N',N"-bis-methoxycarbonyl-guanidine, N-[2-(2'-methylureide)-4-phenylsulphinyl-phenyl]-N',N"-bis-methoxycarbonyl-guanidine, N-[2-(2'-ethylureido)-4-phenylsulphinyl-phenyl]-N',N"-bis-methoxycarbonyl-guanidine, N-[2-(2'-butylureido)-4-phenylsulphinyl-phenyl]-N',N"-bis-methoxycarbonyl-guanidine, N-[2-(2'-ω-cyanopentylureido)-4-phenylsulphinyl-phenyl]-N',N"-bis-methoxycarbonyl-guanidine, N-[2-(2'-β-methoxyethyl-ureido)-4-phenylsulphinyl-phenyl]-N', N"-bis-methoxycarbonyl-guanidine, N-[2-(2'-benzylureido)-4-phenylsulphinyl-phenyl]-N',N"-bis-methoxycarbonyl-guanidine, N-[2-(2'-phenylureido)-4-phenylsulphinyl-phenyl]-N',N"-bis-methoxycarbonyl-guanidine, N-[2-propionamido-4-(4-methyl-phenylsulphinyl)-phenyl]-N',N"-bis-methoxycarbonyl-guanidine N-[2-propionamido-4-(3-methyl-phenylsulphinyl)-phenyl]-N',N"-bis-methoxycarbonyl-guanidine, N-[2-propionamido-4-(4-chloro-phenylsulphinyl)-phenyl]-N',N"-bis-methoxycarbonyl-guanidine, N-[2-propionamido-4-(3-chloro-phenylsulphinyl)-phenyl]-N',N"-bis-methoxycarbonyl-guanidine, N-[2-propionamido-4-(2-chloro-phenylsulphinyl)-phenyl]-N',N"-bis-methoxycarbonyl-guanidine, N-[2-propionamido-4-(4-methoxy-phenylsulphinyl)-phenyl]-N',N"-bis-methoxycarbonyl-guanidine, N-[2-propionamido-4-(3-methoxy-phenylsulphinyl)-phenyl]-N',N"-bis-methoxycarbonyl-guanidine, N-[2-propionamido-4-(4-methylthio-phenylsulphinyl)-phenyl]-N',N"-bis-methoxycarbonyl-guanidine, N-[2-propionamido-4-(3-methylthio-phenylsulphinyl)-phenyl]-N',N"-bis-methoxycarbonyl-guanidine, N-[2-propionamido-4-(4-cyano-phenylsulphinyl)-phenyl]-N',N"-bis-methoxycarbonyl-quanidine, N-[2-propionamido-4-(4-acetyl-phenylsulphinyl)-phenyl]-N',N"-bis-methoxycarbonyl-guanidine, N-[2-propionamido-4-(3-cyano-phenylsulphinyl)-phenyl]-N',N"-bis-methoxycarbonyl-guanidine, N-[2-propionamido-4-(4-propionyl-phenylsulphinyl)-phenyl]-N',N"-bis-methoxycarbonyl-guanidine, N-[2-propionamido-4-(4-acetylamino-phenylsulphinyl)-phenyl]-N',N"-bis-methoxycarbonyl-guanidine, N-[2-propionamido-4-(4-methoxycarbonyl-phenylsulphinyl)-phenyl]-N',N"-bis-methoxycarbonyl-guanidine, N-[2-propionamido-4-(3,4-dimethyl-phenylsulphinyl)-phenyl]-N',N"-bis-methoxycarbonyl-guanidine, N-[2-propionamido-4-(3,4-dichloro-phenylsulphinyl)-phenyl]-N',N"-bis-methoxycarbonyl-guanidine, N-(2-acetamido-5-phenylsulphinyl)-N'-methoxycarbonyl-N"-propionyl-guanidine, N-(2-acetamido-5-phenylsulphinyl-phenyl)-N'-ethoxycarbonyl-N"-propionyl-guanidine, N-(2-acetamido-5-phenylsulphinyl-phenyl)-N'-iso-propoxycarbonyl-N"-propionyl-guanidine, N-(2-acetamido-5-phenylsulphinyl-phenyl)-N'-sec.-butoxycarbonyl-N"-propionyl-guanidine, N-(2-propionamido-5-phenylsulphinyl-phenyl)-N'-methoxycarbonyl-N"-propionyl-guanidine, N-(2-butyramido-5-phenylsulphinyl-phenyl)-N'-methoxycarbonyl-N"-propionyl-guanidine, N-(2-valeramido- 5-phenylsulphinyl-phenyl)-N'-methoxycarbonyl-N"-propionyl-guanidine, N-(2-cyclopentanecarboxylic acid amido-5-phenylsulphinyl-phenyl)-N'-methoxycarbonyl-N"-propionyl-guanidine, N-(2-cyclohexanecarboxylic acid amido-5-phenylsulphinyl-phenyl)-N'-methoxycarbonyl-N"-propionyl-guanidine, N-(2-benzamido-5-phenylsulphinyl-phenyl)-N'-methoxycarbonyl-N"-propionyl-guanidine, N-(2-acetamido-5-phenylsulphinyl-phenyl)-N'-methoxycarbonyl-N"-acetyl-guanidine, N-(2-acetamido-5-phenylsulphinyl-phenyl)-N'-methoxycarbonyl-N"-butyryl-guanidine, N-(2-acetamido-5-phenylsulphinyl-phenyl)-N'-methoxycarbonyl-N"-cyclohexanecarbonyl-guanidine, N-(2-acetamido-5-phenylsulphinyl-phenyl)-N'-methoxycarbonyl-N"-benzoyl-guanidine, N-(2-acetamido-5-phenylsulphinyl-phenyl)-N'-methoxycarbonyl-N"-phenylacetyl-guanidine, N-(2-acetamido-5-phenylsulphinyl-phenyl)-N'-methoxycarbonyl-N"-phenoxyacetyl-guanidine, N-[2-(2'-methylureido)-5-phenylsulphinyl-phenyl]-N'-methoxycarbonyl-N"-propionyl-guanidine, N-[2-(2'-ethyl-ureido)-5-phenylsulphinyl-phenyl]-N'-methoxycarbonyl-N"-propionyl-guanidine, N-[2-(2'-butylureido)-5-phenylsulphinyl-phenyl]-N'-methoxycarbonyl-N"-propionyl-guanidine, N-[2-(2'-ω-cyanopentylureido)-5-phenylsulphinyl-phenyl]-N'-methoxycarbonyl-N"-propionyl-guanidine, N-[2-(2'-β-methoxymethylureido)-5-phenylsulphinyl-phenyl]-N'-methoxycarbonyl-N"-propionyl-guanidine, N-[2-(2'-benzyluriedo)-5-phenylsulphinyl-phenyl]-N'-methoxycarbonyl-N"-propionyl-guanidine, N-[2-(2'-phenylureido)-5-phenylsulphinyl-phenyl]-N'-methoxycarbonyl-N"-propionyl-guanidine, N-(2-acetamido-5-phenylsulphinyl-phenyl)-N',N"-bis-methoxycarbonyl-guanidine, N-(2-acetamido-5-phenylsulphinyl-phenyl)-N',N"-bis-ethoxycarbonyl-guanidine, N-(2-acetamido-5-phenylsulphinyl-phenyl)-N',N"-bis-iso-propoxycarbonyl-guanidine, N-(2-acetamido-5-phenylsulphinyl-phenyl)-N',N"-bis-sec.-butoxycarbonyl-guanidine, N-(2-propionamido-5-phenylsulphinyl-phenyl)-N',N"-bis-methoxycarbonyl-guanidine, N-(2-butyramido-5-phenylsulphinyl-phenyl)-N',N"-bis-methoxy-carbonyl-guanidine, N-(2-iso-butyramido-5-phenylsulphinyl-phenyl)-N',N"-bis-methoxycarbonyl-guanidine, N-(2-valeramido-5-phenylsulphinyl-phenyl)-N',N"8    N-(2-iso-valeramido-5-phenylsulphinyl-phenyl)-N(,N"-bis-methoxycarbonyl-guanidine, N-(2-caproamido-5-phenylsulphinylphenyl)-N',N"-bis-methoxycarbonyl-guanidine, N-(2-iso-caproamido-5-phenylsulphinyl-phenyl)-N',N"-bis-methoxycarbonyl-guanidine, N-(2-cyclopentanecarboxylic acid amido-5-phenylsulphinyl-phenyl)-N',N"-bis-methoxycarbonyl-guanidine, N-(2-cyclohexanecarboxylic acid amido-5-phenylsulphinyl-phenyl)N',N"-bis-methoxycarbonyl-guanidine, N-(2-phenylacetamido-5-phenylsulphinyl-phenyl)-N',N"-bis-methoxycarbonyl-guanidine, N-(2-phenoxyacetamido-5-phenylsulphinyl-phenyl)-N',N"-bismethoxycarbonyl-guanidine, N-(2-benzamido-5-phenylsulphinylphenyl)-N',N"-bis-methoxycarbonyl-guanidine, N-[2-(2'-methylureido)- 5-phenylsulphinyl-phenyl]-N',N"-bis-methoxycarbonylguanidine, N-[2-(2'-ethylureido)-5-phenylsulphinyl-phenyl]-N',N"-bis-methoxycarbonyl-guanidine, N-[2-(2'-butylureido)-5-phenylsulphinyl-phenyl]-N',N"-bis-methoxycarbonyl-guanidine, N-[2'-(2'-ω-cyanopentylureido)-5-phenylsulphinyl-phenyl]-N',N"-bis-methoxycarbonyl-guanidine, N-[2-(2'-β-methoxyethylureido)-5-phenylsulphinyl-phenyl]-N',N"-bis-methoxycarbonylguanidine, N-[2-(2'-benzylureido)-5-phenylsulphinyl-phenyl]-N',N"-bis-methoxycarbonyl-guanidine, N-[2-(2'-phenylureido)-5-phenylsulphinyl-phenyl]-N',N"-bis-methoxycarbonyl-guanidine, N-[2-propionamido-5-(4-methyl-phenylsulphinyl)-phenyl]-N',N"-bis-methoxycarbonyl-guanidine, N-[2-propionamido-5-(3-methylphenylsulphinyl)-phenyl]-N',N"-bis-methoxycarbonyl-guanidine, N-[2-propionamido-5-(4-chloro-phenylsulphinyl)-phenyl]-N',N"-bis-methoxycarbonyl-guanidine, N-[2-propionamido-5-(3-chlorophenylsulphinyl)-phenyl]-N',N"-bis-methoxycarbonyl-guanidine, N-[2-propionamide-5-(3-chloro-phenylsulphinyl)-phenyl]-N',N"-bis-methoxycarbonyl-guanidine, N-[2-propionamido-5-(4-methoxyphenylsulphinyl)-phenyl]-N',N"-bis-methoxycarbonyl-guanidine, N-[2-propionamido-5-(3-methoxy-phenylsulphinyl)-phenyl]-N',N"-bis-methoxycarbonyl-guanidine, N-[2-propionamido-5-(4-methylthio-phenylsulphinyl)-phenyl]-N',N"-bis-methoxycarbonyl-guanidine, N-[2-propionamido-5-(3-methylthio-phenylsulphinyl)-phenyl]-N',N"-bis-methoxycarbonyl-guanidine, N-[2-propionamido5-(4-cyano-phenylsulphinyl)-phenyl]-N',N"-bis-methoxycarbonyl-quanidine, N-[2-propionamido-5-(4-acetyl-phenylsulphinyl)-phenyl]-N',N"-bis-methoxycarbonyl-guanidine, N-[2-propionamido-5-(3-cyano-phenylsulphinyl)-phenyl]-N',N"-bis-methoxycarbonyl-guanidine, N-[2-propionamido-5-(4-propionyl-phenyl-sulphinyl)-phenyl]-N',N"-bis-methoxycarbonyl-guanidine, N-[2-propionamido-5-(4-acetylamino-phenylsulphinyl)-phenyl]-N',N"-bis-methoxycarbonyl-guanidine, N-[2-propionamido-5-(4-methoxycarbonyl-phenylsulphinyl)-phenyl]-N',N"-bis-methoxycarbonyl-guanidine, N-[2-propionamido-5-(3,4-dimethyl-phenylsulphinyl)-phenyl]-N',N"-bis-methoxycarbonyl-guanidine, N-[2-propionamido-5-(3,4-dichloro-phenylsulphinyl)-phenyl]-N',N"-bismethoxycarbonyl-guanidine, N-(2-acetamido-4-phenylsulphonylphenyl)-N'-methoxycarbonyl-N"-propionylguanidine, N-(2-acetamido-4-phenylsulphonyl-phenyl)-N'-ethoxycarbonyl-N-"-propionyl-guanidine, N-(2-acetamido-4-phenylsulphonyl-phenyl)-N'-iso-propoxycarbonyl-N"-propionyl-guanidine, N-(2-acetamido-4-phenylsulphonyl-phenyl)-N'-sec.-butoxycarbonyl-N"-propionylguanidine, N-(2-propionamido-4-phenylsulphonyl-phenyl)-N'-methoxycarbonyl-N"-propionyl-guanidine, N-(2-butyramido-4-phenylsulphonyl-phenyl)-N'-methoxycarbonyl-N"-propionyl-guanidine, N-(2-valeramido-4-phenylsulphonyl-phenyl)-N'-methoxycarbonyl-N"-propionyl-guanidine, N-(2-cyclopentanecarboxylic acid amido-4-phenylsulphonyl-phenyl)-N'-methoxycarbonyl-N"-propionyl-guanidine, N-(2-cyclohexanecarboxylic acid amido-4-phenylsulphonyl-phenyl)-N'-methoxycarbonyl-N"-propionyl-guanidine, N-(2-benzamido-4-phenylsulphonyl-phenyl)-N'-methoxycarbonyl-N"-propionyl-guanidine, N-(2-acetamido-4-phenylsulphonyl-phenyl)-N'-methoxycarbonyl-N"-acetyl-guanidine, N-(2-acetamido-4-phenylsulphonyl-phenyl)-N'-methoxycarbonyl-N"-butyryl-guanidine, N-(2-acetamido-4-phenylsulphonyl-phenyl)-N'-methoxycarbonyl-N"-cyclohexanecarbonyl-guanidine, N-(2-acetamido-4-phenylsulphonyl-phenyl)-N'-methoxycarbonyl-N"-benzoyl-guanidine, N-(2-acetamido-4-phenylsulphonyl-phenyl)-N'-methoxycarbonyl-N"-phenylacetyl-guanidine, N-(2-acetamido-4-phenylsulphonyl-phenyl)-N'-methoxycarbonyl-N"-phenoxyacetyl-guanidine, N-[2-(2'-methylureido)-4-phenylsulphonyl-phenyl]-N'-methoxycarbonyl-N"-propionyl-guanidine, N-[2-(2'-ethylureido)-4-phenylsulphonyl-phenyl]-N'-methoxycarbonyl-N"-propionyl-guanidine, N-[2-(2'-butylureido)-4-phenylsulphonyl-phenyl]-N'-methoxycarbonyl-N"-propionyl-guanidine, N-[2-(2'-ω-cyanopentylureido)-4-phenylsulphonyl-phenyl]-N'-methoxycarbonyl-N"-propionyl-guanidine, N-[2-(2'-β-methoxymethylureido)-4-phenylsulphonyl-phenyl]-N'-methoxycarbonyl-N"-propionyl-guanidine, N-[2-(2'-benzylureido)-4-phenylsulphonyl-phenyl]-N'-methoxycarbonyl-N"-propionyl-guanidine, N-[2-(2'-phenylureido)-4-phenylsulphonyl-phenyl]-N'-methoxycarbonyl-N"-propionyl-guanidine, N-(2-acetamido-4-phenylsulphonyl-phenyl)-N',N"-bismethoxycarbonyl-guanidien, N-(2-acetamido-4-phenylsulphonylphenyl)-N',N"-bis-ethoxycarbonyl-guanidine, N-(2-acetamido-4-phenylsulphonyl-phenyl)-N',N"-bis-iso-propoxycarbonyl-guanidine, N-(2-acetamido-4-phenylsulphonyl-phenyl)-N',N"-bis-sec.-butoxycarbonyl-guanidine, N-(2-propionamido-4-phenylsulphonylphenyl)-N',N"-bis-methoxycarbonyl-guanidine, N-(2-butyramido-4-phenylsulphonyl-phenyl)-N',N"-bis-methoxycarbonyl-guanidine, N-(2-iso-butyramido-4-phenylsulphonyl-phenyl)-N',N"-bismethoxycarbonyl-guanidine, N-(2-valeramido-4-phenylsulphonyl-phenyl)-N',N"-bis-methoxycarbonyl-guanidine, N-(2-iso-valeramido-4-phenylsulphonyl-phenyl)-N',N"-bis-methoxycarbonyl-guanidine, N-(2-caproamido-4-phenylsulphonyl-phenyl)-N',N"-bis-methoxycarbonyl-guanidine, N-(2-iso-caproamido-4-phenylsulphonyl-phenyl)-N',N"-methoxycarbonyl-guanidine, N-(2-cyclopentanecarboxylic acid amido-4-phenylsulphonyl-phenyl)-N',N"-bis-methoxycarbonyl-guanidine, N-(2-cyclohexanecarboxylic acid amido-4-phenylsulphonyl-phenyl)-N',N"-bis-methoxycarbonyl-guanidine, N-(2-phenylacetamido-4-phenylsulphonylphenyl)-N',N"-bis-methoxycarbonyl-guanidine, N-(2-phenoxyacetamido-4-phenylsulphonyl-phenyl)-N',N"-bis-methoxycarbonyl-guanidine, N-(2-benzamido-4-phenylsulphonyl-phenyl)-N',N"-bis-methoxycarbonyl-guanidine, N-[2-(2'-methylureido)-4-phenylsulphonyl-phenyl]-N',N"- bis-methoxycarbonyl-guanidine, N-[2-(2'-ethylureido)-4-phenylsulphonyl-phenyl]-N',N''-bismethoxycarbonyl-guanidine, N-[2-(2'-butylureido)-4-phenyl-sulphonyl-phenyl]-N',N''-bis-methoxycarbonyl-guanidine, N-[2-(2'-ω-cyanopentylureido)-4-phenylsulphonyl-phenyl]-N',N''-bis-methoxycarbonyl-guanidine, N-[2-(2'-β-methoxyethyl-ureido)-4-phenylsulphonyl-phenyl]-N',N''-bis-methoxycarbonyl-guanidine, N-[2-(2'-benzylureido)-4-phenylsulphonyl-phenyl]-N',N''-bismethoxycarbonyl-guanidine, N-[2-(2'-phenylureido)-4-phenylsulphonyl-phenyl]-N',N''-bis-methoxycarbonyl-guanidine, N-[2-propionamido-4-(4-methyl-phenylsulphonyl)-phenyl]-N',N''-bismethoxycarbonyl-guanidine, N-[2-propionamido-4-(3-methylphenylsulphonyl)-phenyl]-N',N''-bis-methoxycarbonyl-guanidine, N-[2-propionamido-4-(4-chloro-phenylsulphonyl)-phenyl]-N',N''-bis-methoxycarbonyl-guanidine, N-[2-propionamido-4-(3-chlorophenylsulphonyl)-phenyl]-N',N''-bis-methoxycarbonyl-guanidine, N-[2-propionamido-4-(2-chloro-phenylsulphonyl)-phenyl]-N',N''-bis-methoxycarbonyl-guanidine, N-[2-propionamido-4-(4-methoxy-phenylsulphonyl)-phenyl]-N',N''-bis-methoxycarbonyl-guanidine, N-[2-propionamido-4-(3-methoxy-phenylsulphonyl)-phenyl]-N',N''-bis-methoxycarbonyl-guanidine, N-[2-propionamido-4-(4-methylthio-phenylsulphonyl)-phenyl]-N',N''-bis-methoxycarbonyl-guanidine, N-[2-propionamido-4-(3-methylthio-phenylsulphonyl)-phenyl]-N',N''-bis-methoxycarbonyl-guanidine, N-[2-propionamido-4-(4-cyano-phenylsulphonyl)-phenyl]-N',N''-bis-methoxycarbonyl-guanidine, N-[2-propionamido-4-(4-acetyl-phenylsulphonyl)-phenyl]-N',N''-bis-methoxycarbonyl-guanidine, N-[2-propionamido-4-(3-cyano-phenylsulphonyl)-phenyl]-N',N''-bis-methoxycarbonyl-guanidine, N-[2-propionamido-4-(4-propionylphenylsulphonyl)-phenyl]-N',N''-bis-methoxycarbonyl-guanidine, N-[2-propionamido-4-(4-acetylamino-phenylsulphonyl)-phenyl]-N',N''-bis-methoxycarbonyl-guanidine, N-[2-propionamido-4-(4-methoxycarbonyl-phenylsulphonyl)-phenyl]-N',N''-bis-methoxycarbonyl-guanidine, N-[2-propionamido-4-(3,4-dimethyl-phenylsulphonyl)-phenyl]-N',N''-bis-methoxycarbonyl-guanidine, N-[2-propionamido-4-(3,4-dichloro-phenylsulphonyl)-phenyl]-N',N''-bis-methoxycarbonyl-guanidine, N-(2-acetamido-4-phenylsulphonyl-phenyl)-N'-methoxycarbonyl-N''-propionyl-guanidine, N-(2-acetamido-4-phenylsulphonyl-phenyl)-N'-ethoxycarbonyl-N''-propionyl-guanidine, N-(2-acetamido-4-phenylsulphonyl-phenyl)-N'-iso-propoxycarbonyl-N''-propionyl-guanidine, N-(2-acetamido-5-phenylsulphonyl-phenyl)-N'-sec.-butoxycarbonyl-N''-propionyl-guanidine, N-(2-propionamido-4-phenylsulphonyl-phenyl)-N'-methoxycarbonyl-N''-propionyl-guanidine, N-(2-butyramido-5-phenylsulphonyl-phenyl)-N'-methoxycarbonyl-N''-propionyl-guanidine, N-(2-valeramido-5-phenylsulphonyl-phenyl)-N'-methoxycarbonyl-N''-propionyl-guanidine, N-(2-cyclopentanecarboxylic acid amido-5-phenylsulphonyl-phenyl)-N'-methoxycarbonyl-N''-propionyl-guanidine, N-(2-cyclohexanecarboxylic acid amido-5-phenylsulphonyl-phenyl)-N'-methoxycarbonyl-N''-propionyl-guanidine, N-(2-benzamido-5-phenylsulphonyl-phenyl)-N'-methoxycarbonyl-N''-propionyl-guanidine, N-(2-acetamido-5-phenylsulphonyl-phenyl)-N'-methoxycarbonyl-N''-acetyl-guanidine, N-(2-acetamido-5-phenylsulphonyl-phenyl)-N'-methoxycarbonyl-N''-butyryl-guanidine, N-(2-acetamido-5-phenylsulphonyl-phenyl)-N'-methoxycarbonyl-N''-cyclohexanecarbonyl-guanidine, N-(2-acetamido-5-phenylsulphonyl-phenyl)-N'-methoxycarbonyl-N''-benzoyl-guanidine, N-(2-acetamido-5-phenylsulphonyl-phenyl)-N'-methoxycarbonyl-N''-phenylacetyl-guanidine, N-(2-acetamido-5-phenylsulphonyl-phenyl)-N'-methoxycarbonyl-N''-phenoxyacetyl-guanidine, N-[2-(2'-methylureido)-5-phenylsulphonyl-phenyl]-N'-methoxycarbonyl-N''-propionyl-guanidine, N-[2-(2'-ethylureido)-5-phenylsulphonyl-phenyl]-N'-methoxycarbonyl-N''-propionyl-guanidine, N-[2-(2'-butylureido)-5-phenylsulphonyl-phenyl]-N'-methoxycarbonyl-N''-propionyl-guanidine, N-[2-(2'-ω-cyanopentylureido)-5-phenylsulphonyl-phenyl]-N'-methoxycarbonyl-N''-propionyl-guanidine, N-[2-(2'-β-methoxymethylureido)-5-phenylsulphonyl-phenyl]-N'-methoxycarbonyl-N''-propionyl-guanidine, N-[2-(2'-benzylureido)-5-phenylsulphonyl-phenyl]-N'-methoxycarbonyl-N''-propionyl-guanidine, N-[2-(2'-phenylureido)-5-phenylsulphonyl-phenyl]-N'-methoxycarbonyl-N''-propionyl-guanidine, N-''-acetamido-5-phenylsulphonyl-phenyl)-N',N''-bis-methoxycarbonyl-guanidine, N-(2-acetamido-5-phenylsulphonyl-phenyl)-N',N''-bis-ethoxycarbonyl-guanidine, N-(2-acetamido-5-phenylsulphonyl-phenyl)-N',N''-bis-iso-propoxycarbonyl-guanidine, N-(2-acetamido-5-phenylsulphonyl-phenyl)-N',N''-bis-sec.-butoxycarbonyl-guanidine, N-(2-propionamido-5-phenylsulphonyl-phenyl)-N',N''-bis-methoxycarbonyl-guanidine, N-(2-butyramido-5-phenylsulphonyl-phenyl)-N',N''-bis-methoxycarbonyl-guanidine, N-(2-iso-butyramido-5-phenylsulphonyl-phenyl)-N',N''-bis-methoxycarbonyl-guanidine, N-(2-valeramido-5-phenylsulphonyl-phenyl)-N',N''-bis-methoxycarbonyl-guanidine, N-(2-iso-valeramido-5-phenylsulphonyl-phenyl)-N',N''-bis-methoxycarbonyl-guanidine, N-(2-caproamido-5-phenylsulphonyl-phenyl)-N',N''-bis-methoxycarbonyl-guanidine, N-(2-iso-caproamido-5-phenylsulphonyl-phenyl)-N',N''-bis-methoxycarbonyl-guanidine, N-(2-cyclopentanecarboxylic acid amido-5-phenylsulphonyl-phenyl)-N',N''-bis-methoxycarbonyl-guanidine, N-(2-cyclohexanecarboxylic acid amido-5-phenylsulphonyl-phenyl)-N',N''-bis-methoxycarbonyl-guanidine, N-(2-phenylacetamido-5-phenylsulphonyl-phenyl)-N',N''-bis-methoxycarbonyl-guanidine, N-(2-phenoxyacetamido-5-phenylsulphonyl-phenyl)-N',N''-bis-methoxycarbonyl-guanidine, N-(2-benzamido-5-phenylsulphonyl-phenyl)-N',N''-bis-methoxycarbonyl-guanidine, N-[2-(2'-methylureido)-5-phenylsulphonyl-phenyl]-N',N''-bis-methoxycarbonyl-guanidine, N-[2-(2'-ethylureido)-5-phenylsulphonyl-phenyl]-N',N''-bis-methoxycarbonyl-guanidine, N-[2-(2'-butylureido)-5-phenylsulphonyl-phenyl]-N',N''-bis-methoxycarbonyl-guanidine, N-[2-(2'-ω-cyanopentylureido)-5-phenylsulphonyl-phenyl]-N',N''-bis-methoxycarbonyl-guanidine, N-[2-(2'-β-methoxyethyl-ureido)-5-phenylsulphonyl-phenyl]-N',N''-bis-methoxycarbonyl-guanidine, N-[2-(2'-benzylureido)-5-phenylsulphonyl-phenyl]-N',N''-bis-methoxycarbonyl-guanidine, N-[2-(2'-phenylureido)-5-phenylsulphonyl-phenyl]-N',N''-bis-methoxycarbonyl-guanidine, N-[2-propionamido-5-(4-methylphenylsulphonyl)-phenyl]-N',N''-bis-methoxycarbonyl-guanidine, N-[2-propionamido-5-(3-methyl-phenylsulphonyl)-phenyl]-N',N''-bis-methoxycarbonyl-guanidine, N-[2-propionamido-5-(4-chloro-phenylsulphonyl)-phenyl]-N',N''-bis-methoxycarbonyl-guanidine, N-[2-propionamido-5-(4-chloro-phenylsulphonyl)-phenyl]-N',N''-bis-methoxycarbonyl-guanidine, N-[2-propionamido-5-(3-chloro-phenylsulphonyl)-phenyl]-N',N''-bis-methoxycarbonyl-guanidine, N-[2-propionamido-5-(4-methoxy-phenylsulphonyl)-phenyl]-N',N''-bis-methoxycarbonyl-guanidine, N-[2-propionamido-5-(3-methoxy-phenylsulphonyl)-phenyl]-N',N''-bis-methoxycarbonyl-guanidine, N-[2-propionamido-5-(4-methylthio-phenylsulphonyl)-phenyl]-N',N''-bis-methoxycarbonyl-guanidine, N-[2-propionamido-5-(3-methylthio-phenylsulphonyl)-phenyl]-N',N''-bis-methoxycarbonyl-guanidine, N-[2-propionamido-5-(4-cyano-phenylsulphonyl)-phenyl]-N',N''-bis-methoxycarbonyl-guanidine, N-[2-propionamido-5-(4-acetyl-phenylsulphonyl)-phenyl]-N',N''-bis-methoxycarbonyl-guanidine, N-[2-propionamido-5-(3-cyano-phenylsulphonyl)-phenyl]-N',N''-bis-methoxycarbonyl-guanidine, N-[2-propionamido-5-(4-propionyl-phenylsulphonyl)-phenyl]-N',N''-bis-methoxycarbonyl-guanidine, N-[2-propionamido-5-(4-acetylamino-phenylsulphonyl)-phenyl]-N',N''-bis-methoxycarbonyl-guanidine, N-[2-propionamido-5-(4-methoxycarbonyl-phenylsulphonyl)-phenyl]-N',N''-bis-methoxycarbonyl-guanidine, N-[2-propionamido-5-(3,4-dimethyl-phenylsulphonyl)-phenyl]-N',N''-bis-methoxycarbonyl-guanidine and N-[2-propionamido-5-(3,4-dichloro-phenylsulphonyl)-phenyl]-N',N''-methoxycarbonyl-guanidine.

The compounds prepared in accordance with the invention show a surprisingly improved action against one or more of the following nematodes and cestodes:
1. Hookworms (for example *Uncinaria stenocehala, Ancylostoma caninum* and *Bunostomum trigonocephalum*).
2. Trichostrongylidae (for example *Nippostrongylus muris, Haemonchus contortus, Trichostrongylus columbriformis* and *Ostertagia circumcincta*).
3. Strongylidae (for example *Oesophagostomum columbianum*).
4. Rhabditidae (for example *Strongyloides ratti*).
5. Ascaridae (for example *Ascaris suum, Toxocara canis* and *Toxascaris leonina*).
6. Threadworms (for example *Aspiculuris tetraptera*).
7. Heterakidae (for example *Heterakis spumosa*).
8. Whipworms (for example *Trichuris muris*).
9. Filariae (for example *Litomosoides carinii* and *Dipetalonema witei*).
10. Cestodes (for example *Hymenolepis nana, Taenia pisiformis* and *Echinococcus multilocularis*).

The action of the compounds of the invention can be conveniently observed in vivo by oral and patenteral administration to test animals heavily infested with parasites.

Hookworm test / sheep and dogs

Sheep experimentally infected with Bunostomum trigonocephalum were treated after the end of the prepatency period of the parasites. The amount of active compound was administered orally as pure active compound in gelatin capsules.

Dogs experimentally infected with *Uncinaria stenocephala* or *Ancylostoma caninum* were treated after the end of the pre-patency period of the parasites. The amount of active compound was administered orally as pure active compound in gelatin capsules.

The effectiveness is determined by counting the worms expelled after the treatment and, after dissection, the worms surviving in the test animals, and calculating the percentage of worms expelled.

The active compounds tested, the dosages used and the action can be seen from the table which follows, which lists the active compounds and the minimum dosage, in mg of active compound per kg of body weight of the test animal, which reduces the worm infection of the test animal by more than 90%.

Table 1

| Compound | | Minimum effective dose (Red. > 90%) in mg/kg |
|---|---|---|
| A1 | ⬡—O—⬡(—NH—C(=N—CO—OCH$_3$)—NH—CO—OCH$_3$)(—NH—CO—CH$_2$—CH$_2$—CH$_3$) | Bunostomum trig. 2.5 |
| A2 | ⬡—S—⬡(—NH—C(=N—CO—OCH$_3$)—NH—CO—OCH$_3$)(—NH—CO—C$_3$H$_7$) | Bunostomum trig. 1 |
| A3 | ⬡—S—⬡(—NH—C(=N—CO—OCH$_3$)—NH—CO—OCH$_3$)(—NH—CO—CH$_2$—OCH$_3$) | Uncinaria sten. 5<br>Bunostomum trig. 1 |
| A4 | ⬡—O—⬡(—NH—C(=N—CO—OCH$_3$)—NH—CO—OCH$_3$)(—NH—CO—CH$_2$—OCH$_3$) | Bunostomum trig. 2.5 |

*Nippostrongylus muris*-rats

Rats experimentally infected with Nippostrongylus muris were treated after the end of the pre-patency period of the parasites. The amount of active compound was administered orally as an aqueous suspension.

The effectiveness of the preparation is determined by counting, after dissection, the worms which have remained in the test animal, in comparison to untreated control animals, and calculating the percentage action therefrom.

Table 2 lists the active compounds and the minimum dosage which reduces the worm infection of the test animals by more than 90%, in comparison to related preparations.

The amount of active compound was administered orally as pure active compound in gelatine capsules.

The effectiveness is determined by quantitatively counting the worm eggs, excreted with the faeces, before and after the treatment.

Complete cessation of the excretion of eggs after the treatment denotes that the worms have been expelled or have been so damaged that they can no longer produce any eggs (effective dose).

Table 2

| Compound | | Minimum effective dose (Red. > 90%) in mg/kg |
|---|---|---|
| B1 | C₆H₅—S—C₆H₃(NH—CO—CH₃)—NH—C(=N—CO—OCH₃)—NH—CO—OCH₃ | 25 |
| B2 | C₆H₅—S—C₆H₃(NH—CO—CH₂—OCH₃)—NH—C(=N—CO—OCH₃)—NH—CO—OCH₃ | 25 |
| B3 | C₆H₅—S—C₆H₃(NH—CO—C₃H₇)—NH—C(=N—CO—OCH₃)—NH—CO—OC₂H₅ | 50 |
| B4 | C₆H₅—S—C₆H₃(NH—CO—CH₂—OCH₃)—NH—C(=N—COOCH₃)—NH—CO—OC₂H₅ | 50 |

Related preparations for comparison (known from DOS (German Published Specification) 2,117,293):

| Compound | Minimum effective dose (Red. > 90%) in mg/kg |
|---|---|
| C₆H₄(NH—CO—CH₃)—NH—C(=N—CO—OCH₃)—NH—CO—OCH₃ | > 500 |
| C₆H₄(NH—CO—C₂H₅)—NH—C(=N—CO—OCH₃)—NH—CO—OCH₃ | 500 |

Stomach and intestine worm test / sheep

Sheep experimentally infected with *Haemonchus contortus* or *Trichostrongylus colubriformis* were treated after the end of the pre-patency period of the parasites.

The active compounds tested and the effective dosages (minimum effective dose) can be seen from Table 3.

Table 3

| Compound | | Minimum effective dose (Red. > 90%) in mg/kg |
|---|---|---|
| C1 | 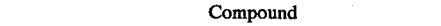 | Haemonchus cont. 5<br>Trichostrong. col. 5 |

Table 3-continued

| Compound | | Minimum effective dose (Red. > 90%) in mg/kg | |
|---|---|---|---|
| C2 | phenyl-O-phenyl-NH-C(=N-CO-OCH$_3$)-NH-CO-OCH$_3$; NH-CO-CH$_2$-CH$_3$ | Haemonchus cont.<br>Trichostrong. col. | 2.5<br>2.5 |
| C3 | phenyl-O-phenyl-NH-C(=N-CO-OCH$_3$)(NH-CO-OCH$_3$); NH-CO-CH$_2$-CH$_2$-CH$_3$ | Haemonchus cont.<br>Trichostrong. col. | 2.5<br>2.5 |
| C4 | phenyl-O-phenyl-NH-C(=N-CO-OCH$_3$)-NH-CO-C$_2$H$_5$; NH-CO-CH$_3$-CH$_2$ | Haemonchus cont.<br>Trichostrong. col. | 5<br>5 |
| C5 | phenyl-O-phenyl-NH-C(=N-CO-OCH$_3$)-NH-CO-C$_2$H$_5$; NH-CO-cyclohexyl | Haemonchus cont. | 5 |
| C6 | phenyl-S-phenyl-NH-C(=N-CO-OCH$_3$)-NH-CO-OCH$_3$; NH-CO-CH$_3$ | Haemonchus cont.<br>Trichostrong. col. | 2.5<br>2.5 |
| C7 | phenyl-S-phenyl-NH-C(=N-CO-OCH$_3$)(NH-CO-OCH$_3$); NH-CO-C$_2$H$_5$ | Haemonchus cont.<br>Trichostrong. col. | 2.5<br>2.5 |
| C8 | phenyl-S-phenyl-NH-C(=N-CO-OCH$_3$)-NH-CO-OCH$_3$; NH-CO-C$_3$H$_7$ | Haemonchus cont.<br>Trichostrong. col. | 0.5<br>1 |
| C9 | phenyl-S-phenyl-NH-C(=N-CO-OCH$_3$)(NH-CO-C$_2$H$_5$); NH-CO-CH$_3$ | Haemonchus cont.<br>Trichostrong. col. | 2.5<br>5 |
| C10 | H$_3$CO-phenyl-O-phenyl-NH-C(=N-CO-OCH$_3$)-NH-CO-OCH$_3$; NH-CO-CH$_3$ | Haemonchus cont. | 5 |
| C11 | phenyl-O-phenyl-NH-CO-C$_2$H$_5$; NH-C(=N-CO-OCH$_3$)-NH-CO-OCH$_3$ | Haemonchus cont.<br>Trichostrong. col. | 5<br>1 |

Table 3-continued

| Compound | | Minimum effective dose (Red. > 90%) in mg/kg | |
|---|---|---|---|
| C12 | Phenyl-S-C6H3(NH-C(=N-CO-OC2H5)-NH-CO-OCH3)(NH-CO-CH3) | Haemonchus cont.<br>Trichostrong. col. | 2.5<br>2.5 |
| C13 | Phenyl-O-C6H3(NH-CO-CH3)(NH-C(-NH-CO-C2H5)=N-CO-OCH3) | Trichostrong. col.<br>Haemonchus cont. | 5<br>10 |
| C14 | Phenyl-S-C6H3(NH-C(=N-CO-OCH3)-NH-CO-OCH3)(NH-CO-CH2-OCH3) | Haemonchus cont.<br>Trichostrong. col. | 0.5<br>1 |
| C15 | Phenyl-S-C6H3(NH-C(=N-COOCH3)-NH-CO-C2H5)(NH-CO-C2H5) | Haemonchus cont.<br>Trichostrong. col. | 2.5<br>2.5 |
| C16 | Phenyl-S-C6H3(NH-C(=N-CO-OCH3)-NH-CO-C2H5)(NH-CO-C3H7) | Haemonchus cont.<br>Trichostrong. col. | 2.5<br>2.5 |
| C17 | Phenyl-S-C6H3(NH-C(=N-CO-OCH3)-NH-CO-OC2H5)(NH-CO-CH2-OCH3) | Haemonchus cont.<br>Trichostrong. col. | 1<br>2.5 |
| C18 | (3-H3CO-C6H4)-O-C6H3(NH-C(=N-CO-OCH3)-NH-CO-OCH3)(NH-CO-C2H5) | Trichostrong. col. | 5 |
| C19 | CH3-CO-HN-C6H4-O-C6H3(NH-C(=N-CO-OCH3)-NH-CO-OCH3)(NH-CO-C2H5) | Haemonchus cont. | 2.5 |
| C20 | Phenyl-S-C6H3(NH-C(=N-CO-OCH3)-NH-CO-OCH3)(NH-CO-CH2-OC6H5) | Haemonchus | 2.5 |
| C21 | Phenyl-O-C6H3(NH-CO-C3H7)(NH-C(=N-COOCH3)-NH-CO-C2H5) | Trichostrong. col. | 5 |

Table 3-continued

| Compound | | Minimum effective dose (Red. > 90%) in mg/kg | |
|---|---|---|---|
| C22 | Ph—O—C6H3(NH—C(=N—CO—OCH3)—NH—CO—OCH3)(NH—CO—CH2—OCH3) | Haemonchus cont.<br>Trichostrong. col. | 2.5<br>2.5 |
| C23 | Ph—S—C6H3(NH—C(=N—CO—OCH3)—NH—CO—OCH3)(NH—CO—C5H11) | Haemonchus cont. | 1 |
| C24 | Ph—S—C6H3(NH—C(=N—CO—OCH3)—NH—CO—OCH3)(NH—CO—C4H9) | Haemonchus cont. | 1 |
| C25 | Ph—S—C6H3(NH—C(=N—CO—OCH3)—NH—CO—OCH3)(NH—CO—CH(CH3)2) | Haemonchus cont. | 2.5 |
| C26 | Ph—S—C6H3(NH—C(=N—CO—OCH3)—NH—CO—OCH3)(NH—CO—CH2—O—Ph) | Haemonchus cont.<br>Trichostrong. col. | 2.5<br>2.5 |
| C27 | Ph—S—C6H3(NH—C(=N—CO—OCH3)—NH—CO—OCH3)(NH—CO—CH2—OC2H5) | Haemonchus cont.<br>Trichostrong. col. | 1<br>1 |
| C28 | Ph—S(O)—C6H3(NH—C(=N—CO—OCH3)—NH—CO—OCH3)(NH—CO—C3H7) | Haemonchus cont.<br>Trichostrong. col. | 1<br>1 |
| C29 | Ph—S(O)—C6H3(NH—C(=N—CO—OCH3)—NH—CO—OCH3)(NH—CO—CH2—OCH3) | Haemonchus cont.<br>Trichostrong. col. | 0.5<br>1 |
| C30 | Ph—S(O)2—C6H3(NH—C(=N—CO—OCH3)—NH—CO—OCH3)(NH—CO—C3H7) | Haemonchus cont. | 1 |

Table 3-continued

| Compound | | Minimum effective dose (Red. > 90%) in mg/kg |
|---|---|---|
| C31 | CH$_3$—C$_6$H$_4$—S—C$_6$H$_3$(NH—CO—C$_3$H$_7$)—NH—C(=N—CO—OCH$_3$)—NH—CO—OCH$_3$ | Haemonchus cont. 5 |
| C32 | Cl—C$_6$H$_4$—S—C$_6$H$_3$(NH—CO—C$_3$H$_7$)—NH—C(=N—CO—OCH$_3$)—NH—CO—OCH$_3$ | Haemonchus cont. 5 |
| C33 | F—C$_6$H$_4$—S—C$_6$H$_3$(NH—CO—C$_3$H$_7$)—NH—C(=N—CO—OCH$_3$)—NH—CO—OCH$_3$ | Haemonchus cont. 2.5 |
| C34 | C$_6$H$_5$—S—C$_6$H$_3$(NH—CO—CH$_2$—OC$_2$H$_5$)—NH—C(=N—CO—OCH$_3$)—NH—CO—C$_2$H$_5$ | Haemonchus cont. 2.5 |

| Related preparations for comparison (known from DOS (German Published Specification) 2,117,293) | Minimum effective dose (Red. >90%) in mg/kg |
|---|---|
| C$_6$H$_4$(NH—CO—CH$_3$)—NH—C(=N—CO—OCH$_3$)—NH—CO—OCH$_3$ | Haemonchus cont. >100 Trichostrong. col. 50 |
| C$_6$H$_4$(NH—CO—C$_2$H$_5$)—NH—C(=N—CO—OCH$_3$)—NH—CO—OCH$_3$ | Haemonchus cont. 50 Trichostrong. col. 10 |

Ascarid test / dogs and rats

Dogs naturally or experimentally infected with *Toxascaris leonina* were given the amount of active compound administered orally as pure active compound in gelatine capsules.

The effectiveness is determined by counting the worms expelled after the treatment and, after dissection, the worms surviving in the animals, are calculated in percentage of worms expelled.

Rats experimentally infected with *Ascaris suum* were treated 2 to 4 days after infection. The amount of active compound was administered orally as an aqueous suspension.

The effectiveness of the preparation is determined by counting, after dissection, the worms which have remained in the test animal in comparison to untreated control animals and calculating the percentage action therefrom.

Table 4 lists the active compounds and the minimum dosage which reduces the worm infection of the test animals by more than 90%, in comparison to related preparations.

Table 4

| Compound | | Minimum effective dose (Red. 90%) in mg/kg |
|---|---|---|
| D1 | C$_6$H$_5$—O—C$_6$H$_3$(NH—CO—CH$_2$—CH$_2$—CH$_3$)—NH—C(=N—CO—OCH$_3$)—NH—CO—OCH$_3$ | *Toxascaris leonina* 25 |
| D2 | C$_6$H$_5$—S—C$_6$H$_3$(NH—CO—CH$_3$)—NH—C(—NH—CO—OCH$_3$)=N—CO—OCH$_3$ | *Ascaris suum-Larv.* 25 |

Table 4-continued

| Compound | | Minimum effective dose (Red. 90%) in mg/kg | |
|---|---|---|---|
| D3 | Ph—S—C6H3(NH—CO—CH3)—NH—C(=N—CO—OC2H5)—NH—CO—OCH3 | Ascaris suum-Larv. | 50 |
| D4 | Ph—S—C6H3(NH—CO—CH2—OCH3)—NH—C(N—CO—OCH3)(NH—CO—OC2H5) | Toxascaris / Ascaris suum-Larv. | 5 / 100 |
| D5 | Ph—S—C6H3(NH—CO—CH2—OCH3)—NH—C(N—CO—OCH3)(NH—CO—OCH3) | Toxascaris / Ascaris suum Larv. | 5 / 25 |
| D6 | Ph—S—C6H3(NH—CO—C2H5)—NH—C(N—CO—OCH3)(NH—CO—C2H5) | Ascaris suum Larv. | 50 |
| D7 | Ph—S—C6H3(NH—CO—C3H7)—NH—C(N—CO—OCH3)(NH—CO—OC2H5) | Ascaris suum Larv. | 50 |
| D8 | Ph—S—C6H3(NH—CO—CH3)—NH—C(N—CO—OCH3)(NH—CO—OC2H5) | Ascaris suum Larv. | 50 |

| Related preparation for comparison (known from DOS (German Published Specification) 2,117,293) | Minimum effective dose (Red. >90%) in mg/kg |
|---|---|
| 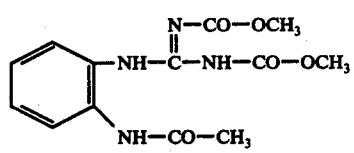 C6H4(NH—CO—CH3)—NH—C(=N—CO—OCH3)—NH—CO—OCH3 | inactive |
| 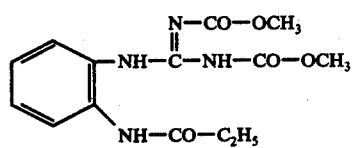 C6H4(NH—CO—C2H5)—NH—C(=N—CO—OCH3)—NH—CO—OCH3 | inactive |

*Aspiculuris tetraptera* / mice

Mice naturally infected with *Aspiculuris tetraptera* were treated after the end of the pre-patency period of the parasites.

The amount of active compound was administered orally as an aqueous suspension.

The effectiveness of the preparation is determined by counting, after dissection, the worms which have remained in the test animal, in comparison to untreated control animals, and calculating the percentage action therefrom. The results are shown in Table 5.

Table 5

| Compound | Minimum effective dose (Red. 90%) in mg/kg |
|---|---|

Table 5-continued

| | | Minimum effective dose (Red. >90%) in mg/kg |
|---|---|---|
| E1 | Ph–S–C₆H₃(NH–CO–CH₃)–NH–C(=N–CO–OCH₃)–NH–CO–OCH₃ | 50 |
| E2 | Ph–S–C₆H₃(NH–CO–C₂H₅)–NH–C(=N–CO–OCH₃)–NH–CO–C₂H₅ | 25 |
| E3 | Ph–S–C₆H₃(NH–CO–C₃H₇)–NH–C(=N–CO–OCH₃)–NH–CO–C₂H₅ | 25 |
| E4 | Ph–O–C₆H₃(NH–CO–C₂H₅)–NH–C(=N–CO–OCH₃)–NH–CO–OCH₃ | 50 |

Known preparation for comparison (known from DOS (German Published Specification) 2,117,293)

| | Minimum effective dose (Red. >90%) in mg/kg |
|---|---|
| C₆H₄(NH–CO–CH₃)–NH–C(=N–CO–OCH₃)–NH–CO–OCH₃ | inactive |

*Hymenolepis nana / mice*

Test animals experimentally infected with *H.nana* are treated after the end of the pre-patency of the parasites. The amount of active compound is administered orally as an aqueous suspension.

The effectiveness of the preparation is determined by counting, after dissection, the worms which have remained in the test animal in comparison to untreated control animals and calculating the percentage action therefrom. The results are shown in Table 6.

Table 6

| Compound | | Minimum effective dose (Red. > 90%) in mg/kg |
|---|---|---|
| F1 | Ph–S–C₆H₃(NH–CO–CH₃)–NH–C(=N–COOCH₃)–NH–CO–C₂H₅ | 500 |
| F2 | Ph–S–C₆H₃(NH–CO–CH₂–OCH₃)–NH–C(=N–CO–OCH₃)–NH–CO–OCH₃ | 500 |

The compounds of the invention are employed to combat helmintic infestations, both prophylactically and therapeutically, in humans and other animals through administration thereto of an anthelmintically effective amount of one or more compounds. Generally such an amount will range from about 0.1 mg/kg to about 50 mg/kg of body weight, depending upon the stage and severity of the infestation. This range is of course merely a guideline and the actual dose should be titrated to the recipient keeping in mind his age, general health and body weight, the response to treatment and the type of formulation. At times less than 0.1 mg/kg will suffice while at others more than 50 mg/kg can be indicated. The total daily dose thus will generally be from about 5 mg to about 5 g, although here again this is merely a guideline.

The compounds of the present invention are administered parenterally or orally in any of the usual pharmaceutical forms. These include solid and liquid oral unit dosage forms such as tablets, capsules, powders suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following examples will serve to further illustrate the compound of the invention and the methods of preparation without being a limitation on the scope thereof, the scope being defined solely by the appended claims.

EXAMPLE 1

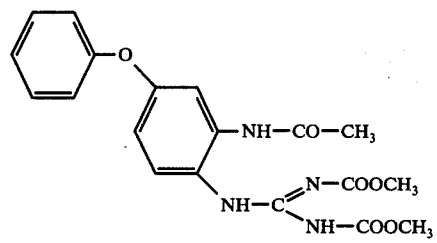

24.2 g (0.1 mol) of 2-amino-5-phenoxy-acetanilide of melting point 120° C together with 20.6 g (0.1 mol) of N,N'-bis-methoxycarbonyl-isothiourea-S-methyl-ether and 2.6 g (0.015 mol) of p-toluenesulphonic acid in 200 ml of absolute methanol are boiled for 3 hours with stirring under reflux. The mixture is then filtered hot and after cooling the N-(2acetamido-4-phenoxyphenyl)-N',N''-bis-methoxycarbonyl-guanidine which has crystallized out is filtered off, rinsed with ether and dried in a high vacuum; melting point 168° C, yield 27 g = 67.5% of theory.

Additional product can be obtained from the mother liquor.

The following reactants are allowed to react in a fashion analogous to Example 1 to yield the following products:
- 2-amino-5-phenoxy-acetanilide and N,N'-bis-ethoxycarbonylisothiourea-S-methyl-ether gave N-(2-acetamido-4-phenoxyphenyl)-N',N''-bis-ethoxycarbonyl-guanidine of melting point 159° C;
- 2-amino-5-phenoxy-acetanilide and N,N'-bis-isopropoxycarbonyl-isothiourea-S-methyl-ether gave N-(2-acetamido4-phenoxyphenyl)-N',N''-bis-isopropoxycarbonyl-guanidine of melting point 165° C;
- 2-amino-5-phenoxy-propionanilide of melting point 122° C and N,N'-bis-methoxycarbonyl-isothiourea-S-methyl-ether gave N-(2-propionamido-4-phenoxyphenyl)-N',N''-bis-methoxycarbonyl-guanidine of melting point 143° C;
- 2-amino-5-phenoxy-propionanilide and N,N'-bis-ethoxycarbonyl-isothiourea-S-methyl-ether gave N-(2-propionamido-4-phenoxyphenyl)-N',N''-bis-ethoxycarbonylguanidine of melting point 167° C;
- 2-amino-5-phenoxy-propionanilide and N,N'-bis-isopropoxycarbonyl-isothiourea-S-methyl-ether gave N-(2-propionamido-4-phenoxy-phenyl)-N',N''-bis-iso-propoxycarbonyl-guanidine of melting point 161° C;
- 2-amino-5-phenoxy-butyranilide of melting point 118° C and N,N'-bis-methoxycarbonyl-isothiourea-S-methyl-ether gave N-(2-butyramido-4-phenoxyphenyl)-N',N''-bismethoxycarbonyl-guanidine of melting point 136° C;
- 2-amino-5-phenoxy-butyranilide and N,N'-bis-ethoxycarbonyl-isothiourea-S-methyl-ether gave N-(2-butyramido4-phenoxyphenyl)-N', N''-bis-ethoxycarbonyl-guanidine of melting point 142° C;
- 2-amino-5-phenoxy-butyranilide and N,N'-bis-isopropoxycarbonyl-isothiourea-S-ether gave N-(2-butyramido-4-phenoxyphenyl)-N',N''-bis-isopropoxycarbonyl-guanidine of melting point 163° C;

2-amino-5-phenoxy-benzanilide of melting point 140° C and N,N'-bis-methoxycarbonyl-isothiourea-S-methyl-ether gave N-(2-benzamido-4-phenoxyphenyl)-N',N''-bis-methoxycarbonyl-guanidine of melting point 157° C;

2-amino-5-phenoxy-benzanilide and N,N'-bis-ethoxycarbonyl-isothiourea-S-methyl-ether gave N-(2-benzamido4-phenoxyphenyl)-N',N''-bis-ethoxycarbonyl-guanidine of melting point 141° C;

2-amino-5-phenoxy-benzanilide and N,N'-bis-isopropoxycarbonyl-isothiourea-S-methyl-ether gave N-(2-benzamido-4-phenoxyphenyl)-N',N''-bis-isopropoxycarbonyl-guanidine of melting point 188° C;

2-amino-5-phenoxy-cyclohexanecarboxylic acid anilide of melting point 142° C and N,N'-bis-methoxycarbonyl-isothiourea-S-methyl-ether gave N-(2-cyclohexanecarbonamido-4-phenoxy-phenyl)-N',N''-bis-methoxycarbonyl-guanidine of melting point 155° C;

2-amino-5-phenoxy-cyclohexanecarboxylic acid anilide and N,N'-bis-ethoxycarbonyl-isothiourea-S-methyl-ether gave N-(2-cyclohexanecarbonamido-4-phenoxy-phenyl)-N',N''-bis-ethoxycarbonyl-guanidine of melting point 132° C;

2-amino-5-phenoxy-methoxyacetanilide of melting point 93° C and N,N'-bis-methoxycarbonyl-isothiourea-S-methyl-ether gave N-(2-methoxyacetamido-4-phenoxy-phenyl)-N',N''bis-methoxycarbonyl-guanidine of melting point 145° C;

2-amino-5-(3-chloro-phenoxy)-acetanilide and N,N'-bis-methoxycarbonyl-isothiourea-S-methyl-ether gave N-[2acetamido-4-(3-chloro-phenoxy)-phenyl]-N',N''-bis-methoxycarbonyl-guanidine of melting point 160°–161° C;

2-amino-5-(3-chloro-phenoxy)-butyranilide and N,N'-bis-methoxy-carbonyl-isothiourea-S-methyl-ether gave N-[2-butyramido-4-(3-chloro-phenoxy)-phenyl]-N',N''-bis-methoxycarbonyl-guanidine of melting point 163° C;

2-amino-5-(4-chloro-phenoxy)-acetanilide of melting point 150°–151° C and N,N'-bis-methoxycarbonyl-isothiourea-S-methyl-ether gave N-[2-acetamido-4-(4-chlorophenoxy)-phenyl]-N',N''-bis-methoxycarbonyl-guanidine of melting point 170° C;

2-amino-5-(4-chloro-phenoxy)-butyranilide of melting point 101° C and N,N'-bis-methoxycarbonyl-isothiourea-S-methyl-ether gave N-[2-butyramido-4-(4-chloro-phenoxy)-phenyl]-N',N''-bis-methoxycarbonyl-guanidine of melting point 201° C;

2-amino-5-(3-fluoro-phenoxy)-butyranilide of melting point 121° C and N,N'-bis-methoxycarbonyl-isothiourea-S-methyl-ether gave N-[2-butyramido-4-(3-fluoro-phenoxy)-phenyl]-N',N''-bis-methoxycarbonyl-guanidine of melting point 138° C;

2-amino-5-(3-fluoro-phenoxy)-methoxyacetanilide of melting point 106° C and N,N'-bis-methoxy-carbonyl-isothiourea-S-methyl-ether gave N-[2-methoxyacetamido-4-(3-fluorophenoxy)-phenyl]-N',N''-bis-methoxycarbonyl-guanidine of melting point 148° C;

2-amino-5-(3-methoxy-phenoxy)-acetanilide of melting point 107°–108° C and N,N'-bis-methoxycarbonyl-isothiourea-S-methyl-ether gave N-[2-acetamido-4-(3-methoxy-phenoxy)-phenyl]-N',N''-bis-methoxycarbonyl-guanidine of melting point 164° C;

2-amino-5-(3-methoxy-phenoxy)-propionanilide of melting point 129°–130° C and N,N'-bis-methoxycarbonyl-isothiourea-S-methyl-ether gave N-[2-propionamido-4-(3-methoxy-phenoxy)-phenyl]-N',N''-bis-methoxycarbonyl-guanidine of melting point 133°–134° C;

2-amino-5-(4-methyl-phenoxy)-propionanilide of melting point 125° C and N,N'-bis-methoxycarbonyl-isothiourea-S-methyl-ether gave N-[2-propionamido-4-(4-methyl-phenoxy)-phenyl]-N',N''-bis-methoxycarbonyl-guanidine of melting point 165°–166° C;

2-amino-5-(4-methyl-phenoxy)-butyranilide of melting point 122° C and N,N'-bis-methoxycarbonyl-isothiourea-S-methyl-ether gave N-[2-butyramido-4-(4-methyl-phenoxy)-phenyl]-N',N''-bis-methoxycarbonyl-guanidine of melting point 161°–162° C;

2-amino-5-(4-acetamino-phenoxy)-propionanilide of melting point 200° C and N,N'-bis-methoxycarbonyl-isothiourea-S-methyl-ether gave N-[2-propionamido-4-(4-acetamido-do-phenoxy)-phenyl]-N',N''-bis-methoxycarbonly-guanidine of melting point 197°–199° C;

2-amino-5-(4-acetamino-phenoxy)-butyranilide of melting point 150° C and N,N'-bis-methoxycarbonyl-isothiourea-S-methyl-ether gave N-[2-butyramido-4-(4-acetamido-phenoxy)-phenyl]-N',N''-bis-methoxycarbonyl-guanidine of melting point 190° C;

2-amino-5-(4-cyano-phenoxy)-butyr-anilide and N,N'-bis-methoxycarbonyl-isothiourea-S-methyl-ether gave N-[2-butyramido-4-(4-cyano-phenoxy)-phenyl]-N',N''-bis-methoxycarbonyl-guanidine;

2-amino-5-(4-fluoro-phenoxy)-butyr-anilide and N,N'-bis-methoxycarbonyl-isothiourea-S-methyl-ether gave N-[2-butyramido-4-(4-fluoro-phenoxy)-phenyl]-N',N''-bis-methoxycarbonyl-guanidine;

2-amino-5-(4-acetyl-phenoxy)-butyr-anilide and N,N'-bis-methoxycarbonyl-isothiourea-S-methyl-ether gave N-[2-butyramido-4-(4-acetyl-phenoxy)-phenyl]-N',N''-bis-methoxycarbonyl-guanidine;

2-amino-5-(3-acetyl-phenoxy)-butry-anilide and N,N'-bis-methoxycarbonyl-isothiourea-S-methyl-ether gave N-[2-butyramido-4-(3-acetyl-phenoxy)-phenyl]-N',N''-bis-methoxycarbonyl-guanidine;

2-amino-5-(4-methylthio-phenoxy)-butyranilide and N,N'-bis-methoxycarbonyl-isothiourea-S-methyl-ether gave N-[2-butyramido-4-(4-methylthio-phenoxy)-phenyl]-N',N''-bis-methoxycarbonyl-guanidine;

2-amino-5-(3-trifluoromethyl-phenoxy)-butyranilide and N,N'-bis-methoxycarbonyl-isothiourea-S-methyl-ether gave N-[2-butyramido-4-(3-trifluoromethyl-phenoxy)-phenyl]-N',N''-bis-methoxycarbonyl-guanidine.

EXAMPLE 2

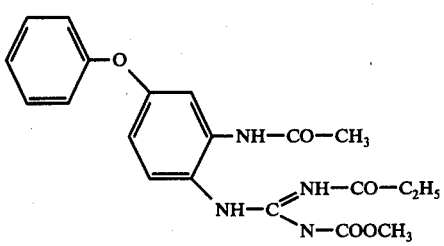

24.2 g (0.1 mol) of 2-amino-5-phenoxy-acetanilide together with 22 g (0.1 mol) of N-methoxycarbonyl-N'-propionyl-isothiourea-S-methyl-ether and 2.6 g (0.015 mol) of p-toluenesulphonic acid in 200 ml of absolute methanol are boiled for 3 hours with stirring under reflux. The mixture is then filtered hot and after cooling the N-(2-acetamido-4-phenoxy-phenyl)-N'-methoxycarbonyl-N''-propionyl-guanidine which has crystallized out is filtered off, well rinsed with ether and dried in a high vacuum; melting point 134° C, yield 20 g = 50% of theory. The yield can be increased by working up the mother liquor.

The following reactants are allowed to react in a fashion analogous to Example 2 to yield the following products:

2-amino-5-phenoxy-propion-anilide and N-methoxycarbonyl-N'-propionyl-isothiourea-S-methyl-ether gave N-(2-propionamido-4-phenoxy-phenyl)-N'-methoxycarbonyl-N''-propionyl-guanidine of melting point 132° C;

2-amino-5-phenoxy-butyranilide and N-methoxycarbonyl-N'-propionyl-isothiourea-S-methyl-ether gave N-(2-butyramido-4-phenoxy-phenyl)-N'-methoxycarbonyl-N''-propionyl-guanidine of melting point 125° C;

2-amino-5-phenoxy-benzanilide and N-methoxycarbonyl-N'-propionyl-isothiourea-S-methyl-ether gave N-(2-benzamido-4-phenoxy-phenyl)-N'-methoxycarbonyl-N''-propionyl-guanidine of melting point 151° C;

2-amino-5-phenoxy-cyclohexanecarboxylic acid anilide and N-methoxycarbonyl-N'-propionyl-isothiourea-S-methyl-ether gave N-(2-cyclohexane-carbonamido-4-phenoxy-phenyl)-N'-methoxycarbonyl-N''-propionyl-guanidine of melting point 139° C;

2-amino-5-phenoxy-acetanilide and N-ethoxycarbonyl-N'-benzoyl-isothiourea-S-methyl-ether gave N-(2-acetamido-4-phenoxy-phenyl)-N'-ethoxycarbonyl-N''-benzoyl-guanidine of melting point 179° C;

2-amino-5-phenoxy-butyranilide and N-methoxycarbonyl-N'-cyclohexylcarbonyl-isothiourea-S-methyl-ether gave N-(2-butyramido-4-phenoxy-phenyl)-N'-methoxycarbonyl-N''-cyclohexylcarbonyl-guanidine of melting point 146° C;

2-amino-5-phenoxy-butyranilide and N-methoxycarbonyl-N'-ethoxy-methylcarbonyl-isothiourea-S-methyl-ether gave N-(2-butyramido-4-phenoxy-phenyl)-N'-methoxy-carbonyl-N''-ethoxymethylcarbonyl-guanidine of melting point 137° C;

2-amino-5-(3-chloro-phenoxy)-acetanilide and N-methoxycarbonyl-N'-propionyl-isothiourea-S-methyl-ether gave N-[2-acetamido-4-(3-chloro-phenoxy)-phenyl]-N'-methoxy-carbonyl-N'''-propionyl-guanidine of melting point 163° C;

2-amino-5-(3-chloro-phenoxy)-butyranilide and N-methoxycarbonyl-N'-propionyl-isothiourea-S-methyl-ether gave N-[2-butyramido-4-(3-chloro-phenoxy)-phenyl]-N'-methoxycarbonyl-N''-propionyl-guanidine of melting point 163° C;

2-amino-5-(4-acetamido-phenoxy)-propion-anilide and N-methoxycarbonyl-N'-propionyl-isothiourea-S-methyl-ether gave N-[2-propionamido-4-(4-acetamido-phenoxy)-phenyl]-N'-methoxycarbonyl-N''-propionyl-guanidine of melting point 190° C;

2-amino-5-(4-acetamido-phenoxy)-butyranilide and N-methoxycarbonyl-N'-propionyl-isothiourea-S-methyl-ether gave N-[2-butyr-amido-4-(4-acetamido-phenoxy)-phenyl]-N'-methoxycarbonyl-N''-propionyl-guanidine of melting point 178–180° C;

2-amino-5-(4-methyl-phenoxy)-butyranilide and N-methoxycarbonyl-N'-propionyl-isothiourea-S-methyl-ether gave N-[2-butyramido-4-(4-methyl-phenoxy)-phenyl]-N'-methoxycarbonyl-N''-propionyl-guanidine of melting point 135° C.

EXAMPLE 3

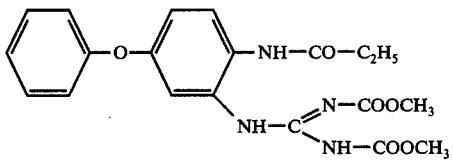

12.8 g (0.05 mol) of 2-amino-4-phenoxy-propionanilide (melting point 110–111° C) in 100 ml of methanol are heated with 10.3 g (0.05 mol) of N,N'-bis-methoxycarbonyl-isothiourea-S-methyl-ether, with the addition of 1 g of p-toluenesulphonic acid, for 3 hours under reflux. After cooling, the precipitate is filtered off and washed with ether, and after drying 11.1 g of N-(2-propionamido-5-phenoxy-phenyl)-N',N''-bis-methoxycarbonyl-guanidine of melting point 148–149° C are obtained.

EXAMPLE 4

In a fashion analogous to that described in Example 3, N,N'-bis-methoxycarbonyl-isothiourea-S-methyl ether and N-methoxycarbonyl-N'-propionyl-isothiourea-S-methyl ether are individually reacted with 2-amino-4-phenoxy-acetanilide to yield respectively N-(2-acetamido-5-phenoxyphenyl)-N',N''-bis-methoxycarbonyl-guanidine, m.p. 181–182° C and N-(2-acetamido5-phenoxyphenyl)-N'-methoxycarbonyl-N''-propionyl-guanidine, m.p. 161°–163° C.

By utilizing 2-amino-4-phenoxy-propionanilide with the foregoing isothiourea-S-methyl ethers, there are respectively obtained N-(2-propionamido-5-phenoxyphenyl)-N',N''-bis-methoxycarbonyl-guanidine, m.p. 164° C, and N-(2-propionamido-5-phenoxyphenyl)-N'-methoxycarbonyl-N''-propionyl-guanidine, m.p. 155°–156° C.

EXAMPLE 5

In a fashion analogous to that described in Example 3, the following compounds are obtained from the corresponding anilide and isothiourea-S-methyl-ether:

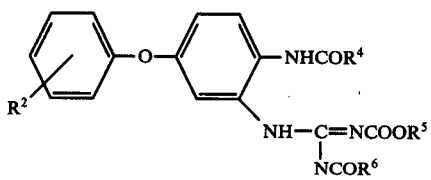

| R² | R⁴ | R⁵ | R⁶ |
|---|---|---|---|
| H | propyl | ethyl | ethoxy |
| H | methyl | methyl | ethoxy |
| H | methyl | methyl | methoxy |
| H | methyl | methyl | methoxy |
| H | methyl | methyl | allyloxy |
| H | methyl | methyl | propargyloxy |
| H | methyl | methyl | methoxy |
| H | methyl | methyl | methoxy |
| H | methoxymethyl | methyl | methoxy |
| H | phenoxymethyl | methyl | methoxy |
| H | propyl | methyl | propionyl |
| 4-methyl | propyl | methyl | methoxy |
| 3-methyl | propyl | methyl | methoxy |
| 2-methyl | propyl | methyl | methoxy |
| 4-chloro | propyl | methyl | methoxy |
| 3-chloro | propyl | methyl | methoxy |
| 4-ethyl | propyl | methyl | methoxy |
| 3-methylthio | propyl | methyl | methoxy |
| 3-methoxy | propyl | methyl | methoxy |
| 3-trifluoromethyl | propyl | methyl | methoxy |
| 3,5-dimethyl | propyl | methyl | methoxy |

EXAMPLE 6

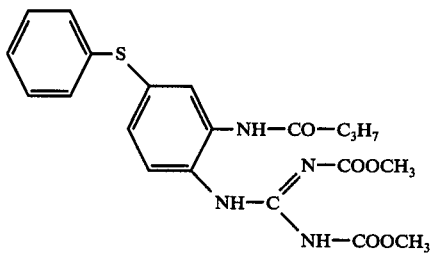

14.3 g (0.05 mol) of 2-amino-5-phenylthio-butyranilide (melting point 152° C) in 100 ml of methanol are heated with 10 g (0.05 mol) of N,N'-bis-methoxycarbonyl-isothiourea-S-methyl-ether, with addition of 1 g of p-toluenesulphonic acid, for 3 hours. After working up analogously to Example 3, 13.8 g of N-(2-butyramido-4-phenylthio-phenyl)-N',N''-bis-methoxycarbonyl-guanidine of melting point 155° C are obtained.

EXAMPLE 7

EXAMPLE 7

In a fashion analogous to that of Example 6, the appropriate N,N'-disubstituted isothiourea-S-methyl-ethers and 2-amino-5-phenylthio-anilides are reacted to give the following compounds:

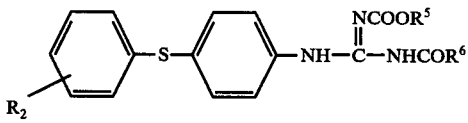

In this example and in Examples 8, 10, 12, 14, 16 and 18, R³ is hydrogen unless otherwise indicated by the listing of two substituents under R².

| R² | R⁴ | R⁵ | R⁶ | m.p. (° C) |
|---|---|---|---|---|
| H | CH₃ | CH₃ | OCH₃ | 160 |
| H | CH₃ | CH₃ | C₂H₅ | 131–132 |
| H | CH₃ | CH₃ | OC₂H₅ | 145–146 |
| H | C₂H₅ | CH₃ | OCH₃ | 176 |
| H | C₂H₅ | CH₃ | C₂H₅ | 130 |
| H | C₃H₇ | CH₃ | OC₂H₅ | 128 |
| H | C₃H₇ | CH₃ | C₂H₅ | 127 |
| H | C₄H₉ | CH₃ | OCH₃ | 137 |
| H | C₄H₉iso | CH₃ | OCH₃ | 145 |
| H | OC₂H₅ | CH₃ | OCH₃ | 159 |
| H | C₅H₁₁ | CH₃ | OCH₃ | 127 |
| H | C₅H₁₁ | CH₃ | C₂H₅ | 122 |
| H | C₄H₉ | CH₃ | C₂H₅ | 160 |
| H | —C(CH₃)=CH₂ | CH₃ | OCH₃ | 161 |
| H | CH(CH₃)₂ | CH₃ | OCH₃ | 161 |
| H | CH₂OCH₃ | CH₃ | OCH₃ | 129–130 |
| H | CH₂—OC₂H₅ | CH₃ | OCH₃ | 119 |
| H | CH₂OC₆H₅ | CH₃ | OCH₃ | 144–146 |
| 4-CH₃ | C₃H₇ | CH₃ | OCH₃ | 171 |
| 2-Cl | C₂H₅ | CH₃ | OCH₃ | 144 |
| 4-Br | C₃H₇ | CH₃ | OCH₃ | 176 |
| 4-C₂H₅ | C₃H₇ | CH₃ | OCH₃ | 167 |
| 2,5-(OCH₃)₂ | C₃H₇ | CH₃ | OCH₃ | 142 |
| 4-CH₃ | C₃H₇ | CH₃ | C₂H₅ | 110 |
| 4-Cl | C₃H₇ | CH₃ | OCH₃ | 176 |
| 4-Cl | C₃H₇ | CH₃ | C₂H₅ | 155 |
| 2-Cl | C₃H₇ | CH₃ | OCH₃ | 154 |
| 2-Cl | CH₂OCH₃ | CH₃ | OCH₃ | 138 |
| 4-Br | C₂H₅ | CH₃ | OCH₃ | 158 |
| 3-CH₃,4-Br | C₃H₇ | CH₃ | OCH₃ | 170 |
| 3-CH₃,4-Br | CH₂OCH₃ | CH₃ | OCH₃ | 141 |
| 4-C₂H₅ | C₂H₅ | CH₃ | OCH₃ | 155 |
| 4-C₂H₅ | CH₂OCH₃ | CH₃ | OCH₃ | 126 |
| 3-CF₃ | CH₂OCH₃ | CH₃ | OCH₃ | 120 |
| 4-OCH₃ | CH₂OCH₃ | CH₃ | OCH₃ | 131 |
| 2-OC₂H₉ | C₃H₇ | CH₃ | OCH₃ | 128 |
| 2-OC₂H₅ | CH₂OCH₃ | CH₃ | OCH₃ | 110 |
| 2-COOCH₃ | C₃H₇ | CH₃ | OCH₃ | 138 |
| 2-COOCH₃ | C₂H₅ | CH₃ | OCH₃ | 158 |
| 2-COOCH₃ | CH₂OCH₃ | CH₃ | OCH₃ | 135 |
| H | CH₂OCH₃ | CH₃ | OC₂H₅ | 125–127 |
| H | CH₂OC₆H₅ | CH₃ | C₂H₅ | 138–140 |
| H | CH₂—O—C₂H₅ | CH₃ | C₂H₅ | 111 |
| 4-OCH₃ | C₃H₇ | CH₃ | OCH₃ | 185 |
| 3-OCH₃ | C₃H₇ | CH₃ | OCH₃ | 160 |
| 4-F | CH₂OCH₃ | CH₃ | OCH₃ | 127 |
| 4-F | C₃H₇ | CH₃ | OCH₃ | 155 |
| 4-F | C₃H₇ | CH₃ | C₂H₅ | 136–137 |
| 4-Br | CH₂—O—CH₃ | CH₃ | OCH₃ | 114 |
| 3-Cl | C₃H₇ | CH₃ | OCH₃ | 129 |
| 3-Cl | CH₂—O—CH₃ | CH₃ | OCH₃ | 124 |
| 4-C(CH₃)₃ | C₃H₇ | CH₃ | OCH₃ | 169 |

EXAMPLE 8

In a fashion analogous to that described in Example 6, the following compounds are obtained from the corresponding anilide and isothiourea-S-methyl-ether:

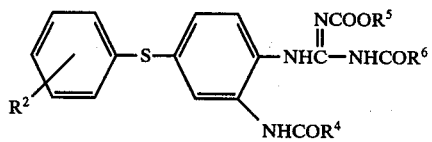

| R² | R⁴ | R⁵ | R⁶ |
|---|---|---|---|
| H | ethyl | methyl | ethoxy |
| H | methyl | methyl | methoxy |
| H | hexyl | methyl | methoxy |
| H | ethyl | methyl | allyloxy |
| H | ethyl | methyl | propargyloxy |
| H | ethyl | methyl | 2-methylprop-2-enyloxy |
| H | ethyl | allyl | allyloxy |
| H | cyclopentyl | methyl | methoxy |
| H | cyclohexyl | methyl | methoxy |
| 4-methyl | propyl | methyl | methoxy |
| 3-methyl | propyl | methyl | methoxy |
| 2-methyl | propyl | methyl | methoxy |
| 4-chloro | ethyl | methyl | methoxy |
| 3-chloro | ethyl | methyl | methoxy |
| 4-acetamido | ethyl | methyl | methoxy |

-continued

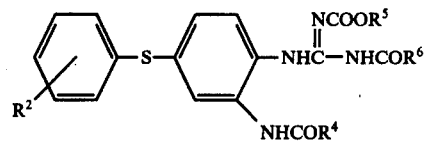

| $R^2$ | $R^4$ | $R^5$ | $R^6$ |
|---|---|---|---|
| 3,4-dichloro | propyl | methyl | methoxy |
| 4-butyl | propyl | methyl | methoxy |
| 3-methyl-4-bromo | ethyl | methyl | methoxy |
| 3-trifluoromethyl | propyl | methyl | methoxy |
| 4-butyl | methoxymethyl | methyl | methoxy |
| 3-methoxy | methoxymethyl | methyl | methoxy |
| 2,4-dimethyl | propyl | methyl | methoxy |
| 3-methoxy | propyl | methyl | methoxy |
| 4-methylthio | propyl | methyl | methoxy |
| 2-ethoxy | ethyl | methyl | methoxy |
| 3-methyl-4-bromo | ethyl | methyl | methoxy |
| 3-trifluoromethyl | ethyl | methyl | methoxy |
| 4-acetyl | ethyl | methyl | methoxy |
| 3-acetyl | ethyl | methyl | methoxy |
| 4-butynyl | ethyl | methyl | methoxy |
| 4-carbomethoxyamino | ethyl | methyl | methoxy |
| 4-cyano | ethyl | methyl | methoxy |
| 3-cyano | ethyl | methyl | methoxy |

EXAMPLE 9

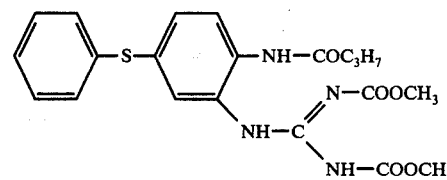

Using the method described in Example 3, 14.3 g (0.05 mol) of 2-amino-4-phenylthio-butyranilide and 10.3 g (0.05 mol) of N,N'-bis-methoxycarbonyl-isothiourea-S-methyl-ether give 14.5 g of N-(2-butyramido-5-phenylthio-phenyl)-N',N''-bis-methoxycarbonyl-guanidine of melting point 164°–166° C.

EXAMPLE 10

In a fashion analogous to that described in Example 9 using the appropriate N,N'-disubstituted isothiourea-S-methyl ethers and 2-amino-4-phenyl-thioanilides, the following compounds are obtained:

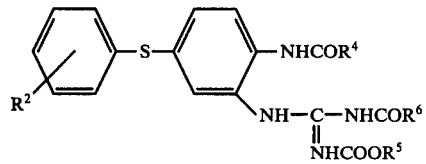

| $R^2$ | $R^4$ | $R^5$ | $R^6$ |
|---|---|---|---|
| H | $CH_3$ | $CH_3$ | $OCH_3$ |
| H | $CH_3$ | $CH_3$ | $C_2H_5$ |
| H | $CH_3$ | $CH_3$ | $OC_2H_5$ |
| H | $C_2H_5$ | $CH_3$ | $OCH_3$ |
| H | $C_2H_5$ | $CH_3$ | $C_2H_5$ |
| H | $C_2H_5$ | $CH_3$ | $OC_2H_5$ |
| H | $C_3H_7$ | $CH_3$ | $OC_2H_5$ |
| H | $C_3H_7$ | $CH_3$ | $C_2H_5$ |
| H | $C_4H_9$ | $CH_3$ | $OCH_3$ |
| H | $C_4H_9$iso | $CH_3$ | $OCH_3$ |
| H | $OCH_3$ | $CH_3$ | $OCH_3$ |
| H | $OC_2H_5$ | $CH_3$ | $OCH_3$ |
| H | $C_5H_{11}$ | $CH_3$ | $OCH_3$ |
| H | $C_6H_{13}$ | $CH_3$ | $OCH_3$ |
| H | $C_2H_5$ | $CH_3$ | $OCH_2-CH=CH_2$ |
| H | $C_2H_5$ | $CH_3$ | $OCH_2-C\equiv CH$ |
| H | $C_2H_5$ | $CH_3$ | $OCH_2-C(CH_3)=CH_2$ |
| H | $C_2H_5$ | $CH_2-CH=CH_2$ | $OCH_2-CH=CH_2$ |
| H | | $CH_3$ | $OCH_3$ |
| H |  | $CH_3$ | $OCH_3$ |
| H | $CH_2OCH_3$ | $CH_3$ | $OCH_3$ |
| H | $CH_2OC_6H_5$ | $CH_3$ | $OCH_3$ |
| 4-$CH_3$ | $C_3H_7$ | $CH_3$ | $OCH_3$ |
| 3-$CH_3$ | $C_3H_7$ | $CH_3$ | $OCH_3$ |
| 2-$CH_3$ | $C_3H_7$ | $CH_3$ | $OCH_3$ |
| 4-Cl | $C_2H_5$ | $CH_3$ | $OCH_3$ |
| 3-Cl | $C_2H_5$ | $CH_3$ | $OCH_3$ |
| 2-Cl | $C_2H_5$ | $CH_3$ | $OCH_3$ |
| 4-$NHCOCH_3$ | $C_2H_5$ | $CH_3$ | $OCH_3$ |
| 4-Br | $C_3H_7$ | $CH_3$ | $OCH_3$ |
| 3,4-$Cl_2$ | $C_3H_7$ | $CH_3$ | $OCH_3$ |
| 4-$C_4H_9$ | $C_3H_7$ | $CH_3$ | $OCH_3$ |
| 4-$C_2H_5$ | $C_3H_7$ | $CH_3$ | $OCH_3$ |
| 3,5-$(CH_3)_2$ | $C_3H_7$ | $CH_3$ | $OCH_3$ |
| 2,4-$(CH_3)_2$ | $C_3H_7$ | $CH_3$ | $OCH_3$ |
| 3-$OC_2H_5$ | $C_3H_7$ | $CH_3$ | $OCH_3$ |
| 4-$OCH_3$ | $C_3H_7$ | $CH_3$ | $OCH_3$ |
| 3-$OCH_3$ | $C_3H_7$ | $CH_3$ | $OCH_3$ |
| 4-$SCH_3$ | $C_3H_7$ | $CH_3$ | $OCH_3$ |
| 2-$OC_2H_5$ | $C_2H_5$ | $CH_3$ | $OCH_3$ |

-continued

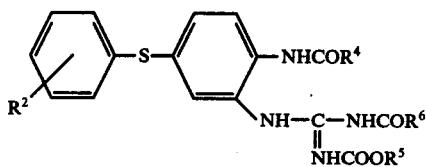

| R² | R⁴ | R⁵ | R⁶ |
|---|---|---|---|
| 3-CH₃, 4-Br | C₂H₅ | CH₃ | OCH₃ |
| 3-CF₃ | C₂H₅ | CH₃ | OCH₃ |
| 4-F | C₂H₅ | CH₃ | OCH₃ |
| 4-CH₃CO | C₂H₅ | CH₃ | OCH₃ |
| 3-CH₃CO | C₂H₅ | CH₃ | OCH₃ |
| 4-C₃H₇CO | C₂H₅ | CH₃ | OCH₃ |
| 4-NHCOOCH₃ | C₂H₅ | CH₃ | OCH₃ |
| 4-CN | C₂H₅ | CH₃ | OCH₃ |
| 3-CN | C₂H₅ | CH₃ | OCH₃ |

EXAMPLE 11

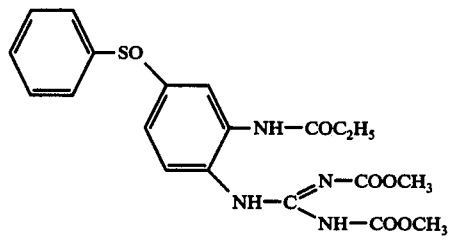

Using the method described in Example 3, 14.2 g (0.05 mol) of 2-amino-5-phenylsulphinyl-propionanilide and 10.3 g (0.05 mol) of N,N'-bis-methoxycarbonyl-isothiourea-S-methyl-ether give 12.7 g of N-(2-propionamido-4-phenylsulphinyl-phenyl)-N',N''-bis-methoxycarbonyl-guanidine of melting point 193°–195° C.

Utilizing 2-amino-5-phenylsulphinylbutyranilide and 2-amino-5-phenylsulphinyl-methoxyacetanilide, there are obtained N-(2-butyramido-4-phenylsulphinyl-phenyl)-N',N''-bis-methoxycarbonyl-guanidine, m.p. 186° C, and N-(2-methoxyacetamido-4-phenylsulfinyl-phenyl)-N',N''-bis-methoxycarbonyl-guanidine, m.p. 135°–136° C, respectively.

EXAMPLE 12

In a fashion analogous to Example 11 the corresponding N,N'-disubstituted isothiourea-S-methyl-ethers and 2-amino-5-phenylsulfphinylanilides are reacted to yield the following compounds:

| R² | R⁴ | R⁵ | R⁶ |
|---|---|---|---|
| H | CH₃ | CH₃ | OCH₃ |
| H | CH₃ | CH₃ | C₂H₅ |
| H | CH₃ | CH₃ | OC₂H₅ |
| H | C₂H₅ | CH₃ | C₂H₅ |
| H | C₂H₅ | CH₃ | OC₂H₅ |
| H | C₃H₇ | CH₃ | OC₂H₅ |
| H | C₃H₇ | CH₃ | C₂H₅ |
| H | C₄H₉ | CH₃ | OCH₃ |
| H | C₄H₉iso | CH₃ | OCH₃ |
| H | OCH₃ | CH₃ | OCH₃ |
| H | OC₂H₅ | CH₃ | OCH₃ |
| H | C₅H₁₁ | CH₃ | OCH₃ |
| H | C₆H₁₃ | CH₃ | OCH₃ |
| H | C₂H₅ | CH₃ | OCH₂—CH=CH₂ |
| H | C₂H₅ | CH₃ | OCH₂—C≡CH |
| H | C₂H₅ | CH₃ | OCH₂—C(CH₃)=CH₂ |
| H | C₂H₅ | CH—CH=CH₂ | OCH₂—CH=CH₂ |
| H | | CH₃ | OCH₃ |
| H | | CH₃ | OCH₃ |
| H | CH₂OC₆H₅ | CH₃ | OCH₃ |
| 4-CH₃ | C₃H₇ | CH₃ | OCH₃ |
| 3-CH₃ | C₃H₇ | CH₃ | OCH₃ |
| 2-CH₃ | C₃H₇ | CH₃ | OCH₃ |
| 4-Cl | C₂H₅ | CH₃ | OCH₃ |
| 3-Cl | C₂H₅ | CH₃ | OCH₃ |
| 2-Cl | C₂H₅ | CH₃ | OCH₃ |
| 4-NHCOCH3 | C₂H₅ | CH₃ | OCH₃ |
| 4-Br | C₃H₇ | CH₃ | OCH₃ |
| 3,4-Cl₂ | C₃H₇ | CH₃ | OCH₃ |
| 4-C₄H₉ | C₃H₇ | CH₃ | OCH₃ |
| 4-C₂H₅ | C₃H₇ | CH₃ | OCH₃ |

-continued

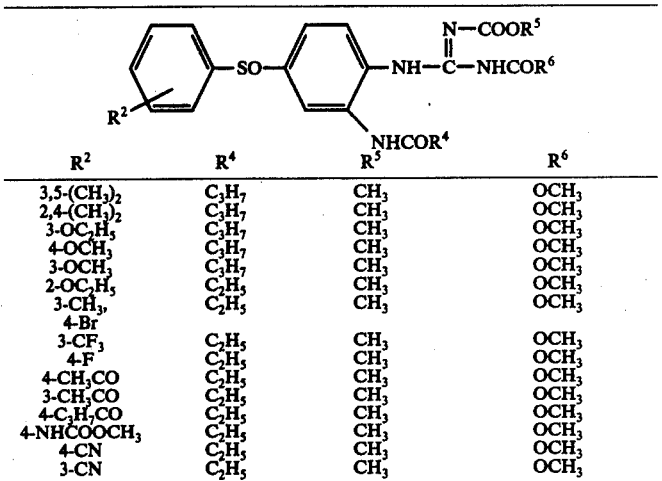

| R² | R⁴ | R⁵ | R⁶ |
|---|---|---|---|
| 3,5-(CH₃)₂ | C₃H₇ | CH₃ | OCH₃ |
| 2,4-(CH₃)₂ | C₃H₇ | CH₃ | OCH₃ |
| 3-OC₂H₅ | C₃H₇ | CH₃ | OCH₃ |
| 4-OCH₃ | C₃H₇ | CH₃ | OCH₃ |
| 3-OCH₃ | C₃H₇ | CH₃ | OCH₃ |
| 2-OC₂H₅ | C₃H₇ | CH₃ | OCH₃ |
| 3-CH₃, 4-Br | C₂H₅ | CH₃ | OCH₃ |
| 3-CF₃ | C₂H₅ | CH₃ | OCH₃ |
| 4-F | C₂H₅ | CH₃ | OCH₃ |
| 4-CH₃CO | C₂H₅ | CH₃ | OCH₃ |
| 3-CH₃CO | C₂H₅ | CH₃ | OCH₃ |
| 4-C₃H₇CO | C₂H₅ | CH₃ | OCH₃ |
| 4-NHCOOCH₃ | C₂H₅ | CH₃ | OCH₃ |
| 4-CN | C₂H₅ | CH₃ | OCH₃ |
| 3-CN | C₂H₅ | CH₃ | OCH₃ |

EXAMPLE 13

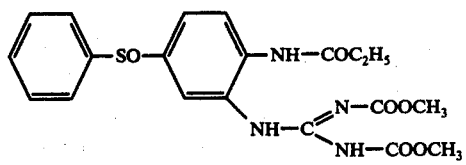

EXAMPLE 14

Using the method described in Example 3, 14.2 g (0.05 mol) of 2-amino-4-phenylsulphinyl-propionanilide and 10.3 g (0.05 mol) of N,N'-bis-methoxycarbonyl-isothiourea-S-methyl-ether give 12.7 g of N-(2-propionamido-5-phenylsulphinylphenyl)-N',N''-bis-methoxycarbonyl-guanidine.

In a fashion analogous to Example 13 the corresponding N,N'-disubstituted isothiourea-S-methyl-ethers and 2-amino-4-phenylsulphinyl-anilides are reacted to yield the following compounds:

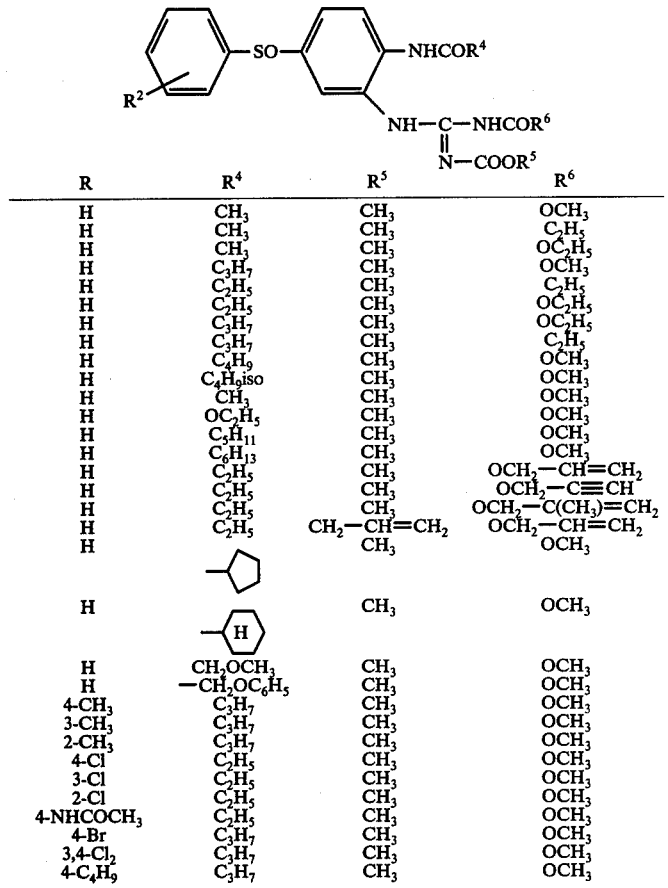

| R | R⁴ | R⁵ | R⁶ |
|---|---|---|---|
| H | CH₃ | CH₃ | OCH₃ |
| H | CH₃ | CH₃ | C₂H₅ |
| H | CH₃ | CH₃ | OC₂H₅ |
| H | C₃H₇ | CH₃ | OCH₃ |
| H | C₂H₅ | CH₃ | C₂H₅ |
| H | C₂H₅ | CH₃ | OC₂H₅ |
| H | C₃H₇ | CH₃ | OC₃H₇ |
| H | C₃H₇ | CH₃ | C₂H₅ |
| H | C₄H₉ | CH₃ | OCH₃ |
| H | C₄H₉iso | CH₃ | OCH₃ |
| H | CH₃ | CH₃ | OCH₃ |
| H | OC₂H₅ | CH₃ | OCH₃ |
| H | C₅H₁₁ | CH₃ | OCH₃ |
| H | C₆H₁₃ | CH₃ | OCH₃ |
| H | C₂H₅ | CH₃ | OCH₂—CH=CH₂ |
| H | C₂H₅ | CH₃ | OCH₂—C≡CH |
| H | C₂H₅ | CH₃ | OCH₂—C(CH₃)=CH₂ |
| H | C₂H₅ | CH₂—CH=CH₂ | OCH₂—CH=CH₂ |
| H | cyclopentyl | CH₃ | OCH₃ |
| H | cyclohexyl | CH₃ | OCH₃ |
| H | CH₂OCH₃ | CH₃ | OCH₃ |
| H | —CH₂OC₆H₅ | CH₃ | OCH₃ |
| 4-CH₃ | C₃H₇ | CH₃ | OCH₃ |
| 3-CH₃ | C₃H₇ | CH₃ | OCH₃ |
| 2-CH₃ | C₃H₇ | CH₃ | OCH₃ |
| 4-Cl | C₂H₅ | CH₃ | OCH₃ |
| 3-Cl | C₂H₅ | CH₃ | OCH₃ |
| 2-Cl | C₂H₅ | CH₃ | OCH₃ |
| 4-NHCOCH₃ | C₂H₅ | CH₃ | OCH₃ |
| 4-Br | C₃H₇ | CH₃ | OCH₃ |
| 3,4-Cl₂ | C₃H₇ | CH₃ | OCH₃ |
| 4-C₄H₉ | C₃H₇ | CH₃ | OCH₃ |

-continued

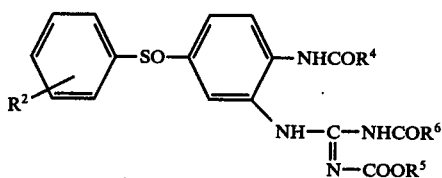

| R | R⁴ | R⁵ | R⁶ |
|---|---|---|---|
| 4-C₂H₅ | C₃H₇ | CH₃ | OCH₃ |
| 3,5-(CH₃)₂ | C₃H₇ | CH₃ | OCH₃ |
| 2,4-(CH₃)₂ | C₃H₇ | CH₃ | OCH₃ |
| 3-OC₂H₅ | C₃H₇ | CH₃ | OCH₃ |
| 4-OCH₃ | C₃H₇ | CH₃ | OCH₃ |
| 3-OCH₃ | C₃H₇ | CH₃ | OCH₃ |
| 4-SCH₃ | C₃H₇ | CH₃ | OCH₃ |
| 2-OC₂H₅ | C₂H₅ | CH₃ | OCH₃ |
| 3-CH₃, 4-Br | C₂H₅ | CH₃ | OCH₃ |
| 3-CF₃ | C₂H₅ | CH₃ | OCH₃ |
| 4-F | C₂H₅ | CH₃ | OCH₃ |
| 4-CH₃CO | C₂H₅ | CH₃ | OCH₃ |
| 3-CH₃CO | C₂H₅ | CH₃ | OCH₃ |
| 4-C₃H₇CO | C₂H₅ | CH₃ | OCH₃ |
| 4-NHCOOCH₃ | C₂H₅ | CH₃ | OCH₃ |
| 4-CN | C₂H₅ | CH₃ | OCH₃ |
| 3-CN | C₂H₅ | CH₃ | OCH₃ |

EXAMPLE 15

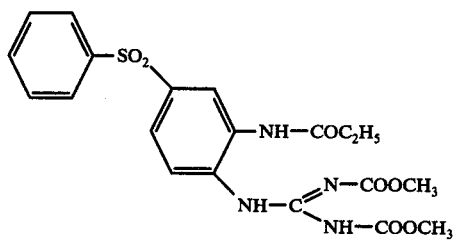

Using the method described in Example 3, 14.4 g (0.05 mol) of 2-amino-5-phenylsulphonyl-propionanilide of melting point 137° C and 10.3 g (0.05 mol) of N,N'-bis-methoxycarbonylisothiourea-S-methyl-ether give 12.7 g of N-(2-propionamido-4-phenylsulphonylphenyl)-N',N''-bis-methoxycarbonyl-guanidine of melting point 197° C.

Substituting 2-amino-5-phenylsulphonylbutyranilide and 2-amino-5-phenylsulphonylmethoxyacetanilide, there are obtained N-(2-butyrylamido-4-phenylsulphonylphenyl)-N',N''-bis-methoxycarbonyl-guanidine, m.p. 180° C, and N-(2-methoxyacetamido-4-phenylsulphonylphenyl)-N',N''-bis-methoxycarbonyl-guanidine, m.p. 142° C.

EXAMPLE 16

In a fashion analogous to Example 15 to corresponding N,N'-disubstituted isothiourea-S-methyl-ethers and 2-amino-5-phenylsulphonylanilides are reacted to yield the following compounds:

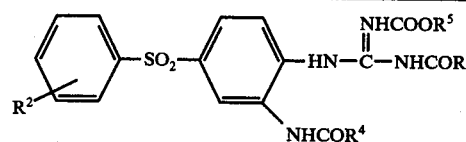

| R² | R⁴ | R⁵ | R⁶ |
|---|---|---|---|
| H | CH₃ | CH₃ | OCH₃ |
| H | CH₃ | CH₃ | C₂H₅ |
| H | CH₃ | CH₃ | OC₂H₅ |
| H | C₂H₅ | CH₃ | C₂H₅ |
| H | C₂H₅ | CH₃ | OC₂H₅ |
| H | C₃H₇ | CH₃ | OC₂H₅ |
| H | C₃H₇ | CH₃ | C₂H₅ |
| H | C₄H₉ | CH₃ | OCH₃ |
| H | C₄H₉iso | CH₃ | OCH₃ |
| H | OCH₃ | CH₃ | OCH₃ |
| H | OC₂H₅ | CH₃ | OCH₃ |
| H | C₅H₁₁ | CH₃ | OCH₃ |
| H | C₆H₁₃ | CH₃ | OCH₃ |
| H | C₂H₅ | CH₃ | OCH₂—CH=CH₂ |
| H | C₂H₅ | CH₃ | OCH₂—C≡CH |
| H | C₂H₅ | CH₃ | OCH₂—C(CH₃)=CH₂ |
| H | C₂H₅ | CH₂—CH=CH₂ | OCH₂—CH=CH₂ |
| H |  | CH₃ | OCH₃ |

-continued

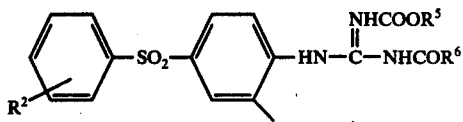

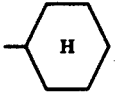

| R² | R⁴ | R⁵ | R⁶ |
|---|---|---|---|
| H | | CH₃ | OCH₃ |
| H | cyclohexyl | | |
| H | CH₂OC₆H₅ | CH₃ | OCH₃ |
| 4-CH₃ | C₃H₇ | CH₃ | OCH₃ |
| 3-CH₃ | C₃H₇ | CH₃ | OCH₃ |
| 2-CH₃ | C₃H₇ | CH₃ | OCH₃ |
| 4-Cl | C₂H₅ | CH₃ | OCH₃ |
| 3-Cl | C₂H₅ | CH₃ | OCH₃ |
| 2-Cl | C₂H₅ | CH₃ | OCH₃ |
| 4-NHCOCH₃ | C₂H₅ | CH₃ | OCH₃ |
| 4-Br | C₃H₇ | CH₃ | OCH₃ |
| 3,4-Cl₂ | C₃H₇ | CH₃ | OCH₃ |
| 4-C₄H₉ | C₃H₇ | CH₃ | OCH₃ |
| 4-C₂H₅ | C₃H₇ | CH₃ | OCH₃ |
| 3,5-(CH₃)₂ | C₃H₇ | CH₃ | OCH₃ |
| 2,4-(CH₃)₂ | C₃H₇ | CH₃ | OCH₃ |
| 3-OC₂H₅ | C₃H₇ | CH₃ | OCH₃ |
| 4-OCH₃ | C₃H₇ | CH₃ | OCH₃ |
| 3-OCH₃ | C₃H₇ | CH₃ | OCH₃ |
| 2-OC₂H₅ | C₂H₅ | CH₃ | OCH₃ |
| 3-CH₃, 4-Br | C₂H₅ | CH₃ | OCH₃ |
| 3-CF₃ | C₂H₅ | CH₃ | OCH₃ |
| 4-F | C₂H₅ | CH₃ | OCH₃ |
| 4-CH₃CO | C₂H₅ | CH₃ | OCH₃ |
| 3-CH₃CO | C₂H₅ | CH₃ | OCH₃ |
| 4-C₃H₇CO | C₂H₅ | CH₃ | OCH₃ |
| 4-NHCOOCH₃ | C₂H₅ | CH₃ | OCH₃ |
| 4-CN | C₂H₅ | CH₃ | OCH₃ |
| 3-CN | C₂H₅ | CH₃ | OCH₃ |

EXAMPLE 17

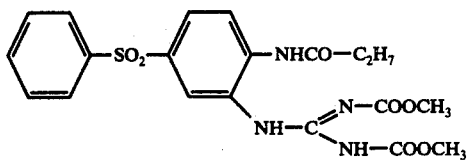

14.4 g (0.05 mol) of 2-amino-4-phenylsulphonyl-butyranilide (melting point 143°-145°) in 100 ml of methanol are heated with 10.3 g (0.05 mol) of N,N'-bis-methoxycarbonyl-isothiourea-S-methyl-ether, with addition of 1 g of p-toluenesulphonic acid, for 3 hours. After working up analogously to Example 3, 15.8 g of N-(2-butyramido-5-phenylsulphonyl-phenyl)-N',N''-bis-methoxycarbonyl-guanidine of melting point 173° C are obtained.

EXAMPLE 18

In a fashion analogous to Example 17, the corresponding N,N'-disubstituted isothiourea-S-methyl-ethers and 2-amino-5-phenylsulphonylanilides are reacted to yield the following compounds:

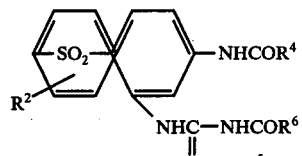

| R² | R⁴ | R⁵ | R⁶ |
|---|---|---|---|
| H | CH₃ | CH₃ | OCH₃ |
| H | CH₃ | CH₃ | C₂H₅ |
| H | CH₃ | CH₃ | OC₂H₅ |
| H | C₂H₅ | CH₃ | OCH₃ |
| H | C₂H₅ | CH₃ | C₂H₅ |
| H | C₂H₅ | CH₃ | OC₂H₅ |
| H | C₂H₅ | CH₃ | OC₂H₅ |
| H | C₃H₇ | CH₃ | C₂H₅ |
| H | C₃H₇ | CH₃ | C₂H₅ |
| H | C₄H₉ | CH₃ | OCH₃ |
| H | C₄H₉iso | CH₃ | OCH₃ |
| H | OCH₃ | CH₃ | OCH₃ |
| H | OC₂H₅ | CH₃ | OCH₃ |
| H | C₅H₁₁ | CH₃ | OCH₃ |
| H | C₆H₁₃ | CH₃ | OCH₃ |
| H | C₂H₅ | CH₃ | OCH₂—CH=CH₂ |
| H | C₂H₅ | CH₃ | OCH₂—C≡CH |
| H | C₂H₅ | CH₃ | OCH₂—C(CH₃)=CH₂ |

-continued

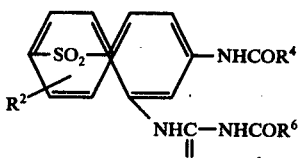

| $R^2$ | $R^4$ | $R^5$ | $R^6$ |
|---|---|---|---|
| H | $C_2H_5$ | $CH_2-CH=CH_2$ | $OCH_2-CH=CH_2$ |
| H |  | $CH_3$ | $OCH_3$ |
| H | (cyclopentyl) | $CH_3$ | $OCH_3$ |
| H | (cyclohexyl) |  |  |
| H | $CH_2OCH_3$ | $CH_3$ | $OCH_3$ |
| H | $-CH_2OC_6H_5$ | $CH_3$ | $OCH_3$ |
| 4-$CH_3$ | $C_3H_7$ | $CH_3$ | $OCH_3$ |
| 3-$CH_3$ | $C_3H_7$ | $CH_3$ | $OCH_3$ |
| 2-$CH_3$ | $C_3H_7$ | $CH_3$ | $OCH_3$ |
| 4-Cl | $C_3H_7$ | $CH_3$ | $OCH_3$ |
| 3-Cl | $C_3H_5$ | $CH_3$ | $OCH_3$ |
| 2-Cl | $C_3H_5$ | $CH_3$ | $OCH_3$ |
| 4-$NHCOCH_3$ | $C_3H_5$ | $CH_3$ | $OCH_3$ |
| 4-Br | $C_3H_7$ | $CH_3$ | $OCH_3$ |
| 3,4-$Cl_2$ | $C_3H_7$ | $CH_3$ | $OCH_3$ |
| 4-$C_4H_9$ | $C_3H_7$ | $CH_3$ | $OCH_3$ |
| 4-$C_2H_5$ | $C_3H_7$ | $CH_3$ | $OCH_3$ |
| 3,5-$(CH_3)_2$ | $C_3H_7$ | $CH_3$ | $OCH_3$ |
| 2,4-$(CH_3)_2$ | $C_3H_7$ | $CH_3$ | $OCH_3$ |
| 3-$OC_2H_5$ | $C_3H_7$ | $CH_3$ | $OCH_3$ |
| 4-$OCH_3$ | $C_3H_7$ | $CH_3$ | $OCH_3$ |
| 3-$OCH_3$ | $C_3H_7$ | $CH_3$ | $OCH_3$ |
| 4-$SCH_3$ | $C_3H_7$ | $CH_3$ | $OCH_3$ |
| 2-$OC_2H_5$ | $C_3H_7$ | $CH_3$ | $OCH_3$ |
| 3-$CH_3$,4-Br | $C_2H_5$ | $CH_3$ | $OCH_3$ |
| 3-$CF_3$ | $C_2H_5$ | $CH_3$ | $OCH_3$ |
| 4-F | $C_2H_5$ | $CH_3$ | $OCH_3$ |
| 4-$CH_3CO$ | $C_2H_5$ | $CH_3$ | $OCH_3$ |
| 3-$CH_3CO$ | $C_2H_5$ | $CH_3$ | $OCH_3$ |
| 4-$C_3H_7CO$ | $C_2H_5$ | $CH_3$ | $OCH_3$ |
| 4-$NHCOOCH_3$ | $C_2H_5$ | $OCH_3$ | $OCH_3$ |
| 4-CN | $C_2H_5$ | $OCH_3$ | $OCH_3$ |
| 3-CN | $C_2H_5$ | $OCH_3$ | $OCH_3$ |

EXAMPLE 19

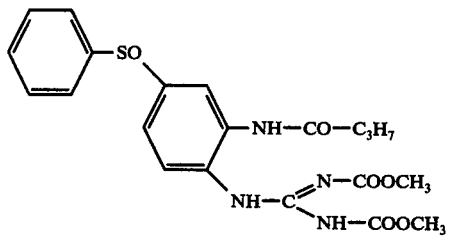

2.3 ml of $H_2O_2$ (30%) are added dropwise to a solution of 8.9 g of N-(2-butyramido-4-phenylthiophenyl)-N',N''-bis-methoxycarbonyl-guanidine (m.p. 155° C, Example 4) in 1.4 l of acetic acid anhydride. After 10 hours the batch is concentrated in vacuo, a mixture of ethyl acetate and petroleum ether added to the residue and filtered.

8.5 g of N-(2-butyramido-4-phenylsulphinylphenyl)-N,N'-bis-methoxycarbonyl-guanidine are obtained with a m.p. of 186° C (decomp.), (redissolved from methanol-/ethyl acetate). The mass spectrum shows a mol peak of 460.

Using the same method, 30 g of N-(20-methoxyacetamido-4-phenylsulphinylphenyl)-N',N''-bis-methoxycarbonyl-guanidine with a m.p. of 134° C are obtained from 31.2 g of N-(2-methoxy acetamido-4-phenylthiophenyl)-N',N''-bis-methoxycarbonyl-guanidine and 8.5 ml of $H_2O_2$ (30%).

EXAMPLE 20

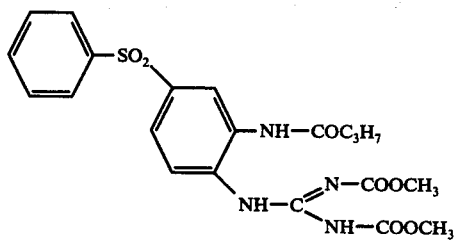

According to the method described in Example 19, 12.7 g of N-(2-butyramido-4-phenyl-sulphonyl-phenyl)-N',N''-bis-methoxy carbonyl-guanidine of m.p. 180° C are obtained from 13.3 g of N-(2-butyramido-4-phenylthio-phenyl)-N',N'' bis-methoxy carbonyl-guanidine and 20 ml of $H_2O_2$ (30%). The mass spectrum shows a mol peak of 476. In an analogous manner, 8.0 g of N-(2-methoxy acetamido-4-phenyl sulphonyl-phenyl)-N', N'''-bis-methoxy carbonyl-guanidine with a m.p. of 142° C are obtained from 8.9 g of N-(2-methoxy-acetamido-4-phenylthio-phenyl)-N',N''-bis-methoxy carbonyl-guanidine and 14 g of $H_2O_2$ (30%).

What is claimed is:

1. A member selected from the group consisting of an N-(4-phenoxy-2-amidophenyl)guanidine compound of the formula:

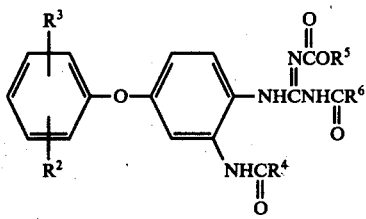

and an N-(5-phenoxy-2-amidophenyl)guanidine of the formula:

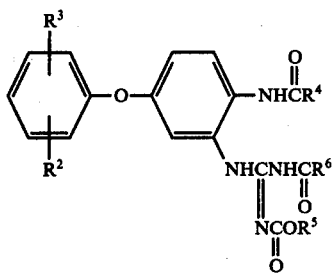

wherein
- R⁴ is alkyl of 1 to 6 carbon atoms, alkenyl of 2 to 4 carbon atoms, alkynyl of 2 to 4 carbon atoms, cycloalkyl of 3 to 10 carbon atoms, alkoxy of 1 to 6 carbon atoms, phenyl, phenylalkyl of 7 to 12 carbon atoms, alkoxyalkyl of 2 to 12 carbon atoms, phenoxyalkyl of 7 to 12 carbon atoms, amino, alkylamino of 1 to 6 carbon atoms or dialkylamino wherein each alkyl group contains 1 to 6 carbon atoms;
- R⁵ is alkyl of 1 to 6 carbon atoms, alkenyl of 2 to 6 carbon atoms or alkynyl of 2 to 6 carbon atoms; and
- R⁶ is hydrogen, alkyl of 1 to 6 carbon atoms, cycloalkyl of 3 to 10 carbon atoms, alkenyl of 2 to 6 carbon atoms, alkynyl of 2 to 6 carbon atoms, alkoxy of 1 to 6 carbon atoms, alkenyloxy of 2 to 6 carbon atoms, alkynyloxy of 2 to 6 carbon atoms, phenyl, phenylalkyl of 7 to 12 carbon atoms, phenoxyalkyl of 7 to 12 carbon atoms, alkoxyalkyl of 2 to 12 carbon atoms or alkoxyalkoxy of 2 to 12 carbon atoms;
- each of R² and R³ independent of the other is hydrogen, halogeno, alkyl of 1 to 6 carbon atoms, alkoxy of 1 to 6 carbon atoms, alkylthio of 1 to 6 carbon atoms, trifluoromethyl, alkanoyl of 1 to 6 carbon atoms, amino, alkanoylamino of 1 to 6 carbon atoms, or carbalkoxy of 2 to 7 carbon atoms.

2. A compound according to claim 1 in which
- R⁴ is alkyl of 1 to 6 carbon atoms, cycloalkyl of 3 to 7 carbon atoms, alkoxy of 1 to 4 carbon atoms, alkenyl of 2 to 4 carbon atoms, alkynyl of 2 to 4 carbon atoms, alkoxyalkyl of 2 to 8 carbon atoms, phenyl, benzyl or phenethyl;
- R⁵ is alkyl of 1 to 4 carbon atoms, alkenyl of 2 to 4 carbon atoms, or alkynyl of 2 to 4 carbon atoms;
- R⁶ is hydrogen, alkyl of 1 to 4 carbon atoms, cycloalkyl of 3 to 7 carbon atoms, alkoxy of 1 to 4 carbon atoms, alkenyl of 2 to 4 carbon atoms, alkynyl of 2 to 4 carbon atoms, alkenyloxy of 2 to 4 carbon atoms, alkynyloxy of 2 to 4 carbon atoms, alkoxyalkyl of 2 to 8 carbon atoms, alkoxyalkoxy of 2 to 8 carbon atoms, phenyl, benzyl or phenethyl; and
- each of R² and R³ independent of the other is hydrogen, fluoro, chloro, bromo, alkyl of 1 to 4 carbon atoms, alkoxy of 1 to 4 carbon atoms, alkylthio of 1 to 4 carbon atoms, trifluoromethyl, alkanoyl of 2 to 4 carbon atoms, amino, alkanoylamino of 2 to 4 carbon atoms or carbalkoxy of 2 to 7 carbon atoms.

3. A compound according to claim 2 which is an N-(4-phenoxy-2-amidophenyl)guanidine as therein defined.

4. A compound according to claim 3 wherein R⁴ is alkyl of 1 to 6 carbon atoms or alkoxyalkyl of 2 to 8 carbon atoms, R⁵ is alkyl of 1 to 4 carbon atoms, and R⁶ is alkoxy of 1 to 4 carbon atoms.

5. A compound according to claim 2 which is an N-(5-phenoxy-2-amidophenyl)guanidine as therein defined.

6. A compound according to claim 5 wherein R⁴ is alkyl of 1 to 6 carbon atoms or alkoxyalkyl of 2 to 8 carbon atoms, R⁵ is alkyl of 1 to 4 carbon atoms, and R⁶ is alkoxy of 1 to 4 carbon atoms.

7. The compound according to claim 1 which has the formula:

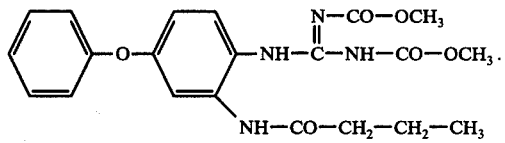

8. The compound according to claim 1 which has the formula:

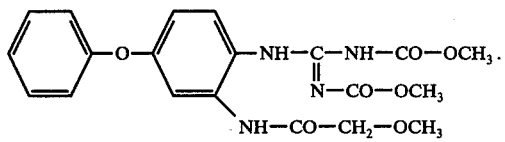

9. The compound according to claim 1 which has the formula:

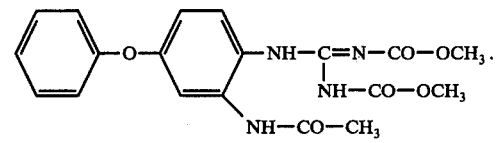

10. The compound according to claim 1 which has the formula:

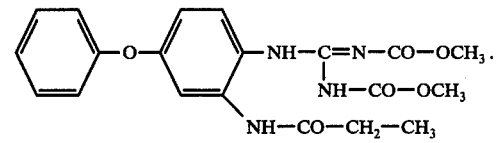

11. The compound according to claim 1 which has the formula:

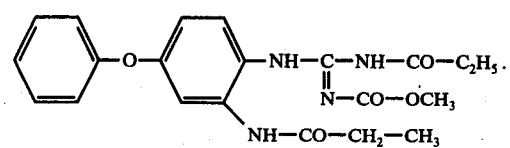

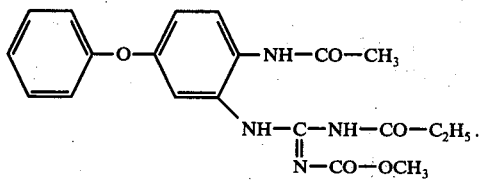

12. The compound according to claim 1 which has the formula:

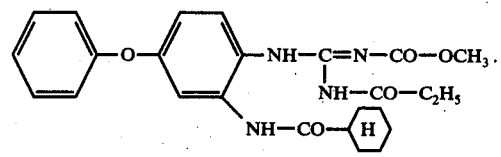

13. The compound according to claim 1 which has the formula:

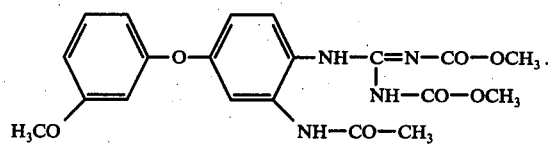

14. The compound according to claim 1 which has the formula:

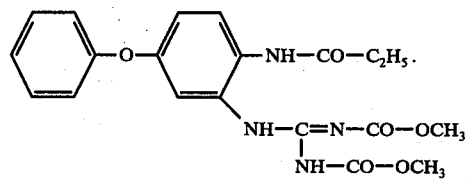

15. The compound according to claim 1 which has the formula:

16. The compound according to claim 1 which has the formula:

17. The compound according to claim 1 which has the formula:

18. The compound according to claim 1 which has the formula:

19. A pharmaceutical composition comprising an anthelmintically effective amount of a compound according to claim 1 and a pharmaceutically acceptable carrier.

20. The method of combatting thelmintic infestation in humans and other animals which comprises administering to a human or other animal an anthelmintically effective amount of a compound according to claim 1.

* * * * *